United States Patent [19]
Deibel, Jr. et al.

[11] Patent Number: 6,074,851
[45] Date of Patent: Jun. 13, 2000

[54] CATALYTIC MACRO MOLECULES HAVING CDC25B LIKE ACTIVITY

[75] Inventors: Martin R. Deibel, Jr.; Anthony W. Yem, both of Kalamazoo; Cindy L. Wolfe, Portage, all of Mich.

[73] Assignee: Pharmacia & UpJohn Company, Kalamazoo, Mich.

[21] Appl. No.: 08/848,810

[22] Filed: May 1, 1997

Related U.S. Application Data

[60] Provisional application No. 60/016,748, May 2, 1996, and provisional application No. 60/017,323, May 7, 1996.

[51] Int. Cl.[7] ............................... C12P 21/02; C12N 9/10
[52] U.S. Cl. ........................................... 435/69.7; 495/194
[58] Field of Search ................................... 435/194, 69.7

[56] References Cited

U.S. PATENT DOCUMENTS 5,441,880   8/1995   Beach et al. ............................. 435/193

FOREIGN PATENT DOCUMENTS

WO93/10242   5/1993   WIPO .
WO96/12820   5/1996   WIPO .

OTHER PUBLICATIONS

*J. Biol. Chem.*, 270(23), pp. 14229–14234 (1995).
*Proc. Natl. Acad. Sci.*, USA, 92(13), pp. 5910–5914 (1995).
*J. Biol. Chem.*, 270(8), pp. 3796–3803 (1995).
*Protein Science*, 5, pp. 5–12 (1996).
*Cell*, 67, pp. 1181–1194 (1991).
*Science*, 269*5230), pp. 1575–1577 (1995).
*J. Biol. Chem.*, 271(44), pp. 27445–27449 (1996).
*EMBO J.*, 12, pp. 53–63 (1993).
*EMBO J*, 13, pp. 4302–4310 (1994).
*Biochemical Pharmacology*, 48, pp. 2139–2141 (1994).
*J. Biol. Chem.*, 269(47), pp. 29897–29902 (1994).
*Proc. Natl. Acad. Sci.*, U.S.A., 89(24), pp. 12170–12174 (1992).
*Genomics*, 23(1), pp. 163–167 (1994).
*Cell*, 64, pp. 903–914 (1991).
*Cell*, 70, pp. 139–151 (1992).
*J. Biol. Chem.*, 269(5), pp. 3596–3604 (1994).
*Nature*, 227, pp. 680–685 (1970).
*EMBO J*, 10, pp. 4301–4309 (1991).
*New Biol.*, 3(10), pp. 959–968 (1991).
*Journal of Biological Chemisty*, 269, pp. 5989–6000 (1994).
*Journal of Biological Chemistry*, 271(9), pp. 5118–5124 (1996).
*Science*, 272, pp. 1328–1331 (1996).
*Biochemistry*, 33(51), pp. 15266–15270 (1994).
*J. Biol. Chem.*, 269 (45), pp. 28084–28090 (1994).
*Development*, 121, pp. 2047–1056 (1995).
*EMBO J*, 13(7), pp. 1549–1556 (1994).
*Genes &Development*, 6, pp. 578–590 (1992).

*Primary Examiner*—Charles L. Patterson, Jr.
*Attorney, Agent, or Firm*—Thomas A. Wootton

[57] ABSTRACT

This invention discloses novel forms of catalytic macro molecules that are related to cdc25B, a cell cycle specific phosphatase. These special domains of cdc25B, special fusions with GST, and unique peptides and proteins, their utility, and the method of making them are all described.

3 Claims, 9 Drawing Sheets

SEQUENCE LISTING (1) GENERAL INFORMATION:

(iii) NUMBER OF SEQUENCES: 45

(2) INFORMATION FOR SEQ ID NO:1:

(i) SEQUENCE CHARACTERISTICS:
       (A) LENGTH: 2890 base pairs
       (B) TYPE: nucleic acid
       (C) STRANDEDNESS: single
       (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:1:

```
GCCAGCTGTG CCGGCGTTTG TTGGCTGCCC TGCGCCCGGC CCTCCAGCCA GCCTTCTGCC      60
GGCCCCGCCG CGATGGAGGT GCCCCAGCCG GAGCCCGCGC CAGGCTCGGC TCTCAGTCCA     120
GCAGGCGTGT GCGGTGGCGC CCAGCGTCCG GGCCACCTCC CGGGCCTCCT GCTGGGATCT     180
CATGGCCTCC TGGGGTCCCC GGTGCGGGCG GCCGCTTCCT CGCCGGTCAC CACCCTCACC     240
CAGACCATGC ACGACCTCGC CGGGCTCGGC AGCCGCAGCC GCCTGACGCA CCTATCCCTG     300
TCTCGACGGG CATCCGAATC CTCCCTGTCG TCTGAATCCT CCGAATCTTC TGATGCAGGT     360
CTCTGCATGG ATTCCCCCAG CCCTATGGAC CCCCACATGG CGGAGCAGAC GTTTGAACAG     420
GCCATCCAGG CAGCCAGCCG GATCATTCGA AACGAGCAGT TTGCCATCAG ACGCTTCCAG     480
TCTATGCCGG TGAGGCTGCT GGGCCACAGC CCCGTGCTTC GGAACATCAC CAACTCCCAG     540
GCGCCCGACG GCCGGAGGAA GAGCGAGGCG GGCAGTGGAG CTGCCAGCAG CTCTGGGGAA     600
TCCCAGCTCC ACCCATGCTC TGGCAGAGTG GGCCAGCCGC AGGGAAGCCT TGCCCAGAG      660
ACCCAGCTCG GCCCCCGACC TGATGTGTCT CAGTCCTGAC CGGAAGATGG AAGTGGAGGA     720
GCTCAGCCCC CTGGCCCTAG GTCGCTTCTC TCTGACCCCT GCAGAGGGGG ATACTGAGGA     780
AGATGATGGA TTTGTGGACA TCCTAGAGAG TGACTTAAAG GATGATGATG CAGTTCCCCC     840
AGGCATGGAG AGTCTCATTA GTGCCCCACT GGTCAAGACC TTGGAAAAGG AAGAGGAAAA     900
GGACCTCGTC ATGTACAGCA AGTGCCAGCG GCTCTTCCGC TCTCCGTCCA TGCCCTGCAG     960
CGTGATCCGG CCCATCCTCA AGAGGCTGGA GCGGCCCCAG GACAGGGACA CGCCCGTGCA    1020
GAATAAGCGG AGGCGGAGCG TGACCCCTCC TGAGGAGCAG CAGGAGGCTG AGGAACCTAA    1080
AGCCCGCGTC CTCCGCTCAA AATCACTGTG TCACGATGAG ATCGAGAACC TCCTGGACAG    1140
TGACCACCGA GAGCTGATTG GAGATTACTC TAAGGCCTTC CTCCTACAGA CAGTAGACGG    1200
AAAGCACCAA GACCTCAAGT ACATCTCACC AGAAACGATG GTGGCCCTAT TGACGGGCAA    1260
GTTCAGCAAC ATCGTGGATA AGTTTGTGAT TGTAGACTGC AGATACCCCT ATGAATATGA    1320
AGGCGGGCAC ATCAAGACTG CGGTGAACTT GCCCCTGGAA CGCGACGCCG AGAGCTTCCT    1380
ACTGAAGAGC CCCATCGCGC CCTGTAGCCT GGACAAGAGA GTCATCCTCA TTTTCCACTG    1440
TGAATTCTCA TCTGAGCGTG GGCCCCGCAT GTGCCGTTTC ATCAGGGAAC GAGACCGTGC    1500
TGTCAACGAC TACCCCAGCC TCTACTACCC TGAGATGTAT ATCCTGAAAG GCGGCTACAA    1560
GGAGTTCTTC CCTCAGCACC CGAACTTCTG TGAACCCCAG GACTACCGGC CCATGAACCA    1620
CGAGGCCTTC AAGGATGAGC TAAAGACCTT CCGCCTCAAG ACTCGCAGCT GGGCTGGGGA    1680
```

-continued

```
GCGGAGCCGG CGGGAGCTCT GTAGCCGGCT GCAGGACCAG TGAGGGGCCT GCGCCAGTCC      1740

TGCTACCTCC CTTGCCTTTC GAGGCCTGAA GCCAGCTGCC CTATGGGCCT GCCGGGCTGA      1800

GGGCCTGCTG GAGGCCTCAG GTGCTGTCCA TGGGAAAGAT GGTGTGGTGT CCTGCCTGTC      1860

TGCCCCAGCC CAGATTCCCC TGTGTCATCC CATCATTTTC CATATCCTGG TGCCCCCCAC      1920

CCCTGGAAGA GCCCAGTCTG TTGAGTTAGT TAAGTTGGGT TAATACCAGC TTAAAGGCAG      1980

TATTTTGTGT CCTCCAGGAG CTTCTTGTTT CCTTGTTAGG GTTAACCCTT CATCTTCCTG      2040

TGTCCTGAAA CGCTCCTTTG TGTGTGTGTC AGCTGAGGCT GGGGAGAGCC GTGGTCCCTG      2100

AGGATGGGTC AGAGCTAAAC TCCTTCCTGG CCTGAGAGTC AGCTCTCTGC CCTGTGTACT      2160

TCCCGGGCCA GGGCTGCCCC TAATCTCTGT AGGAACCGTG GTATGTCTGC CATGTTGCCC      2220

CTTTCTCTTT TCCCCTTTCC TGTCCCACCA TACGAGCACC TCCAGCCTGA ACAGAAGCTC      2280

TTACTCTTTC CTATTTCAGT GTTACCTGTG TGCTTGGTCT GTTTGACTTT ACGCCCATCT      2340

CAGGACACTT CCGTAGACTG TTTAGGTTCC CCTGTCAAAT ATCAGTTACC CACTCGGTCC      2400

CAGTTTTGTT GCCCCAGAAA GGGATGTTAT TATCCTTGGG GGCTCCCAGG GCAAGGGTTA      2460

AGGCCTGAAT CATGAGCCTG CTGGAAGCCC AGCCCCTACT GCTGTGAACC CTGGGGCCTG      2520

ACTGCTCAGA ACTTGCTGCT GTCTTGTTGC GGATGGATGA AAGGTTGGAT GGATGGGTGG      2580

ATGGCCGTGG ATGGCCGTGG ATGCGCAGTG CCTTGCATAC CCAAACCAGG TGGGAGCGTT      2640

TTGTTGAGCA TGACACCTGC AGCAGGAATA TATGTGTGCC TATTTGTGTG GACAAAAATA      2700

TTTACACTTA GGGTTTGGAG CTATTCAAGA GGAAATGTCA CAGAAGCAGC TAAACCAAGG      2760

ACTGAGCACC CTCTGGATTC TGAATCTCAA GATGGGGGCA GGGCTGTGCT TGAAGGCCCT      2820

GCTGAGTCAT CTGTTAGGGC CTTGGTTCAA TAAAGCACTG AGCAAGTTGA GAAAAAAAAA      2880

AAAAAAAAA                                                              2890
```

(2) INFORMATION FOR SEQ ID NO:2:

(i) SEQUENCE CHARACTERISTICS:
        (A) LENGTH: 566 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:2:

```
Met Glu Val Pro Gln Pro Glu Pro Ala Pro Gly Ser Ala Leu Ser Pro
 1               5                  10                  15

Ala Gly Val Cys Gly Gly Ala Gln Arg Pro Gly His Leu Pro Gly Leu
            20                  25                  30

Leu Leu Gly Ser His Gly Leu Leu Gly Ser Pro Val Arg Ala Ala Ala
        35                  40                  45

Ser Ser Pro Val Thr Thr Leu Thr Gln Thr Met His Asp Leu Ala Gly
    50                  55                  60

Leu Gly Ser Arg Ser Arg Leu Thr His Leu Leu Ser Arg Arg Ala
65                  70                  75                  80

Ser Glu Ser Ser Leu Ser Ser Glu Ser Ser Glu Ser Ser Asp Ala Gly
                85                  90                  95

Leu Cys Met Asp Ser Pro Ser Pro Met Asp Pro His Met Ala Glu Gln
```

```
              100                 105                 110
Thr Phe Glu Gln Ala Ile Gln Ala Ala Ser Arg Ile Ile Arg Asn Glu
            115                 120                 125

Gln Phe Ala Ile Arg Arg Phe Gln Ser Met Pro Val Arg Leu Leu Gly
            130                 135                 140

His Ser Pro Val Leu Arg Asn Ile Thr Asn Ser Gln Ala Pro Asp Gly
145                 150                 155                 160

Arg Arg Lys Ser Glu Ala Gly Ser Gly Ala Ala Ser Ser Ser Gly Glu
                165                 170                 175

Asp Lys Glu Asn Asp Gly Phe Val Phe Lys Met Pro Trp Lys Pro Thr
                    180                 185                 190

His Pro Ser Ser Thr His Ala Leu Ala Glu Trp Ala Ser Arg Arg Glu
            195                 200                 205

Ala Phe Ala Gln Arg Pro Ser Ser Ala Pro Asp Leu Met Cys Leu Ser
            210                 215                 220

Pro Asp Arg Lys Met Glu Val Glu Glu Leu Ser Pro Leu Ala Leu Gly
225                 230                 235                 240

Arg Phe Ser Leu Thr Pro Ala Glu Gly Asp Thr Glu Asp Asp Gly
                245                 250                 255

Phe Val Asp Ile Leu Glu Ser Asp Leu Lys Asp Asp Ala Val Pro
                    260                 265                 270

Pro Gly Met Glu Ser Leu Ile Ser Ala Pro Leu Val Lys Thr Leu Glu
                275                 280                 285

Lys Glu Glu Glu Lys Asp Leu Val Met Tyr Ser Lys Cys Gln Arg Leu
            290                 295                 300

Phe Arg Ser Pro Ser Met Pro Cys Ser Val Ile Arg Pro Ile Leu Lys
305                 310                 315                 320

Arg Leu Glu Arg Pro Gln Asp Arg Asp Thr Pro Val Gln Asn Lys Arg
                325                 330                 335

Arg Arg Ser Val Thr Pro Pro Glu Glu Gln Gln Glu Ala Glu Glu Pro
                340                 345                 350

Lys Ala Arg Val Leu Arg Ser Lys Ser Leu Cys His Asp Glu Ile Glu
            355                 360                 365

Asn Leu Leu Asp Ser Asp His Arg Glu Leu Ile Gly Asp Tyr Ser Lys
370                 375                 380

Ala Phe Leu Leu Gln Thr Val Asp Gly Lys His Gln Asp Leu Lys Tyr
385                 390                 395                 400

Ile Ser Pro Glu Thr Met Val Ala Leu Leu Thr Gly Lys Phe Ser Asn
                    405                 410                 415

Ile Val Asp Lys Phe Val Ile Val Asp Cys Arg Tyr Pro Tyr Glu Tyr
                420                 425                 430

Glu Gly Gly His Ile Lys Thr Ala Val Asn Leu Pro Leu Glu Arg Asp
            435                 440                 445

Ala Glu Ser Phe Leu Leu Lys Ser Pro Ile Ala Pro Cys Ser Leu Asp
450                 455                 460

Lys Arg Val Ile Leu Ile Phe His Cys Glu Phe Ser Ser Glu Arg Gly
465                 470                 475                 480

Pro Arg Met Cys Arg Phe Ile Arg Glu Arg Asp Arg Ala Val Asn Asp
                485                 490                 495

Tyr Pro Ser Leu Tyr Tyr Pro Glu Met Tyr Ile Leu Lys Gly Gly Tyr
                500                 505                 510

Lys Glu Phe Phe Pro Gln His Pro Asn Phe Cys Glu Pro Gln Asp Tyr
            515                 520                 525
```

```
Arg Pro Met Asn His Glu Ala Phe Lys Asp Glu Leu Lys Thr Phe Arg
    530                 535                 540

Leu Lys Thr Arg Ser Trp Ala Gly Glu Arg Ser Arg Arg Glu Leu Cys
545                 550                 555                 560

Ser Arg Leu Gln Asp Gln
                565
```

(2) INFORMATION FOR SEQ ID NO:3:

(i) SEQUENCE CHARACTERISTICS:
        (A) LENGTH: 798 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:3:

```
CAGCGGCTCT TCCGCTCTCC GTCCATGCCC TGCAGCGTGA TCCGGCCCAT CCTCAAGAGG     60

CTGGAGCGGC CCCAGGACAG GGACACGCCC GTGCAGAATA AGCGGAGGCG GAGCGTGACC    120

CCTCCTGAGG AGCAGCAGGA GGCTGAGGAA CCTAAAGCCC GCGTCCTCCG CTCAAAATCA    180

CTGTGTCACG ATGAGATCGA GAACCTCCTG GACAGTGACC ACCGAGAGCT GATTGGAGAT    240

TACTCTAAGG CCTTCCTCCT ACAGACAGTA GACGGAAAGC ACCAAGACCT CAAGTACATC    300

TCACCAGAAA CGATGGTGGC CCTATTGACG GGCAAGTTCA GCAACATCGT GGATAAGTTT    360

GTGATTGTAG ACTGCAGATA CCCCTATGAA TATGAAGGCG GCACATCAA GACTGCGGTG     420

AACTTGCCCC TGGAACGCGA CGCCGAGAGC TTCCTACTGA AGAGCCCCAT CGCGCCCTGT    480

AGCCTGGACA AGAGAGTCAT CCTCATTTTC CACTGTGAAT TCTCATCTGA GCGTGGGCCC    540

CGCATGTGCC GTTTCATCAG GGAACGAGAC CGTGCTGTCA ACGACTACCC CAGCCTCTAC    600

TACCCTGAGA TGTATATCCT GAAAGGCGGC TACAAGGAGT TCTTCCCTCA GCACCCGAAC    660

TTCTGTGAAC CCCAGGACTA CCGGCCCATG AACCACGAGG CCTTCAAGGA TGAGCTAAAG    720

ACCTTCCGCC TCAAGACTCG CAGCTGGGCT GGGGAGCGGA GCCGGCGGGA GCTCTGTAGC    780

CGGCTGCAGG ACCAGTGA                                                  798
```

(2) INFORMATION FOR SEQ ID NO:4:

(i) SEQUENCE CHARACTERISTICS:
        (A) LENGTH: 265 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:4:

```
Gln Arg Leu Phe Arg Ser Pro Ser Met Pro Cys Ser Val Ile Arg Pro
1               5                   10                  15

Ile Leu Lys Arg Leu Glu Arg Pro Gln Asp Arg Asp Thr Pro Val Gln
                20                  25                  30

Asn Lys Arg Arg Arg Ser Val Thr Pro Pro Glu Glu Gln Gln Glu Ala
```

```
                35                  40                  45
Glu Glu Pro Lys Ala Arg Val Leu Arg Ser Lys Ser Leu Cys His Asp
         50                  55                  60

Glu Ile Glu Asn Leu Leu Asp Ser Asp His Arg Glu Leu Ile Gly Asp
 65                  70                  75                  80

Tyr Ser Lys Ala Phe Leu Leu Gln Thr Val Asp Gly Lys His Gln Asp
                 85                  90                  95

Leu Lys Tyr Ile Ser Pro Glu Thr Met Val Ala Leu Leu Thr Gly Lys
            100                 105                 110

Phe Ser Asn Ile Val Asp Lys Phe Val Ile Val Asp Cys Arg Tyr Pro
        115                 120                 125

Tyr Glu Tyr Glu Gly Gly His Ile Lys Thr Ala Val Asn Leu Pro Leu
130                 135                 140

Glu Arg Asp Ala Glu Ser Phe Leu Leu Lys Ser Pro Ile Ala Pro Cys
145                 150                 155                 160

Ser Leu Asp Lys Arg Val Ile Leu Ile Phe His Cys Glu Phe Ser Ser
                165                 170                 175

Glu Arg Gly Pro Arg Met Cys Arg Phe Ile Arg Glu Arg Asp Arg Ala
            180                 185                 190

Val Asn Asp Tyr Pro Ser Leu Tyr Tyr Pro Glu Met Tyr Ile Leu Lys
        195                 200                 205

Gly Gly Tyr Lys Glu Phe Phe Pro Gln His Pro Asn Phe Cys Glu Pro
210                 215                 220

Gln Asp Tyr Arg Pro Met Asn His Glu Ala Phe Lys Asp Glu Leu Lys
225                 230                 235                 240

Thr Phe Arg Leu Lys Thr Arg Ser Trp Ala Gly Glu Arg Ser Arg Arg
                245                 250                 255

Glu Leu Cys Ser Arg Leu Gln Asp Gln
            260                 265

(2) INFORMATION FOR SEQ ID NO:5:

(i) SEQUENCE CHARACTERISTICS:
        (A) LENGTH: 804 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:5:

GGGATCCAGC GGCTCTTCCG CTCTCCGTCC ATGCCCTGCA GCGTGATCCG GCCCATCCTC      60

AAGAGGCTGG AGCGGCCCCA GGACAGGGAC ACGCCCGTGC AGAATAAGCG GAGGCGGAGC     120

GTGACCCCTC CTGAGGAGCA GCAGGAGGCT GAGGAACCTA AAGCCCGCGT CCTCCGCTCA     180

AAATCACTGT GTCACGATGA GATCGAGAAC CTCCTGGACA GTGACCACCG AGAGCTGATT     240

GGAGATTACT CTAAGGCCTT CCTCCTACAG ACAGTAGACG GAAAGCACCA AGACCTCAAG     300

TACATCTCAC CAGAAACGAT GGTGGCCCTA TTGACGGGCA AGTTCAGCAA CATCGTGGAT     360

AAGTTTGTGA TTGTAGACTG CAGATACCCC TATGAATATG AAGGCGGGCA CATCAAGACT     420

GCGGTGAACT TGCCCCTGGA ACGCGACGCC GAGAGCTTCC TACTGAAGAG CCCCATCGCG     480

CCCTGTAGCC TGGACAAGAG AGTCATCCTC ATTTTCCACT GTGAATTCTC ATCTGAGCGT     540
```

-continued

```
GGGCCCCGCA TGTGCCGTTT CATCAGGGAA CGAGACCGTG CTGTCAACGA CTACCCCAGC        600

CTCTACTACC CTGAGATGTA TATCCTGAAA GGCGGCTACA AGGAGTTCTT CCCTCAGCAC        660

CCGAACTTCT GTGAACCCCA GGACTACCGG CCCATGAACC ACGAGGCCTT CAAGGATGAG        720

CTAAAGACCT TCCGCCTCAA GACTCGCAGC TGGGCTGGGG AGCGGAGCCG GCGGGAGCTC        780

TGTAGCCGGC TGCAGGACCA GTGA                                              804
```

(2) INFORMATION FOR SEQ ID NO:6:

(i) SEQUENCE CHARACTERISTICS:
        (A) LENGTH: 267 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:6:

```
Gly Ile Gln Arg Leu Phe Arg Ser Pro Ser Met Pro Cys Ser Val Ile
 1               5                  10                  15

Arg Pro Ile Leu Lys Arg Leu Glu Arg Pro Gln Asp Arg Asp Thr Pro
            20                  25                  30

Val Gln Asn Lys Arg Arg Ser Val Thr Pro Pro Glu Glu Gln Gln
        35                  40                  45

Glu Ala Glu Glu Pro Lys Ala Arg Val Leu Arg Ser Lys Ser Leu Cys
    50                  55                  60

His Asp Glu Ile Glu Asn Leu Leu Asp Ser Asp His Arg Glu Leu Ile
65                  70                  75                  80

Gly Asp Tyr Ser Lys Ala Phe Leu Leu Gln Thr Val Asp Gly Lys His
                85                  90                  95

Gln Asp Leu Lys Tyr Ile Ser Pro Glu Thr Met Val Ala Leu Leu Thr
            100                 105                 110

Gly Lys Phe Ser Asn Ile Val Asp Lys Phe Val Ile Val Asp Cys Arg
        115                 120                 125

Tyr Pro Tyr Glu Tyr Glu Gly Gly His Ile Lys Thr Ala Val Asn Leu
    130                 135                 140

Pro Leu Glu Arg Asp Ala Glu Ser Phe Leu Leu Lys Ser Pro Ile Ala
145                 150                 155                 160

Pro Cys Ser Leu Asp Lys Arg Val Ile Leu Ile Phe His Cys Glu Phe
                165                 170                 175

Ser Ser Glu Arg Gly Pro Arg Met Cys Arg Phe Ile Arg Glu Arg Asp
            180                 185                 190

Arg Ala Val Asn Asp Tyr Pro Ser Leu Tyr Tyr Pro Glu Met Tyr Ile
        195                 200                 205

Leu Lys Gly Gly Tyr Lys Glu Phe Phe Pro Gln His Pro Asn Phe Cys
    210                 215                 220

Glu Pro Gln Asp Tyr Arg Pro Met Asn His Glu Ala Phe Lys Asp Glu
225                 230                 235                 240

Leu Lys Thr Phe Arg Leu Lys Thr Arg Ser Trp Ala Gly Glu Arg Ser
                245                 250                 255

Arg Arg Glu Leu Cys Ser Arg Leu Gln Asp Gln
            260                 265
```

(2) INFORMATION FOR SEQ ID NO:7:

(i) SEQUENCE CHARACTERISTICS:
        (A) LENGTH: 816 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:7:

```
ATCGAAGGTC GTGGGATCCA GCGGCTCTTC CGCTCTCCGT CCATGCCCTG CAGCGTGATC      60
CGGCCCATCC TCAAGAGGCT GGAGCGGCCC CAGGACAGGG ACACGCCCGT GCAGAATAAG     120
CGGAGGCGGA GCGTGACCCC TCCTGAGGAG CAGCAGGAGG CTGAGGAACC TAAAGCCCGC     180
GTCCTCCGCT CAAAATCACT GTGTCACGAT GAGATCGAGA ACCTCCTGGA CAGTGACCAC     240
CGAGAGCTGA TTGGAGATTA CTCTAAGGCC TTCCTCCTAC AGACAGTAGA CGGAAAGCAC     300
CAAGACCTCA GTACATCTC ACCAGAAACG ATGGTGGCCC TATTGACGGG CAAGTTCAGC      360
AACATCGTGG ATAAGTTTGT GATTGTAGAC TGCAGATACC CCTATGAATA TGAAGGCGGG     420
CACATCAAGA CTGCGGTGAA CTTGCCCCTG GAACGCGACG CCGAGAGCTT CCTACTGAAG     480
AGCCCCATCG CGCCCTGTAG CCTGGACAAG AGAGTCATCC TCATTTTCCA CTGTGAATTC     540
TCATCTGAGC GTGGGCCCCG CATGTGCCGT TTCATCAGGG AACGAGACCG TGCTGTCAAC     600
GACTACCCCA GCCTCTACTA CCCTGAGATG TATATCCTGA AAGGCGGCTA CAAGGAGTTC     660
TTCCCTCAGC ACCCGAACTT CTGTGAACCC CAGGACTACC GGCCCATGAA CCACGAGGCC     720
TTCAAGGATG AGCTAAAGAC CTTCCGCCTC AAGACTCGCA GCTGGGCTGG GGAGCGGAGC     780
CGGCGGGAGC TCTGTAGCCG GCTGCAGGAC CAGTGA                              816
```

(2) INFORMATION FOR SEQ ID NO:8:

(i) SEQUENCE CHARACTERISTICS:
        (A) LENGTH: 271 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:8:

```
Ile Glu Gly Arg Gly Ile Gln Arg Leu Phe Arg Ser Pro Ser Met Pro
1               5                   10                  15

Cys Ser Val Ile Arg Pro Ile Leu Lys Arg Leu Glu Arg Pro Gln Asp
            20                  25                  30

Arg Asp Thr Pro Val Gln Asn Lys Arg Arg Arg Ser Val Thr Pro Pro
        35                  40                  45

Glu Glu Gln Gln Glu Ala Glu Glu Pro Lys Ala Arg Val Leu Arg Ser
    50                  55                  60

Lys Ser Leu Cys His Asp Glu Ile Glu Asn Leu Leu Asp Ser Asp His
65                  70                  75                  80

Arg Glu Leu Ile Gly Asp Tyr Ser Lys Ala Phe Leu Leu Gln Thr Val
                85                  90                  95
```

```
Asp Gly Lys His Gln Asp Leu Lys Tyr Ile Ser Pro Glu Thr Met Val
            100                 105                 110
Ala Leu Leu Thr Gly Lys Phe Ser Asn Ile Val Asp Lys Phe Val Ile
        115                 120                 125
Val Asp Cys Arg Tyr Pro Tyr Glu Tyr Glu Gly Gly His Ile Lys Thr
    130                 135                 140
Ala Val Asn Leu Pro Leu Glu Arg Asp Ala Glu Ser Phe Leu Leu Lys
145                 150                 155                 160
Ser Pro Ile Ala Pro Cys Ser Leu Asp Lys Arg Val Ile Leu Ile Phe
                165                 170                 175
His Cys Glu Phe Ser Ser Glu Arg Gly Pro Arg Met Cys Arg Phe Ile
            180                 185                 190
Arg Glu Arg Asp Arg Ala Val Asn Asp Tyr Pro Ser Leu Tyr Tyr Pro
        195                 200                 205
Glu Met Tyr Ile Leu Lys Gly Gly Tyr Lys Glu Phe Phe Pro Gln His
    210                 215                 220
Pro Asn Phe Cys Glu Pro Gln Asp Tyr Arg Pro Met Asn His Glu Ala
225                 230                 235                 240
Phe Lys Asp Glu Leu Lys Thr Phe Arg Leu Lys Thr Arg Ser Trp Ala
                245                 250                 255
Gly Glu Arg Ser Arg Arg Glu Leu Cys Ser Arg Leu Gln Asp Gln
            260                 265                 270
```

(2) INFORMATION FOR SEQ ID NO:9:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:9:

CGATGTATGC GGTAAACCGC AGGCATTAG                                          29

(2) INFORMATION FOR SEQ ID NO:10:

(i) SEQUENCE CHARACTERISTICS:
        (A) LENGTH: 211 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:10:

```
Val Leu Arg Ser Lys Ser Leu Cys His Asp Glu Ile Glu Asn Leu Leu
1               5                   10                  15
Asp Ser Asp His Arg Glu Leu Ile Gly Asp Tyr Ser Lys Ala Phe Leu
                20                  25                  30
Leu Gln Thr Val Asp Gly Lys His Gln Asp Leu Lys Tyr Ile Ser Pro
            35                  40                  45
Glu Thr Met Val Ala Leu Leu Thr Gly Lys Phe Ser Asn Ile Val Asp
```

```
             50                  55                  60
Lys Phe Val Ile Val Asp Cys Arg Tyr Pro Tyr Glu Tyr Glu Gly Gly
 65                  70                  75                  80

His Ile Lys Thr Ala Val Asn Leu Pro Leu Glu Arg Asp Ala Glu Ser
                 85                  90                  95

Phe Leu Leu Lys Ser Pro Ile Ala Pro Cys Ser Leu Asp Lys Arg Val
            100                 105                 110

Ile Leu Ile Phe His Cys Glu Phe Ser Ser Glu Arg Gly Pro Arg Met
        115                 120                 125

Cys Arg Phe Ile Arg Glu Arg Asp Arg Ala Val Asn Asp Tyr Pro Ser
    130                 135                 140

Leu Tyr Tyr Pro Glu Met Tyr Ile Leu Lys Gly Gly Tyr Lys Glu Phe
145                 150                 155                 160

Phe Pro Gln His Pro Asn Phe Cys Glu Pro Gln Asp Tyr Arg Pro Met
                165                 170                 175

Asn His Glu Ala Phe Lys Asp Glu Leu Lys Thr Phe Arg Leu Lys Thr
            180                 185                 190

Arg Ser Trp Ala Gly Glu Arg Ser Arg Glu Leu Cys Ser Arg Leu
        195                 200                 205

Gln Asp Gln
    210
```

(2) INFORMATION FOR SEQ ID NO:11:

(i) SEQUENCE CHARACTERISTICS:
        (A) LENGTH: 798 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:11:

```
CAGCGGCTCT TCCGCTCTCC GTCCATGCCC TGCAGCGTGA TCCGGCCCAT CCTCAAGAGG      60
CTGGAGCGGC CCCAGGACAG GGACACGCCC GTGCAGAATA GCGGAGGCG  GAGCGTGACC    120
CCTCCTGAGG AGCAGCAGGA GGCTGAGGAA ATTGAAGGCC GCGTCCTCCG CTCAAAATCA     180
CTGTGTCACG ATGAGATCGA GAACCTCCTG GACAGTGACC ACCGAGAGCT GATTGGAGAT     240
TACTCTAAGG CCTTCCTCCT ACAGACAGTA GACGGAAAGC ACCAAGACCT CAAGTACATC     300
TCACCAGAAA CGATGGTGGC CCTATTGACG GGCAAGTTCA GCAACATCGT GGATAAGTTT     360
GTGATTGTAG ACTGCAGATA CCCCTATGAA TATGAAGGCG GCACATCAA  GACTGCGGTG    420
AACTTGCCCC TGGAACGCGA CGCCGAGAGC TTCCTACTGA AGAGCCCCAT CGCGCCCTGT     480
AGCCTGGACA AGAGAGTCAT CCTCATTTTC CACTGTGAAT TCTCATCTGA GCGTGGGCCC     540
CGCATGTGCC GTTTCATCAG GGAACGAGAC CGTGCTGTCA ACGACTACCC CAGCCTCTAC     600
TACCCTGAGA TGTATATCCT GAAAGGCGGC TACAAGGAGT TCTTCCCTCA GCACCCGAAC     660
TTCTGTGAAC CCCAGGACTA CCGGCCCATG AACCACGAGG CCTTCAAGGA TGAGCTAAAG     720
ACCTTCCGCC TCAAGACTCG CAGCTGGGCT GGGGAGCGGA GCCGGCGGGA GCTCTGTAGC     780
CGGCTGCAGG ACCAGTGA                                                  798
```

(2) INFORMATION FOR SEQ ID NO:12:

(i) SEQUENCE CHARACTERISTICS:
    (A) LENGTH: 798 base pairs
    (B) TYPE: nucleic acid
    (C) STRANDEDNESS: single
    (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:12:

```
CAGCGGCTCT TCCGCTCTCC GTCCATGCCC TGCAGCGTGA TCCGGCCCAT CCTCAAGAGG     60

CTGGAGCGGC CCCAGGACAG GGACACGCCC GTGCAGAATA AGCGGAGGCG GAGCGTGACC    120

CCTCCTGAGG AGCAGCAGGA GGCTGAGGAA CCTAAAGCCC GCGTCCTCCG CTCAAAATCA    180

CTGTGTCACG ATGAGATCGA GAACCTCCTG GACAGTGACC ACCGAGAGCT GATTGGAGAT    240

TACTCTAAGG CCTTCCTCCT ACAGACAGTA GACGGAAAGC ACCAAGACCT CAAGTACATC    300

TCACCAGAAA CGATGGTGGC CCTATTGACG GGCAAGTTCA GCAACATCGT GGATAAGTTT    360

GTGATTGTAG ACTGCAGATA CCCCTATGAA TATGAAGGCG GGCACATCAA GACTGCGGTG    420

AACTTGCCCC TGGAACGCGA CGCCGAGAGC TTCCTACTGA AGAGCCCCAT CGCGCCCTGT    480

AGCCTGGACA AGAGAGTCAT CCTCATTTTC CACTGTGAAT TCTCATCTGA GCGTGGGCCC    540

CGCATGTGCC GTTTCATCAG GGAACGAGAC CGTGCTGTCA ACGACTACCC CAGCCTCTAC    600

TACCCTGAGA TGTATATCCT GAAAGGCGGC TACAAGGAGT TCTTCCCTCA GCACCCGAAC    660

TTCTGTGAAC CCCAGGACTA CCGGCCCATG AACCACGAGG CCTTCAAGGA TGAGCTAAAG    720

ACCTTCCGCC TCAAGACTCG CAGCTGGGCT GGGGAGCGGA GCAAGAAGGA GCTCTGTAGC    780

CGGCTGCAGG ACCAGTGA                                                 798
```

(2) INFORMATION FOR SEQ ID NO:13:

(i) SEQUENCE CHARACTERISTICS:
    (A) LENGTH: 798 base pairs
    (B) TYPE: nucleic acid
    (C) STRANDEDNESS: single
    (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:13:

```
CAGCGGCTCT TCCGCTCTCC GTCCATGCCC TGCAGCGTGA TCCGGCCCAT CCTCAAGAGG     60

CTGGAGCGGC CCCAGGACAG GGACACGCCC GTGCAGAATA AGCGGAGGCG GAGCGTGACC    120

CCTCCTGAGG AGCAGCAGGA GGCTGAGGAA ATTGAAGGCC GCGTCCTCCG CTCAAAATCA    180

CTGTGTCACG ATGAGATCGA GAACCTCCTG GACAGTGACC ACCGAGAGCT GATTGGAGAT    240

TACTCTAAGG CCTTCCTCCT ACAGACAGTA GACGGAAAGC ACCAAGACCT CAAGTACATC    300

TCACCAGAAA CGATGGTGGC CCTATTGACG GGCAAGTTCA GCAACATCGT GGATAAGTTT    360

GTGATTGTAG ACTGCAGATA CCCCTATGAA TATGAAGGCG GGCACATCAA GACTGCGGTG    420

AACTTGCCCC TGGAACGCGA CGCCGAGAGC TTCCTACTGA AGAGCCCCAT CGCGCCCTGT    480

AGCCTGGACA AGAGAGTCAT CCTCATTTTC CACTGTGAAT TCTCATCTGA GCGTGGGCCC    540

CGCATGTGCC GTTTCATCAG GGAACGAGAC CGTGCTGTCA ACGACTACCC CAGCCTCTAC    600
```

```
TACCCTGAGA TGTATATCCT GAAAGGCGGC TACAAGGAGT TCTTCCCTCA GCACCCGAAC        660

TTCTGTGAAC CCCAGGACTA CCGGCCCATG AACCACGAGG CCTTCAAGGA TGAGCTAAAG        720

ACCTTCCGCC TCAAGACTCG CAGCTGGGCT GGGGAGCGGA GCAAGAAGGA GCTCTGTAGC        780

CGGCTGCAGG ACCAGTGA                                                      798
```

(2) INFORMATION FOR SEQ ID NO:14:

(i) SEQUENCE CHARACTERISTICS:
        (A) LENGTH: 265 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:14:

```
Gln Arg Leu Phe Arg Ser Pro Ser Met Pro Cys Ser Val Ile Arg Pro
1               5                  10                  15

Ile Leu Lys Arg Leu Glu Arg Pro Gln Asp Arg Asp Thr Pro Val Gln
            20                  25                  30

Asn Lys Arg Arg Arg Ser Val Thr Pro Pro Glu Glu Gln Gln Glu Ala
        35                  40                  45

Glu Glu Ile Glu Gly Arg Val Leu Arg Ser Lys Ser Leu Cys His Asp
    50                  55                  60

Glu Ile Glu Asn Leu Leu Asp Ser Asp His Arg Glu Leu Ile Gly Asp
65                  70                  75                  80

Tyr Ser Lys Ala Phe Leu Leu Gln Thr Val Asp Gly Lys His Gln Asp
                85                  90                  95

Leu Lys Tyr Ile Ser Pro Glu Thr Met Val Ala Leu Leu Thr Gly Lys
            100                 105                 110

Phe Ser Asn Ile Val Asp Lys Phe Val Ile Val Asp Cys Arg Tyr Pro
        115                 120                 125

Tyr Glu Tyr Glu Gly Gly His Ile Lys Thr Ala Val Asn Leu Pro Leu
    130                 135                 140

Glu Arg Asp Ala Glu Ser Phe Leu Leu Lys Ser Pro Ile Ala Pro Cys
145                 150                 155                 160

Ser Leu Asp Lys Arg Val Ile Leu Ile Phe His Cys Glu Phe Ser Ser
                165                 170                 175

Glu Arg Gly Pro Arg Met Cys Arg Phe Ile Arg Glu Arg Asp Arg Ala
            180                 185                 190

Val Asn Asp Tyr Pro Ser Leu Tyr Tyr Pro Glu Met Tyr Ile Leu Lys
        195                 200                 205

Gly Gly Tyr Lys Glu Phe Phe Pro Gln His Pro Asn Phe Cys Glu Pro
    210                 215                 220

Gln Asp Tyr Arg Pro Met Asn His Glu Ala Phe Lys Asp Glu Leu Lys
225                 230                 235                 240

Thr Phe Arg Leu Lys Thr Arg Ser Trp Ala Gly Glu Arg Ser Arg Arg
                245                 250                 255

Glu Leu Cys Ser Arg Leu Gln Asp Gln
            260                 265
```

(2) INFORMATION FOR SEQ ID NO:15:

(i) SEQUENCE CHARACTERISTICS:
    (A) LENGTH: 265 amino acids
    (B) TYPE: amino acid
    (C) STRANDEDNESS: single
    (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:15:

```
Gln Arg Leu Phe Arg Ser Pro Ser Met Pro Cys Ser Val Ile Arg Pro
1               5                   10                  15

Ile Leu Lys Arg Leu Glu Arg Pro Gln Asp Arg Asp Thr Pro Val Gln
            20                  25                  30

Asn Lys Arg Arg Arg Ser Val Thr Pro Pro Glu Glu Gln Gln Glu Ala
        35                  40                  45

Glu Glu Pro Lys Ala Arg Val Leu Arg Ser Lys Ser Leu Cys His Asp
    50                  55                  60

Glu Ile Glu Asn Leu Leu Asp Ser Asp His Arg Glu Leu Ile Gly Asp
65                  70                  75                  80

Tyr Ser Lys Ala Phe Leu Leu Gln Thr Val Asp Gly Lys His Gln Asp
                85                  90                  95

Leu Lys Tyr Ile Ser Pro Glu Thr Met Val Ala Leu Leu Thr Gly Lys
                100                 105                 110

Phe Ser Asn Ile Val Asp Lys Phe Val Ile Val Asp Cys Arg Tyr Pro
            115                 120                 125

Tyr Glu Tyr Glu Gly Gly His Ile Lys Thr Ala Val Asn Leu Pro Leu
    130                 135                 140

Glu Arg Asp Ala Glu Ser Phe Leu Leu Lys Ser Pro Ile Ala Pro Cys
145                 150                 155                 160

Ser Leu Asp Lys Arg Val Ile Leu Ile Phe His Cys Glu Phe Ser Ser
                165                 170                 175

Glu Arg Gly Pro Arg Met Cys Arg Phe Ile Arg Glu Arg Asp Arg Ala
                180                 185                 190

Val Asn Asp Tyr Pro Ser Leu Tyr Tyr Pro Glu Met Tyr Ile Leu Lys
            195                 200                 205

Gly Gly Tyr Lys Glu Phe Phe Pro Gln His Pro Asn Phe Cys Glu Pro
    210                 215                 220

Gln Asp Tyr Arg Pro Met Asn His Glu Ala Phe Lys Asp Glu Leu Lys
225                 230                 235                 240

Thr Phe Arg Leu Lys Thr Arg Ser Trp Ala Gly Glu Arg Ser Lys Lys
                245                 250                 255

Glu Leu Cys Ser Arg Leu Gln Asp Gln
                260                 265
```

(2) INFORMATION FOR SEQ ID NO:16:

(i) SEQUENCE CHARACTERISTICS:
        (A) LENGTH: 265 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:16:

```
Gln Arg Leu Phe Arg Ser Pro Ser Met Pro Cys Ser Val Ile Arg Pro
1               5                   10                  15

Ile Leu Lys Arg Leu Glu Arg Pro Gln Asp Arg Asp Thr Pro Val Gln
            20                  25                  30

Asn Lys Arg Arg Arg Ser Val Thr Pro Pro Glu Glu Gln Gln Glu Ala
        35                  40                  45

Glu Glu Ile Glu Gly Arg Val Leu Arg Ser Lys Ser Leu Cys His Asp
    50                  55                  60

Glu Ile Glu Asn Leu Leu Asp Ser Asp His Arg Glu Leu Ile Gly Asp
65                  70                  75                  80

Tyr Ser Lys Ala Phe Leu Leu Gln Thr Val Asp Gly Lys His Gln Asp
                85                  90                  95

Leu Lys Tyr Ile Ser Pro Glu Thr Met Val Ala Leu Leu Thr Gly Lys
            100                 105                 110

Phe Ser Asn Ile Val Asp Lys Phe Val Ile Val Asp Cys Arg Tyr Pro
        115                 120                 125

Tyr Glu Tyr Glu Gly Gly His Ile Lys Thr Ala Val Asn Leu Pro Leu
130                 135                 140

Glu Arg Asp Ala Glu Ser Phe Leu Leu Lys Ser Pro Ile Ala Pro Cys
145                 150                 155                 160

Ser Leu Asp Lys Arg Val Ile Leu Ile Phe His Cys Glu Phe Ser Ser
                165                 170                 175

Glu Arg Gly Pro Arg Met Cys Arg Phe Ile Arg Glu Arg Asp Arg Ala
            180                 185                 190

Val Asn Asp Tyr Pro Ser Leu Tyr Tyr Pro Glu Met Tyr Ile Leu Lys
        195                 200                 205

Gly Gly Tyr Lys Glu Phe Phe Pro Gln His Pro Asn Phe Cys Glu Pro
    210                 215                 220

Gln Asp Tyr Arg Pro Met Asn His Glu Ala Phe Lys Asp Glu Leu Lys
225                 230                 235                 240

Thr Phe Arg Leu Lys Thr Arg Ser Trp Ala Gly Glu Arg Ser Lys Lys
                245                 250                 255

Glu Leu Cys Ser Arg Leu Gln Asp Gln
            260                 265
```

(2) INFORMATION FOR SEQ ID NO:17:

(i) SEQUENCE CHARACTERISTICS:
        (A) LENGTH: 603 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:17:

```
GTCCTCCGCT CAAAATCACT GTGTCACGAT GAGATCGAGA ACCTCCTGGA CAGTGACCAC      60

CGAGAGCTGA TTGGAGATTA CTCTAAGGCC TTCCTCCTAC AGACAGTAGA CGGAAAGCAC     120

CAAGACCTCA AGTACATCTC ACCAGAAACG ATGGTGGCCC TATTGACGGG CAAGTTCAGC     180

AACATCGTGG ATAAGTTTGT GATTGTAGAC TGCAGATACC CCTATGAATA TGAAGGCGGG     240
```

```
CACATCAAGA CTGCGGTGAA CTTGCCCCTG AACGCGACG CCGAGAGCTT CCTACTGAAG      300

AGCCCCATCG CGCCCTGTAG CCTGGACAAG AGAGTCATCC TCATTTTCCA CTGTGAATTC      360

TCATCTGAGC GTGGGCCCCG CATGTGCCGT TTCATCAGGG AACGAGACCG TGCTGTCAAC      420

GACTACCCCA GCCTCTACTA CCCTGAGATG TATATCCTGA AAGGCGGCTA CAAGGAGTTC      480

TTCCCTCAGC ACCCGAACTT CTGTGAACCC CAGGACTACC GGCCCATGAA CCACGAGGCC      540

TTCAAGGATG AGCTAAAGAC CTTCCGCCTC AAGACTCGCA GCTGGGCTGG GGAGCGGAGC      600

CGG                                                                    603

(2) INFORMATION FOR SEQ ID NO:18:

(i) SEQUENCE CHARACTERISTICS:
        (A) LENGTH: 603 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:18:

GTCCTCCGCT CAAAATCACT GTGTCACGAT GAGATCGAGA ACCTCCTGGA CAGTGACCAC       60

CGAGAGCTGA TTGGAGATTA CTCTAAGGCC TTCCTCCTAC AGACAGTAGA CGGAAAGCAC      120

CAAGACCTCA AGTACATCTC ACCAGAAACG ATGGTGGCCC TATTGACGGG CAAGTTCAGC      180

AACATCGTGG ATAAGTTTGT GATTGTAGAC TGCAGATACC CCTATGAATA TGAAGGCGGG      240

CACATCAAGA CTGCGGTGAA CTTGCCCCTG AACGCGACG CCGAGAGCTT CCTACTGAAG      300

AGCCCCATCG CGCCCTGTAG CCTGGACAAG AGAGTCATCC TCATTTTCCA CTGTGAATTC      360

TCATCTGAGC GTGGGCCCCG CATGTGCCGT TTCATCAGGG AACGAGACCG TGCTGTCAAC      420

GACTACCCCA GCCTCTACTA CCCTGAGATG TATATCCTGA AAGGCGGCTA CAAGGAGTTC      480

TTCCCTCAGC ACCCGAACTT CTGTGAACCC CAGGACTACC GGCCCATGAA CCACGAGGCC      540

TTCAAGGATG AGCTAAAGAC CTTCCGCCTC AAGACTCGCA GCTGGGCTGG GGAGCGGAGC      600

CGG                                                                    603

(2) INFORMATION FOR SEQ ID NO:19:

(i) SEQUENCE CHARACTERISTICS:
        (A) LENGTH: 636 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:19:

GTCCTCCGCT CAAAATCACT GTGTCACGAT GAGATCGAGA ACCTCCTGGA CAGTGACCAC       60

CGAGAGCTGA TTGGAGATTA CTCTAAGGCC TTCCTCCTAC AGACAGTAGA CGGAAAGCAC      120

CAAGACCTCA AGTACATCTC ACCAGAAACG ATGGTGGCCC TATTGACGGG CAAGTTCAGC      180

AACATCGTGG ATAAGTTTGT GATTGTAGAC TGCAGATACC CCTATGAATA TGAAGGCGGG      240
```

```
CACATCAAGA CTGCGGTGAA CTTGCCCCTG GAACGCGACG CCGAGAGCTT CCTACTGAAG      300

AGCCCCATCG CGCCCTGTAG CCTGGACAAG AGAGTCATCC TCATTTTCCA CTGTGAATTC      360

TCATCTGAGC GTGGGCCCCG CATGTGCCGT TCATCAGGG AACGAGACCG TGCTGTCAAC       420

GACTACCCCA GCCTCTACTA CCCTGAGATG TATATCCTGA AAGGCGGCTA CAAGGAGTTC      480

TTCCCTCAGC ACCCGAACTT CTGTGAACCC CAGGACTACC GGCCCATGAA CCACGAGGCC      540

TTCAAGGATG AGCTAAAGAC CTTCCGCCTC AAGACTCGCA GCTGGGCTGG GGAGCGGAGC      600

AAGAAGGAGC TCTGTAGCCG GCTGCAGGAC CAGTGA                                636
```

(2) INFORMATION FOR SEQ ID NO:20:

(i) SEQUENCE CHARACTERISTICS:
        (A) LENGTH: 636 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:20:

```
GTCCTCCGCT CAAAATCACT GTGTCACGAT GAGATCGAGA ACCTCCTGGA CAGTGACCAC       60

CGAGAGCTGA TTGGAGATTA CTCTAAGGCC TTCCTCCTAC AGACAGTAGA CGGAAAGCAC      120

CAAGACCTCA AGTACATCTC ACCAGAAACG ATGGTGGCCC TATTGACGGG CAAGTTCAGC      180

AACATCGTGG ATAAGTTTGT GATTGTAGAC TGCAGATACC CCTATGAATA TGAAGGCGGG      240

CACATCAAGA CTGCGGTGAA CTTGCCCCTG GAACGCGACG CCGAGAGCTT CCTACTGAAG      300

AGCCCCATCG CGCCCTGTAG CCTGGACAAG AGAGTCATCC TCATTTTCCA CTGTGAATTC      360

TCATCTGAGC GTGGGCCCCG CATGTGCCGT TCATCAGGG AACGAGACCG TGCTGTCAAC       420

GACTACCCCA GCCTCTACTA CCCTGAGATG TATATCCTGA AAGGCGGCTA CAAGGAGTTC      480

TTCCCTCAGC ACCCGAACTT CTGTGAACCC CAGGACTACC GGCCCATGAA CCACGAGGCC      540

TTCAAGGATG AGCTAAAGAC CTTCCGCCTC AAGACTCGCA GCTGGGCTGG GGAGCGGAGC      600

AAGAAGGAGC TCTGTAGCCG GCTGCAGGAC CAGTGA                                636
```

(2) INFORMATION FOR SEQ ID NO:21:

(i) SEQUENCE CHARACTERISTICS:
        (A) LENGTH: 201 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:21:

```
Val Leu Arg Ser Lys Ser Leu Cys His Asp Glu Ile Glu Asn Leu Leu
1               5                  10                  15

Asp Ser Asp His Arg Glu Leu Ile Gly Asp Tyr Ser Lys Ala Phe Leu
            20                  25                  30

Leu Gln Thr Val Asp Gly Lys His Gln Asp Leu Lys Tyr Ile Ser Pro
        35                  40                  45
```

```
Glu Thr Met Val Ala Leu Leu Thr Gly Lys Phe Ser Asn Ile Val Asp
     50                  55                  60

Lys Phe Val Ile Val Asp Cys Arg Tyr Pro Tyr Glu Tyr Glu Gly Gly
 65                  70                  75                  80

His Ile Lys Thr Ala Val Asn Leu Pro Leu Glu Arg Asp Ala Glu Ser
                 85                  90                  95

Phe Leu Leu Lys Ser Pro Ile Ala Pro Cys Ser Leu Asp Lys Arg Val
                100                 105                 110

Ile Leu Ile Phe His Cys Glu Phe Ser Ser Glu Arg Gly Pro Arg Met
                115                 120                 125

Cys Arg Phe Ile Arg Glu Arg Asp Arg Ala Val Asn Asp Tyr Pro Ser
                130                 135                 140

Leu Tyr Tyr Pro Glu Met Tyr Ile Leu Lys Gly Gly Tyr Lys Glu Phe
145                 150                 155                 160

Phe Pro Gln His Pro Asn Phe Cys Glu Pro Gln Asp Tyr Arg Pro Met
                165                 170                 175

Asn His Glu Ala Phe Lys Asp Glu Leu Lys Thr Phe Arg Leu Lys Thr
                180                 185                 190

Arg Ser Trp Ala Gly Glu Arg Ser Arg
                195                 200
```

(2) INFORMATION FOR SEQ ID NO:22:

(i) SEQUENCE CHARACTERISTICS:
        (A) LENGTH: 211 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:22:

```
Val Leu Arg Ser Lys Ser Leu Cys His Asp Glu Ile Glu Asn Leu Leu
 1               5                  10                  15

Asp Ser Asp His Arg Glu Leu Ile Gly Asp Tyr Ser Lys Ala Phe Leu
                 20                  25                  30

Leu Gln Thr Val Asp Gly Lys His Gln Asp Leu Lys Tyr Ile Ser Pro
             35                  40                  45

Glu Thr Met Val Ala Leu Leu Thr Gly Lys Phe Ser Asn Ile Val Asp
     50                  55                  60

Lys Phe Val Ile Val Asp Cys Arg Tyr Pro Tyr Glu Tyr Glu Gly Gly
 65                  70                  75                  80

His Ile Lys Thr Ala Val Asn Leu Pro Leu Glu Arg Asp Ala Glu Ser
                 85                  90                  95

Phe Leu Leu Lys Ser Pro Ile Ala Pro Cys Ser Leu Asp Lys Arg Val
                100                 105                 110

Ile Leu Ile Phe His Cys Glu Phe Ser Ser Glu Arg Gly Pro Arg Met
                115                 120                 125

Cys Arg Phe Ile Arg Glu Arg Asp Arg Ala Val Asn Asp Tyr Pro Ser
                130                 135                 140

Leu Tyr Tyr Pro Glu Met Tyr Ile Leu Lys Gly Gly Tyr Lys Glu Phe
145                 150                 155                 160

Phe Pro Gln His Pro Asn Phe Cys Glu Pro Gln Asp Tyr Arg Pro Met
                165                 170                 175
```

```
Asn His Glu Ala Phe Lys Asp Glu Leu Lys Thr Phe Arg Leu Lys Thr
            180                 185                 190

Arg Ser Trp Ala Gly Glu Arg Ser Lys Lys Glu Leu Cys Ser Arg Leu
        195                 200                 205

Gln Asp Gln
    210
```

(2) INFORMATION FOR SEQ ID NO:23:

(i) SEQUENCE CHARACTERISTICS:
        (A) LENGTH: 211 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:23:

```
Val Leu Arg Ser Lys Ser Leu Cys His Asp Glu Ile Glu Asn Leu Leu
1               5                   10                  15

Asp Ser Asp His Arg Glu Leu Ile Gly Asp Tyr Ser Lys Ala Phe Leu
            20                  25                  30

Leu Gln Thr Val Asp Gly Lys His Gln Asp Leu Lys Tyr Ile Ser Pro
        35                  40                  45

Glu Thr Met Val Ala Leu Leu Thr Gly Lys Phe Ser Asn Ile Val Asp
50                  55                  60

Lys Phe Val Ile Val Asp Cys Arg Tyr Pro Tyr Glu Tyr Glu Gly Gly
65                  70                  75                  80

His Ile Lys Thr Ala Val Asn Leu Pro Leu Glu Arg Asp Ala Glu Ser
                85                  90                  95

Phe Leu Leu Lys Ser Pro Ile Ala Pro Cys Ser Leu Asp Lys Arg Val
            100                 105                 110

Ile Leu Ile Phe His Cys Glu Phe Ser Ser Glu Arg Gly Pro Arg Met
            115                 120                 125

Cys Arg Phe Ile Arg Glu Arg Asp Arg Ala Val Asn Asp Tyr Pro Ser
130                 135                 140

Leu Tyr Tyr Pro Glu Met Tyr Ile Leu Lys Gly Gly Tyr Lys Glu Phe
145                 150                 155                 160

Phe Pro Gln His Pro Asn Phe Cys Glu Pro Gln Asp Tyr Arg Pro Met
            165                 170                 175

Asn His Glu Ala Phe Lys Asp Glu Leu Lys Thr Phe Arg Leu Lys Thr
            180                 185                 190

Arg Ser Trp Ala Gly Glu Arg Ser Lys Lys Glu Leu Cys Ser Arg Leu
        195                 200                 205

Gln Asp Gln
    210
```

(2) INFORMATION FOR SEQ ID NO:24:

(i) SEQUENCE CHARACTERISTICS:
        (A) LENGTH: 166 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:24:

```
His Asp Glu Ile Glu Asn Leu Leu Asp Ser Asp His Arg Glu Leu Ile
1               5                   10                  15

Gly Asp Tyr Ser Lys Ala Phe Leu Leu Gln Thr Val Asp Gly Lys His
                20                  25                  30

Gln Asp Leu Lys Tyr Ile Ser Pro Glu Thr Met Val Ala Leu Leu Thr
            35                  40                  45

Gly Lys Phe Ser Asn Ile Val Asp Lys Phe Val Ile Val Asp Cys Arg
        50                  55                  60

Tyr Pro Tyr Glu Tyr Glu Gly His Ile Lys Thr Ala Val Asn Leu
65              70              75                  80

Pro Leu Glu Arg Asp Ala Glu Ser Phe Leu Leu Lys Ser Pro Ile Ala
                85                  90                  95

Pro Cys Ser Leu Asp Lys Arg Val Ile Leu Ile Phe His Cys Glu Phe
                100                 105                 110

Ser Ser Glu Arg Gly Pro Arg Met Cys Arg Phe Ile Arg Glu Arg Asp
            115                 120                 125

Arg Ala Val Asn Asp Tyr Pro Ser Leu Tyr Tyr Pro Glu Met Tyr Ile
        130                 135                 140

Leu Lys Gly Gly Tyr Lys Glu Phe Phe Pro Gln His Pro Asn Phe Cys
145             150                 155                 160

Glu Pro Gln Asp Tyr Arg
                165
```

(2) INFORMATION FOR SEQ ID NO:25:

(i) SEQUENCE CHARACTERISTICS:
      (A) LENGTH: 185 amino acids
      (B) TYPE: amino acid
      (C) STRANDEDNESS: single
      (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:25:

```
Met Ser Gly Ser Phe Glu Leu Ser Val Gln Asp Leu Asn Asp Leu Leu
1               5                   10                  15

Ser Asp Gly Ser Gly Cys Tyr Ser Leu Pro Ser Gln Pro Cys Asn Glu
                20                  25                  30

Val Thr Pro Arg Ile Tyr Val Gly Asn Ala Ser Val Ala Gln Asp Ile
            35                  40                  45

Pro Lys Leu Gln Lys Leu Gly Ile Thr His Val Leu Asn Ala Ala Glu
        50                  55                  60

Gly Arg Ser Phe Met His Val Asn Thr Asn Ala Asn Phe Tyr Lys Asp
65              70                  75                  80

Ser Gly Ile Thr Tyr Leu Gly Ile Lys Ala Asn Asp Thr Gln Glu Phe
                85                  90                  95

Asn Leu Ser Ala Tyr Phe Glu Arg Ala Ala Asp Phe Ile Asp Gln Ala
                100                 105                 110

Leu Ala Gln Lys Asn Gly Arg Val Leu Val His Cys Arg Glu Gly Tyr
```

```
                115              120              125
Ser Arg Ser Pro Thr Leu Val Ile Ala Tyr Leu Met Met Arg Gln Lys
        130              135              140

Met Asp Val Lys Ser Ala Leu Ser Ile Val Arg Gln Asn Arg Glu Ile
145              150              155              160

Gly Pro Asn Asp Gly Phe Leu Ala Gln Leu Cys Gln Leu Asn Asp Arg
                165              170              175

Leu Ala Lys Glu Gly Lys Leu Lys Pro
        180              185
```

(2) INFORMATION FOR SEQ ID NO:26:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:26:

ATCGAAGGTC GTGGGATCC                                        19

(2) INFORMATION FOR SEQ ID NO:27:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:27:

```
Ile Glu Gly Arg Gly Ile
1               5
```

(2) INFORMATION FOR SEQ ID NO:28:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:28:

CTCGAGCGGC CGCATCGTGA CTGACTGA                              28

(2) INFORMATION FOR SEQ ID NO:29:

(i) SEQUENCE CHARACTERISTICS:
        (A) LENGTH: 8 amino acids
        (B) TYPE: amino acid
        (C) STRANDEDNESS: single (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:29:

Ser Ser Gly Arg Ile Val Thr Asp
1               5

(2) INFORMATION FOR SEQ ID NO:30:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:30:

GCGGATCCAG CGGCTCTTCC GCTCTC                                              26

(2) INFORMATION FOR SEQ ID NO:31:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:31:

GCCTCGAGTC ACTGGTCCTG CAGCCG                                              26

(2) INFORMATION FOR SEQ ID NO:32:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:32:

CCAGCGGCTC TTCCGCTCTC CGTC                                                24

(2) INFORMATION FOR SEQ ID NO:33:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:33:

AGCCGGCTGC AGGACCAGTG A                                              21

(2) INFORMATION FOR SEQ ID NO:34:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:34:

GACGGAGAGC GGAAGAGCCG CTGG                                           24

(2) INFORMATION FOR SEQ ID NO:35:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:35:

TCACTGGTCC TGCAGCCGGC T                                              21

(2) INFORMATION FOR SEQ ID NO:36:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:36:

GCCTCGAGTC ACTGGTCCTG CAGCCG                                         26

(2) INFORMATION FOR SEQ ID NO:37:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:37:

GAAGGTCGTG GGATCCAGCG GCTCTTCCGC                                         30

(2) INFORMATION FOR SEQ ID NO:38:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:38:

CAGGACCAGT GACTCGAGCG GCCGCAT                                            27

(2) INFORMATION FOR SEQ ID NO:39:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:39:

GCGGAAGAGC CGCTGGATCC CACGACCTTC                                         30

(2) INFORMATION FOR SEQ ID NO:40:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:40:

ATGCGGCCGC TCGAGTCACT GGTCCTG                                            27

(2) INFORMATION FOR SEQ ID NO:41:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:41:

GCGGAGGACG CGGCCTTCAA TTTCCTCAGC CTC    33

(2) INFORMATION FOR SEQ ID NO:42:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:42:

GGGGAGCGGA GCAAGAAGGA GCTCTGTAGC    30

(2) INFORMATION FOR SEQ ID NO:43:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:43:

GAGGCTGAGG AAATTGAAGG CCGCGTCCTC CGC    33

(2) INFORMATION FOR SEQ ID NO:44:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:44:

GCGGATCCAG CACGATGAGA TCGAGAA    27

(2) INFORMATION FOR SEQ ID NO:45:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO

```
    (xi) SEQUENCE DESCRIPTION: SEQ ID NO:45:

GCCTCGAGTC ACCGGTAGTC CTGGGGT                                              27
```

CATALYTIC MACRO MOLECULES HAVING CDC25B LIKE ACTIVITY

CROSS-REFERENCE TO RELATED APPLICATIONS

This application claims the benefit of U.S. provisional application Ser. No. 60/016,748 filed May 2, 1996 and Ser. No. 60/017,323 filed May 7, 1996, under 35 USC §119(e)(i).

FIELD OF THE INVENTION

This invention relates to the field of protein phosphatases, specifically cdc25B like enzymes.

INFORMATION DISCLOSURE

P. Aroca, D. P. Bottatro, T. Ishibashi, S. A. Aaronson, and E. Santos. "Human dual specificity phosphatase VHR activates maturation promotion factor and triggers meiotic maturation in Xenopus oocytes." *J. Biol. Chem.*, vol. 270(23), pp. 14229–34 (1995).

David H. Beach and Konstantin Galaktionov, U.S. Pat. No. 5,441,880, issued Aug. 15, 1995. "Human cdc25 genes, encoded products and uses thereof."

J. M. Denu and J. E. Dixon. "A catalytic mechanism for the dual-specific phosphatases." *Proc. Natl. Acad. Sci. U.S.A.*, vol. 92(13), pp. 5910–4 (1995).

J. M. Denu, G. Zhou, L. Wu, R. Zhao, J. Yuvaniyama, M. A. Saper, and J. E. Dixon. "The purification and characterization of a human dual-specific protein tyrosine phosphatase." *J. Biol. Chem., vol.* 270(8), pp. 3796–803 (1995).

J. W. Eckstein, P. Beer-Romero, and I. Berdo. "Identification of an essential acidic residue in Cdc25 protein phosphatase and a general three-dimensional model for a core region in protein phosphatases." *Protein Sceince*, vol. 5, pp. 5–12 (1996).

K. I. Galaktionov, and D. H. Beach, "Specific activation of cdc25 tyrosine phosphatases by B-type cyclins: Evidence for multiple roles of mitotic cyclins," *Cell*, vol. 67, pp. 1181–1194 (1991).

Galaktionov K., Lee A. K., Eckstein J., Draetta G., Meckler J., Loda M., Beach D., "CDC25 phosphatases as potential human oncogenes." *Science*, vol. 269(5230), pp. 1575–7 (1995).

Gottlin E. B., Xu X., Epstein D. M., Burke S. P., Eckstein J. W., Ballou D. P., and Dixon J. E. "Kinetic analysis of the catalytic domain of human cdc25B" *J. Biol. Chem.*, vol. 271(44), pp. 27445–9 (1996).

I. Hoffman, P. R. Clarke, M. J. Marcote, E. Karsenti, and G. Draetta, "Phosphorylation and activation of human cdc25C by cdc2-cyclin B and its involvement in the self-amplification of MPF at mitosis." *EMBO J*, vol.12 pp. 53–63 (1993).

I. Hoffman, G. Draetta, and E. Karsenti, "Activation of the phosphatase activity of human cdc25A by a cdk2-cyclin E dependent phosphorylation at the G1/S transition." *EMBO J*, vol. 13, pp. 4302–4310 (1994).

Takashi Horiguchi, et al., "Dnacin A1 and Dnacin B1 are antitumor antibiotics that inhibit cdc25b phosphatase activity." *Biochemical Pharmacology*, vol. 48 pp. 2139–2141, (1994).

T. Ishibashi, D. P. Bottaro, P. Michieli, C.A. Kelley, and S. A. Aaronson. "A novel dual specificity phosphatase induced by serum stimulation and heat shock," *J. Biol. Chem.* 1994 Nov 25); 269(47): 29897–902.

T. Ishibashi, D. P. Bottaro, A. Chan, T. Miki, and S. A. Aaronson. "Expression cloning of a human dual-specificity phosphatase." *Proc. Natl. Acad. Sci., U.S.A.*, vol. 89(24), pp. 12170–4 (1992).

A. Kamb, P. A. Futreal, J. Rosenthal, C. Cochran, K. D. Harshman, Q. Liu, R. S. Phelps, S. V. Tavtigian, T. Tran, C. Hussey, et-al. "Localization of the VHR phosphatase gene and its analysis as a candidate for BRCA1." *Genomics.* vol.23(1), pp. 163–7 (1992).

A. Kumagai and W. G. Dunphy, "The cdc25 protein controls tyrosine dephosphorylation of the cdc2 protein in a cell-free system." *Cell*, vol. 64 pp. 903–914 (1991).

A. Kumagai and W. G. Dunphy, "Regulation of the cdc25 protein during the cell cycle in Xenopus extracts." *Cell*, vol. 70 pp. 139–151 (1992).

S. P. Kwak, D. J. Hakes, K. J. Martell, and J. E. Dixon. "Isolation and characterization of a human dual specificity protein-tyrosine phosphatase gene." *J. Biol. Chem.*, vol. 269(5), pp. 3596–604 (1994).

U. K. Laemmli, "Cleavage of structural proteins during the assembly of the head of bacteriophage T4." *Nature*, vol. 227 pp.680–685 (1970).

J. B. A. Millar, C. H. McGowan, G. Lenaers, R. Jones, and P. Russell, "p80cdc25 mitotic inducer is the tyrosine phosphatase that activates p34cdc2 kinase in fission yeast." *EMBO J*, vol. 10, pp. 4301–4309 (1991).

Nagata A., Igarashi M., Jinno S., Suto K., and Okayama H. "An additional homolog of the fission yeast cdc25+ gene occurs in humans and is highly expressed in some cancer cells." *New Biol. vol.* 3(10), pp. 959–68 (1991). GENBANK/S78187.

U. Strausfeld, A. Fernandez, J -P. Capony, F. Girard, N. Lautredou, J. Derancourt, J -C. Labbe, and N. J. C. Lamb, "Activation of p34cdc2 protein kinase by microinjection of human cdc25C into mammalian cells." *Journal of Biological Chemistry*, vol. 269 pp. 5989–6000 (1994).

Xu Xu and S. P. Burke, "Roles of Active Site Residues and the $NH_2$-terminal Domain in the Catalysis and Substrate Binding of Human Cdc25." *Journal of Biological Chemistry*, vol. 271, no.9, pp 5118–5124 (1996).

J. Yuvaniyama, J. M. Denu, J. E. Dixon, and M. A. Saper. "Crystal Structure of the Dual Specificity Protein Phosphatase VHR." *Science*, vol. 272, pp, 1328–1331.

Z. Y. Zhang, Y. Wang, L. Wu, E. B. Fauman, J. A. Stuckey, H. L. Schubert, M. A. Saper, and J. E. Dixon. "The Cys(X)5Arg catalytic motif in phosphoester hydrolysis." *Biochemistry.* vol. 33(51), pp. 15266–70 (1994).

G. Zhou, J. M. Denu, L. Wu, and J. E. Dixon. The catalytic role of Cys124 in the dual specificity phosphatase VHR. "Results demonstrate that the dual specificity phosphatases and the tyrosine-specific PTPases employ similar catalytic mechanisms." *J. Biol. Chem.*, vol. 269(45), pp. 28084–90 (1994).

BACKGROUND OF THE INVENTION

In eukaryotic cells, mitosis is initiated following the activation of a protein kinase known as MPF, the M-phase specific histone kinase or more simply as the M-phase kinase. This kinase consists of at least three subunits; the catalytic subunit (cdc2), a regulatory subunit (cyclin B) and a low molecular weight subunit (p13-Sucl).

There is much interest in the regulation of the phosphatase which dephosphorylates cdc2 because of its role in the activation of MPF. Genetic studies in fission yeast have established that the cdc25 gene function is essential for the initiation of mitosis, Nurse, P. et al., *Mol. Gen. Genet.* 146:167–178 (1976). The cdc25 gene product serves as a rate-determining activator of the cdc2 protein kinase, Russell, P. and P. Nurse, *Cell* 45:145–153 (1986);

Ducommun, B. et al., *Biochem. Biophys. Res. Common.* 167:301–309 (1990); Moreno, S. et al., *Nature* 344:549–552 (1990)). Mutant cdc2-F15, whose product cannot be phosphorylated on tyrosine, bypasses the requirement for cdc25 protein function, Gould, K. and P. Nurse, *Nature* 342:39–45 (1989)). Additional work suggested that cdc25 is a cdc2 phosphatase, Kumagai, A. and W. G. Dunphy, *Cell* 64:903–914 (1991) and Strausfeld, U. et al., *Nature* 351:242–245 (1991).

Apparently cdc25 acts as a cdc2 phosphatase which dephosphorylates tyrosine and possibly threonine residues on $p_{34}cdc2$ thus regulating MPF activation, Dunphy, W. G. and A. Kumagai, *Cell* 67:189–196 (1991) and Gautier, J. et al., *Cell* 67:197–211 (1991). Because cdc25 phosphatases are responsible for the dephosphorylation and activation of cyclin-dependent protein kinases, they help control cell cycle progression.

As a cell cycle specific phosphatase, cdc25B is believed to be crucial for progression from G2 through mitosis. To study this protein and/or develop a screen using this protein one requires the isolation of the active catalytic domain of cdc25B. Unfortunately, the native full length cdc25B is difficult to obtain due to its sensitivity to proteolysis and its low abundance in mammalian cells On the other hand, a GST fusion protein with cdc25B has been described which has activity. The latter protein has partial solubility and measurable activity as a phosphatase, but as a fusion protein is not amenable to structural analyses including crystallographic studies. To date, successful removal of the GST moiety from a full length fusion protein of cdc25B, with subsequent isolation of full length cdc25B without a GST tag, has not been reported. There have been attempts to make smaller recombinant catalytic domains of cdc25.B, including one recently described by Horiguchi et al. The latter recombinant form includes a GST fusion partner and codes for amino acids 355–566, Takashi Horiguchi, et al., *Biochemical Pharmacology*, Vol. 48 pp. 2139–2141, (1994), incorporated by reference, but this construct appears to result in low protein yields and the protein product is poorly soluble with low activity. The observation of low activity of recombinant forms of cdc25B expressed in *E. coli* is most likely attributable to improper enzyme folding.

Stable recombinant forms of cdc25B are needed that have improved activity making them suitable for use in enzyme assays with improved solubility characteristics. Stable recombinant forms of the protein that are capable of easy manipulation for crystallography studies in order to better understand and characterize these types of phosphatases by structural analyses and models are also needed. This invention provides macro molecules having these and other desirable characteristics.

SUMMARY OF THE INVENTION

This invention discloses the fusions shown in FIG. 6,
where, the different parts of the fusions are shown as different lines in a boxy where the figure represents a construct that can be composed of either nucleic or amino acids,
where,
a) the boxes, lines and numbers are not drawn to scale,
b) the GST region, labeled GST, is shown with a straight line down the middle of the box,
c) the protease cleavage site, labeled P, is shown with a dotted line down the middle of the box,
d) the restriction site, labeled R, is shown with a wavey line down the middle of the box,
e) the GST region is relatively large, compared to the cleavage and restriction sites
f) the cdc25B like region, labeled cdc25B like, is shown as a box with a heavy line down the middle of the box, where the numbers above the box indicating DNA nucleotide residues and th(e numbers below the box indicating peptide amino acid residues,
where, with reference to the cdc25B like region,
a) the region has about the number of sequences indicated by the numbers shown,
b) the region has either the same amino acids as native cdc25B or substituted nucleic or amino acid residues,
where the native nucleic or amino acid residues of the cdc 25B like region are those sequences disclosed in the CHARTS and sequence listings.
where the substituted nucleic or amino acid residues of the cdc 25B like region are those sequences disclosed as substitutions in the CHARTS and sequence listings or where the subsitituted nucleic or amino acid residues may be obtained by deleting, adding or replacing one to several nucleic or amino acid residues
where the fusion, when it is a protein, may optionally be associated with a bacterial polypeptide.

More particularly the fusion shown above may have a protease cleavage site is created to be responsive to thrombin or Factor Xa, the restriction site may be Bam HI.

The fusions may be nucleic acid residue fusions, DNA, or they may be amino acid residue fusions, peptides or proteins. One of the GST fusions is where the fusion is a peptide where the cdc25B like region is comprised of the amino acid residues shown in CHART 6 as $cdc25B^{302-566}$ or SEQ. ID. NO. 4. This is also described as a fusion protein comprising, GST-Ile-Glu-Gly-Arg-Gly-Ile-SEQ. ID. NO. 4. Other specific peptide fusions are comprised of the following: the cdc25B like region is comprised of the amino acid residues shown in CHART 14 as Mutein 1 or SEQ. ID. NO. 14; the fusion protein comprising, GST-Ile-Glu-Gly-Arg-Gly-Ile-SEQ. ID. NO. 14; the fusion protein where the cdc25B like region is comprised of the amino acid residues shown in CHART 14 as Mutein 2 or SEQ. ID. NO. 15; The fusion protein comprising, GST-Ile-Glu-Gly-Arg-Gly-Ile-SEQ. ID. NO. 15; the fusion protein where the cdc25B like region is comprised of the amino acid residues shown in CHART 14 as Mutein 3 or SEQ. ID. NO. 16; the fusion protein comprising, GST-Ile-Glu-Gly-Arg-Gly-Ile-SEQ ID. NO. 16; the fusion protein comprising, GST-Ile-Glu-Gly-Arg-Gly-Ile-$Gln^{302}$ . . . $Gln^{566}$.

Disclosed are fusion proteins that are closely associated with a bacterial polypeptide, especially where said polypeptide is a chaperonin. Especially any of the fusion proteins where the chaperonin polypeptides are DnaK and/or GroEL.

The fusions are also nucleic acid fusions, the nucleic acid, or DNA residues of course code for the peptides that are expressed from the DNA, but the nucleic acids residues are also rightly considered fusions. Some of the specific DNA or nucleic acid fusions are comprised of nucleic acid residues where the nucleic acid residues of the cdc25B like region are comprised of the nucleic acid residues shown in CHART 5 and CHART 13 as $cdc25B^{976-1773}$ or SEQ ID. NO. 4; comprised of the nucleic acid residues shown in CHART 13 as Mutein1 or SEQ ID. NO. 11; comprised of the nucleic acid residues shown in CHART 13 as Mutein2 or SEQ ID. NO. 12; comprised of the nucleic acid residues shown in CHART 13 as Mutein3 or SEQ ID. NO. 13.

Some of these fusions may be more particularly described as: GST-Xa-BamHI restriction site-cdc25B(976–1773)-

XhoI restriction site, or as GST-Xa-GGG-ATC-cdc25B (976–1773)-XhoI restriction site, see CHART 2.

Fragments of the complete fusions described above are also described and claimed. Specific fragments of nucleic acids from, or associated with, the construction of the fusions are disclosed, such as those disclosed in various CHARTS and particularly CHART E or SEQ. ID. NO. 3.

Many of the fusion fragments are peptides or amino acid residues. Proteins, peptides, protein and peptide fragments or as they are also called, amino acid residues covalently linked with amide bonds, are disclosed. More particularly the following peptides are important and may be useful by themselves, or as essential intermediates, the amino acid residues disclosed in CHART 6 or SEQ. ID. NO. 4; the amino acid residues disclosed in CHART 11 or SEQ. ID. NO. 9; the amino acid residues disclosed in CHART 12 or SEQ. ID. NO. 10; the amino acid residues disclosed in CHART 16 as Mutein1 or SEQ. NO. 21; the amino acid residues disclosed in CHART 16 as Mutein 2 or SEQ. ID. NO. 22; the amino acid residues disclosed in CHART 16 as Mutein 3 or SEQ. ID. NO. 23; the amino acid residues, of SEQ. ID. NO. 9, that is produced from the fusion protein that is GST-Ile-Glu-Gly-Arg-Gly-Ile-SEQ. ID. NO. 4.

The peptides and proteins, the nucleic acids or DNA residues may also be called catalytic macromolecules. In some cases these macromolecules are identified precisely as products derived from a particular process, such as, a catalytic macromolecule comprising the amino acid residues, of SEQ. ID. NO. 21, that is produced from the fusion protein that is GST-Ile-Glu-Gly-Arg-Gly-Ile-SEQ. ID. NO. 14; a catalytic macromolecule comprising the amino acid residues of SEQ. ID. NO. 22, that is produced from the fusion protein that is GST-Ile-Glu-Gly-Arg-Gly-Ile-SEQ. ID. NO. 15; a catalytic macromolecule comprising the amino acid residues of SEQ. ID. NO. 23, that is produced from the fusion protein that is GST-Ile-Glu-Gly-Arg-Gly-Ile-SEQ. ID. NO. 16.

In addition to the fusions described by the figure above there are other fusions also related to cdc25B that are disclosed by this invention. Fusions are disclosed here that may be selected from any of the fusions shown in FIG. 7, where, the different parts of the fusions are shown as different lines in the box, where a) the GST region, i, labelled GST, with a straight line in the box, b) the protease cleavage site, is shown as a dotted line in the box, labelled "P,"

c) the restriction site is shown as a wavey line in the box, labelled "R," and d) the VHR like region is shown as a heavy line in the box, labelled "VHR"

where the numbers above the box indicating DNA nucleotide residues and the numbers below the box indicating amino acid residues, where the figure, shown above, represents either nucleic acids or amino acids, where the boxes, lines and numbers are not drawn to scale, where the GST is relatively large, the cleavage and restriction sites relatively small and the VHR region has about the number of sequences indicated by the numbers, where the numbers correspond to the same residue numbers as full length VHR region of cdc25B.

The VHR like region of cdc25B may be more particularly described as those sequences disclosed in Chart 17, SEQ. ID. NO. 24 and SEQ. ID. NO 25, and 70% homologous and substantially similar sequences thereof.

The process of making any of the fusions, peptides, constructs or molecules, intermediates, intermediate processes, steps and procedures used to created the fusions and peptides for all of the fusions and peptides are described herein.

BRIEF DESCRIPTION OF THE DRAWINGS

FIG. 1A shows the restriction sites, oligonucleotide primers and portions of cdc25B sequence involved in the PCR reaction and plasmid formation of plasmid pGEX-5X-3. FIG. 1A is an expanded portion of the plasmid shown in FIG. 1B.

FIG. 1B shows the plasmid construction of plasmid pGEX-5X-3. FIG. 1B contains the expanded portion of the segment shown in FIG. 1A, FIG. 2.

FIG. 3 is a gel filtration size exclusion chromatograph of the purified monomeric special minimal domain cdc25B(356–556).

FIG. 4 is an agarose gel electrophoresis showing the product of the PCR reaction (0.8 Kb)).

FIG. 5 is an agarose gel electrophoresis of plasmid mini preps obtained from transformed JM109 E coli.

FIG. 6 shows a cdc25B fusion molecule with the GST region labeled GST, the protease cleavage site labeled P, the restriction site labeled R and the cdc25B like region labeled as such and where the numbers above the box indicate certain DNA nucleotide residues and the numbers below the box indicating certain peptide amino acid residues.

FIG. 7 shows a cdc25B fusion having a VHR like region. In this Figure the GST region is labeled GST, the protease cleavage site is labeled P, the restriction site is labeled R and the cdc25B like region labeled as such where the numbers above the box indicating certain DNA nucleotide residues and the numbers below the box indicating certain peptide amino acid residues.

FIG. 8 is described in CHART 1 and compares three different fusions. Construct number one represents the fusion produced by David H. Beach and Konstantin Galaktionov, U.S. Pat. No. 5,441,880 and *Cell* (1991) 67; 1181–1194. Construct number two represents the fusion produced by Takashi Horiguchi, et al., *Biochemical Pharmacology*, vol. 48 pp. 2139–2141, (1994). Construct number three represents the fusion disclosed by this invention.

Figure 1A:
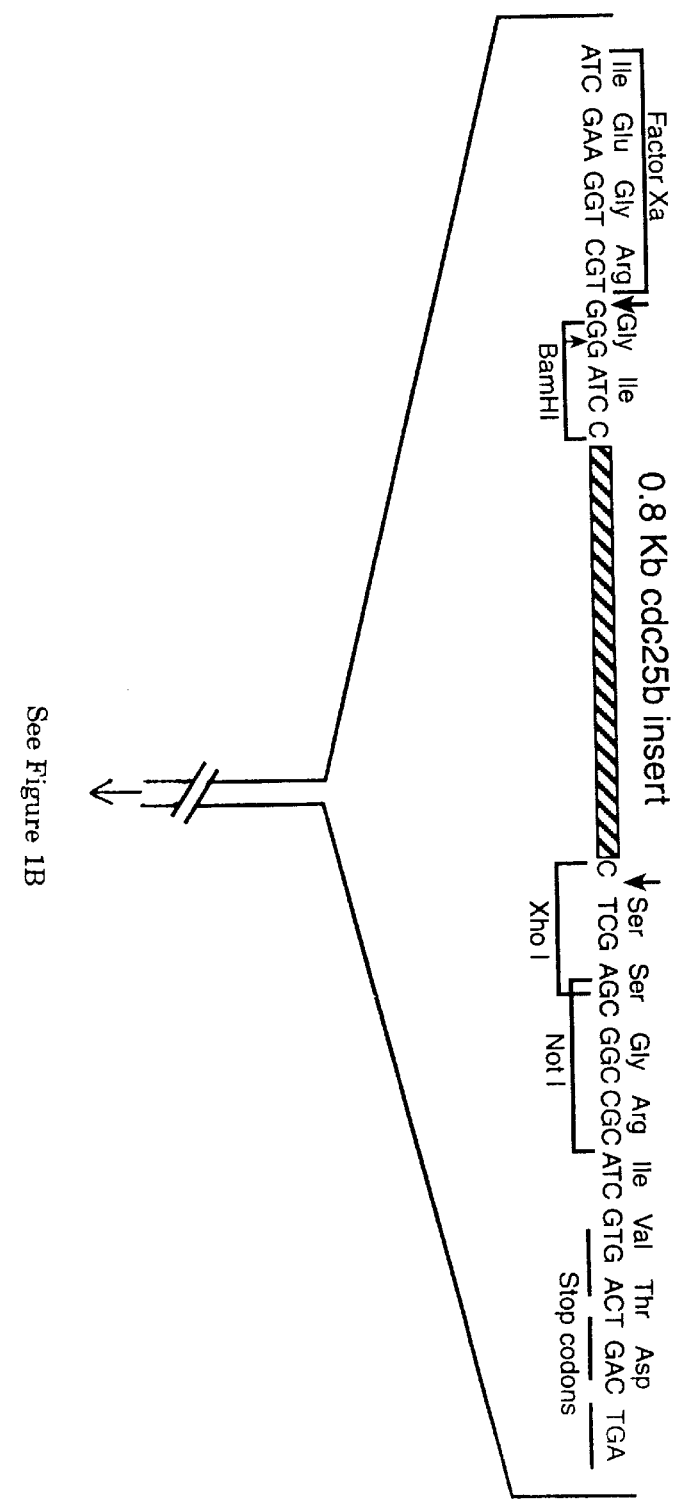
FIG. 1A.

ADDITIONAL MORE DETAILED
DESCRIPTION OF THE INVENTION

Definitions

Definitions are included throughout this document in addition to the specific definitions and sources of materials noted below.

"compound(s)" or "macromolecule(s)" means any molecular structure including complex poly residue entities such as covalently linked amino acids like proteins and peptides and covalently linked nucleic acid residues such as a gene or gene fragment or any fusions of nucleic acid residues or the related peptidic like compounds that would result from the expression of nucleic acids.

"native extraction/buffer systems" are common extraction buffer systems such as, lysozyme (1 mg/ml) and fresh dithiothreitol (DTT) (20 mM) in TEN buffer (50 mM Tris HCl, 0.5 mM EDTA, 300 mM NaCl, 0.2% NP-40, pH 8.0)

"BCIP" is 5-bromo-4-chloro-3-indolyl phosphate.

"JM109 E. coli cells," are a strain of cells available from Promega® as competent E. coli cells.

"IPTG" is isopropyl-β-D-thiogalactopyranoside from Boehringer Mannheim, Indianapolis, Ind.

Many of the kits used in this invention such as "the GeneClean® kit" and "a RPM plasmid isolation kit" (RPM-rapid pure minipreps) are obtained from Bio 101®., LaJolla, Calif.

"MORPH" is a site-specific plasmid DNA mutagenesis kit obtained from 5 PRIME→3 PRIME, Inc.®, Boulder, Colo.

"LB media" is a solution containing tryptone, yeast extract, sodium chloride and water. It is commerically available from Gibco-BRL.®, Gaithersburg, Md.

"NBT" is nitroblue tetrazolium.

"PAGE" is polyacrylamide gel electrophoresis.

Assays of PNPP hydrolase activity associated with cdc25B are conducted using the reagents described by Horiguchi et al. (*Biochemical Pharmacology*, Vol. 48 pp. 2139–2141, (1994)). This is what is meant by "enzymatically active in a defined way with the calorimetric substrate, p-nitrophenyl phosphate (PNPP)."

"PVDF" is polyvinylidene difluoride.

"SDS" is sodium dodecyl sulfate.

"TA cloning kit," containing the pCRII plasmid, and INVαF' cells is obtained from InVitroGen®, San Diego, Calif.

Temperatures are in degrees celcius unless noted otherwise and may be indicated with a number, a number supercase "o ," a number, uppercase"C", a number, supercase "°", uppercase C, or other obvious combinations or methods. e.g. 37, 37°, 37 C, 37° C., etc.

The present invention relates to a method of regulating (inhibiting or enhancing) cell division and to agents or compositions useful for regulating the cell cycle. The present invention has the same uses as previously disclosed human cdc25B in addition to having other uses not possible with previously disclosed human cdc25B because of its physical characteristics. Described herein are novel recombinant fusion constructs that produce macromolecules that are soluble and that perform some similar biochemical functions as full length cdc25B constructs such as phosphatase activity, but these constructs generally have more activity, are more soluble, do not require refolding and in some cases may be crystallized. The crystallizible compounds described herein are useful for crystallography and for drug development screening tools. These compounds should also allow improved structure-based design for the development of novel phosphatase antagonists, the latter being expected to result in an anti-neoplastic drug.

The compounds or macro molecules, usually peptides and nucleic acid sequences, described herein would make superior drug screening tools over previously disclosed cdc25B proteins because of their characteristics including enhanced activity for some of the constructs. The compounds described herein would be superior over known macromolecules, such as other previously described proteins and peptides, for studies of cdc25B enzyme kinetics and mechanistic studies because these novel compounds are monomeric in structure and because these uniquely designed sequences do not display anomalies present in inhibitor kinetics seen with known GST fusion proteins of cdc 25B. Furthermore, the compounds that are proteins and peptides, or derivatives thereof, described herein can be created without a subsequent refolding step, thus providing simple consistent procedures for making highly active compounds.

The compounds described herein would make superior subjects of crystallization studies because of their solubility properties. These compounds would make superior templates for studies of structure activity relationships because their structure is more suitable for structure based design strategies than known cdc25B compounds. The compounds disclosed herein should be particularly useful for transfection studies in mammalian cells designed to test in vivo mechanism of action and proof of concept studies. The GST-cdc25B full length enzyme cannot be purified to homogeneity using prior art descriptions of purification of GST fusion proteins. The compounds and procedures disclosed herein do allow the creation of highly purified and homogeneous active protein, as defined by several criteria.

Previously described cdc25B protein is full length protein, usually created as a GST fusion with cdc25B. This type of cdc25B is not stable when stored over time. As a consequence of this instability, the kinetics of the full length protein change over time and this changes the binding constant for the substrate, leading to inconclusive results in any screening operation using the full length protein with a GST tag. Few stability problems are detected with the constructs and fusions disclosed by this invention.

Full length cdc25B, is previously disclosed in U.S. Pat. No. 5,441,880 ('880), incorporated by reference. It also appears in a paper by K. I. Galaktionov, and D. H. Beach, "Specific activation of cdc25 tyrosine phosphatases by B-type cyclins: Evidence for multiple roles of mitotic cyclins" *Cell* (1991) 67; 1181–1194. The known cDNA and amino acid sequence of cdc25B is produced in Chart 3 (cDNA) and Chart 4 (amino acids), below. The DNA and protein sequences are numbered and this numbering system is retained throughout this document. For example, the full length protein is numbered from 1 (Met) to 566 (Gln). Another method of referring to this sequence is $cdc25B^{1-566}$, or cdc25B (1–566). For example, a macromolecule of only 10 amino acids, might be described as "$cdc25B^{556-566}$" which would describe a macromolecule of 10 amino acids identical to the last 10 amino acids in Chart 4, i.e. "Arg-Glu-Leu-Cys-Ser-Arg-Leii-Gln-Asp-Gln."

The full length protein, by itself, without anything attached to the first or last amino acids, is not easily manipulated in the laboratory. The protein is usually attached or "fused" to a "tag" or "fusion partner" creating a "fusion," or "fusion construct" or "construct." Cdc25B is frequently attached to glutathione S-transferase (GST). Indeed, this is the only form of the protein that was previously disclosed.

In other situations a few amino acids may be inserted between the GST and the peptide. These amino acid inserts should be understood from the context of the disclosure in general, or they may be specifically delineated. Thus, it is possible the construct may be represented as "GST-Gly-Ile-cdc25B (302–566)."

In addition to amino acids and GST, there may be other linking molecules between the fusion partner and the protein. For example, in some embodiments of this invention an intervening factor Xa cleavage site will be produced, and this may be introduced between the GST and the cdc25B. In these situations the linking molecules or amino acids should be apparent from the text, even though they are not delineated, or the precise construct may be identified, for example as, GST-Xa site-Gly-Ile-cdc25B (302–566).

When various tag(s) or fusion partners are attached to the protein, the whole complex may simply be referred to as "GST-cdc25B." If this complex (including fusion tag) were to be comprised of the full length protein it may be called, GST-cdc25B$^{1-566}$. Compounds differing from the full length cdc25B might be described with numbers indicating a different sequence than the full length, but the numbers will always correspond to the full length sequence in Charts 3 and 4. For example, cdc25B$^{556-566}$ would describe a macromolecule of 10 amino acids identical to the last amino acids in Chart 2, i.e. "Arg-Glu-Leu-Cys-Ser-Arg-Leu-Gln-Asp-Gln." An alternative method of describing this sequence would be to refer to the amino acids and a number indicating the relative segment, e.g. "Arg 556 to Gln 566." Another example would be a reference to a GST fusion to an Xa site, fused to Gly-Ile fused to amino acids 302 to 566 of cdc25B, this would be described as "GST-Xa site-Gly-Ile-cdc25B (302–566)."

The following embodiments and characteristics of this invention are described.

The fusion protein (GST-Xa site-Gly-Ile-cdc25B$^{302-566}$), which is defined as a GST polypeptide fused to a truncated form of human cdc25B, containing residues 302–566, is disclosed, as well as various forms of the truncated cdc25B protein itself. These fusion proteins and peptide fragments are soluble using native extraction/buffer systems (see definitions). The products of these extractions, using native extraction/buffer systems, are enzymatically active in a defined way (see definitions) with the calorimetric substrate, p-nitrophenyl phosphate (PNPP).

The special domains can be released from their GST fusion partners by digestion of an engineered factor Xa cleavage site between the GST and cdc25B sequences, respectively. These special constructs, or domains, once they are released from their GST fusion partners, are especially suitable for use in enzyme assays, crystallography, and other examples requiring a stable enzyme. All of the factor Xa released minimal domains lacking the GST moiety can be concentrated to greater than 10 milligrams per ml without precipitation, an advantage for crystallography studies.

When these special constructs, such as, cdc25B (356–556), are evaluated for enzymatic activity, using PNPP as a substrate, the $K_m$ is significantly lower (i.e., improved binding constant for substrate) than published values for other cdc25B constructs, and at least 6–7 fold lower than for GST-cdc25B$^{31-566}$ The lower $K_m$ reflects better binding properties to the substrate than any enzymes currently known. The $V_{max}$ we calculate for the minimal domain, cdc25B (356–556), is greater than published values, showing that the cdc25B (356–556) enzyme is a more active enzyme than that previously disclosed.

When the protein cdc25B (356–556) is evaluated for enzymatic activity, using PNPP as a substrate, the $K_m$ is 2–3-fold lower than for the parent GST-Xa-Gly-Ile-cdc25B (302–566) protein.

This invention also comprises a method for the preparation of active, homogeneous peptide special domains of cdc25B, including cdc25B (356–556) and mutated forms of cdc25B(356–566).

Disclosed herein from a previous disclosure is the expression of GST-cdc25B (355–566), a different protein which is closely related to the sequence of the minimal domain being claimed in the present invention, but results in low yields of poorly soluble, low activity GST-cdc25B$^{355-566}$ product. This form was previously reported in the literature. Takashi Horiguchi, et al., *Biochemical Pharmacology*, vol. 48 pp. 2139–2141, (1994). "Dnacin A1 and Dnacin B1 are antitumor antibiotics that inhibit cdc25b phosphatase activity." The reported form contained GST and no attempt to remove the GST was reporter.

General Discussion of the Methods

The sequence of the full length DNA is available in GenBank, accession number M81934.gb__pr., submission by Beach and Galaktionov. This sequence was also disclosed by Nagata, who used a different numbering system. According to the Nagata numbering system, the coding sequences would be numbered 241–1941, See, Nagata A., Igarashi M., Jinno S., Suto K., and Okayama H. *New Biol.* vol. 3(10), pp. 959–68 (1991). GENBANK/S78187. The Beach and Galaktionov numbering system is used throughout this document. Initially, PCR primers containing Bam HI (5' sense) and Xho I (3' antisense) restriction sites were prepared. Unpurified products of the PCR reaction are ligated into a TA cloning vector (pCRII; InVitroGen®) according to standard procedures. The ligated TA vector is used to transform INVαF' cells. See, Charts 1 and 2, and FIG. 1A and FIG. 1B, for an overview of the procedures described herein and a general description of the essential intermediates and products produced.

Figure 1B:
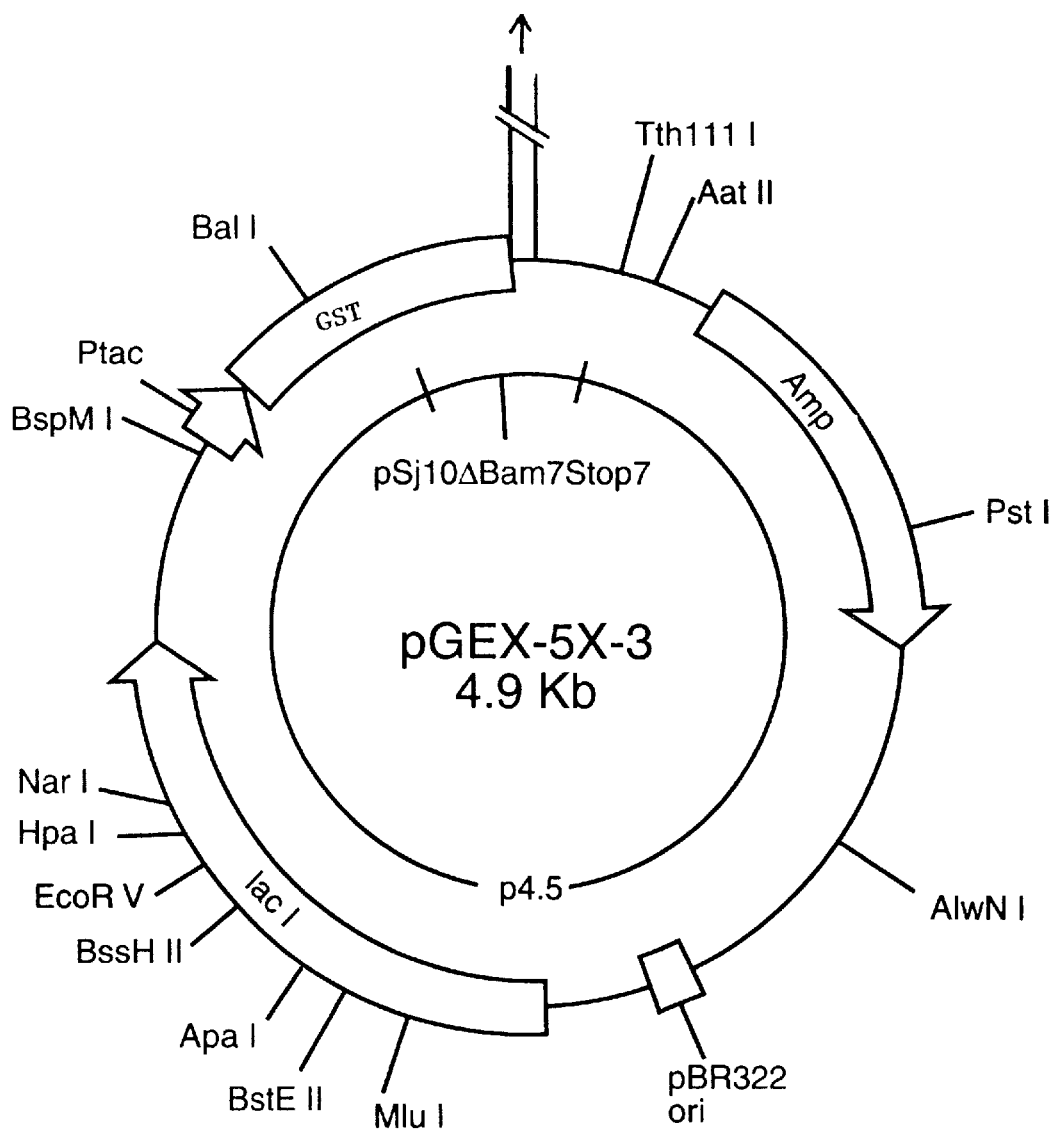
FIG. 1B.
Figure 6:
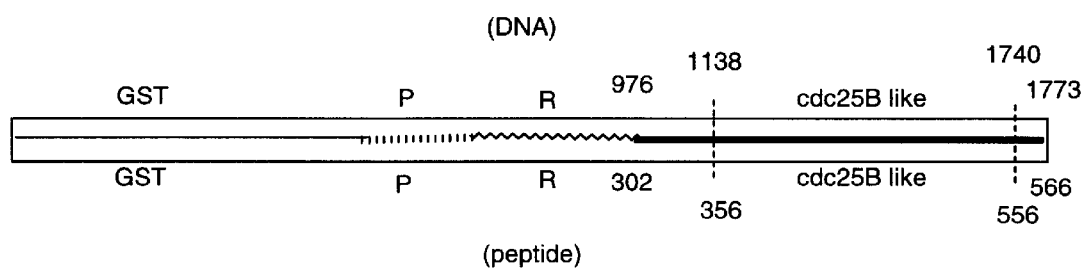
FIG. 6.
Figure 7:
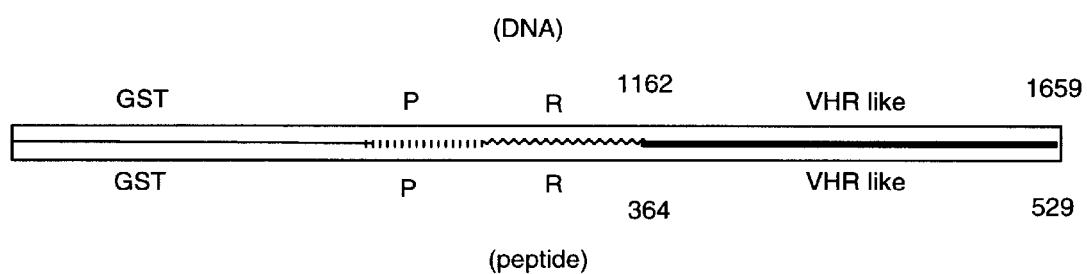
FIG. 7.

Chart 1 describes and FIG. 6 shows, GST fusion proteins compares two other constructs with the construct disclosed herein. Chart 1 describes and FIG. 6 shows, Item 1, a GST fusion protein of cdc25B (1–566), (disclosed by Beach and Galaktionov); Item 2, a GST fusion protein of cdc25B (355–566), (disclosed by Horiguchi) and Item 3, the GST fusion protein of cdc25B(302–566), (disclosed herein) otherwise called, GST-Xa-Gly-Ile-cdc25B (302–566). Chart 2 shows the plasmids, restrictions sites, oligonucleotide primers and portions of cdc25B sequence involved in the PCR reaction and plasmid formation. FIG. 1A and FIG. 1B, show the plasmid construction including various sites and primers. FIG. 1A is an expanded portion of the plasmid shown in FIG. 1B.

The *E. coli* can be grown in minipreps of 5 ml in LB media+ampicillin® overnight at 37 C on a shaker at a minimum of 200 RPM. 1.5 ml of the suspension of cells may be centrifuged and subjected to the reagents from the RPM kit marketed by Bio 101® designed to purify small amounts of plasmid DNA for gel analysis. Use as suggested by manufacturer. Plasmid DNA samples are digested with BamHI and XhoI for 1 hour at 37° C., and then analyzed by 0.8% agarose gel electrophoresis (1× TAE buffer). The gel is first soaked in 0.5 ug/ml ethidium bromide in 1× TAE buffer. Then the appropriate insert (0.8 kb) is excised from the agarose gel under long wavelength UV light and the DNA is isolated using the commercially available GeneClean kit (Bio 101®).

The purified DNA is then ligated into pGEX-5X-3 which has been linearized with BamHI and XhoI, and the products of the ligation are used for transformation of competent *E. coli* cells, such as JM109. The transformed *E. coli* are plated on 1% agar plates (LB media) containing ampicillin®, and grown overnight at 37 C. Positive colonies are selected and grown in 5 ml cultures of LB media+ampicillin®. After an additional 12–15 hours at 37° C., aliquots of the cultures are collected by centrifugation and subjected to an RPM plasmid isolation kit from Bio 101®.

The plasmid DNA samples are digested with BamHI and XhoI and analyzed by 0.8% agarose gel electrophoresis in 1× TAE buffer. *E. coli* cultures used to prepare the plasmid DNA samples, which are characterized by having the 0.8 kb insert piece, are either frozen at −80° C. in 10% glycerol or are grown up in LB broth at 37° C. prior to induction with IPTG. The construct to be expressed in *E. coli* is designed so that a fusion protein of GST with cdc25B (Gln 302 to Gln 566), with an intervening factor Xa cleavage site, i.e. the IEGR sequence will be produced. The resulting construct, contains IEGR, in addition to two amino acids, -Gly-Ile-, between GST and Gln$^{302}$. The -Gly-Ile- comes from the coding region contributed by part of the restriction site. See CHART 2.

From these general procedures one skilled in the art could practice this invention. The following CHARTS, Analytical Methods, Additional, Special and Optimal Conditions and Considerations are provided to better illustrate and describe but not limit this invention.

CHART 1

GST fusions. This CHART and FIG. 6, shows and compares three different fusions, The different parts of the fusions are shown in FIG. 6 as different lines in the box; a) the GST portion, labelled GST, with a straight line in the box, b) the protease cleavage site, when there is one, is shown as a dotted line in the box, labelled "P," c) the restriction site is shown as a wavey line in the box, labelled "R," and d) the cdc25B like portion is shown as a heavy line in the box, labelled "cdc25B" with the number above the box indicating DNA nucleotides and the numbers below the box indicating amino acids. The boxes are intended to suggest either DNA or protein. The boxes are not drawn to scale, the GST is relatively large, the cleavage and restriction sites relatively small and the cdc25B region has about the number of sequences indicated relative to the full length cdc25B.

Construct number one represents the fusion produced by David H. Beach and Konstantin Galaktionov, U.S. Pat. No. 5,441,880 and *Cell* (1991) 67; 1181–1194.

Construct number two represents the fusion produced by Takashi Horiguchi, et al., *Biochemical Pharmacology,* vol. 48 pp. 2139–2141, (1994).

Construct number three represents the fusion disclosed by this invention. The lines and arrows below construct number three indicates the portion of the cdc25B that becomes the active macromolecule. To improve the production of the protein as well as its stability, we engineered mutations at two sites (see vertical dashed lines below), the first of these immediately preceding nucleotide residue 1138 and protein residue 356 was made to improve the factor Xa processing of the fusion protein and the second of these, surrounding nucleotide residues 1740 and amino acid residues 556, was made to prevent undesired factor Xa cleavage of the protein at this position.

Figure 8:
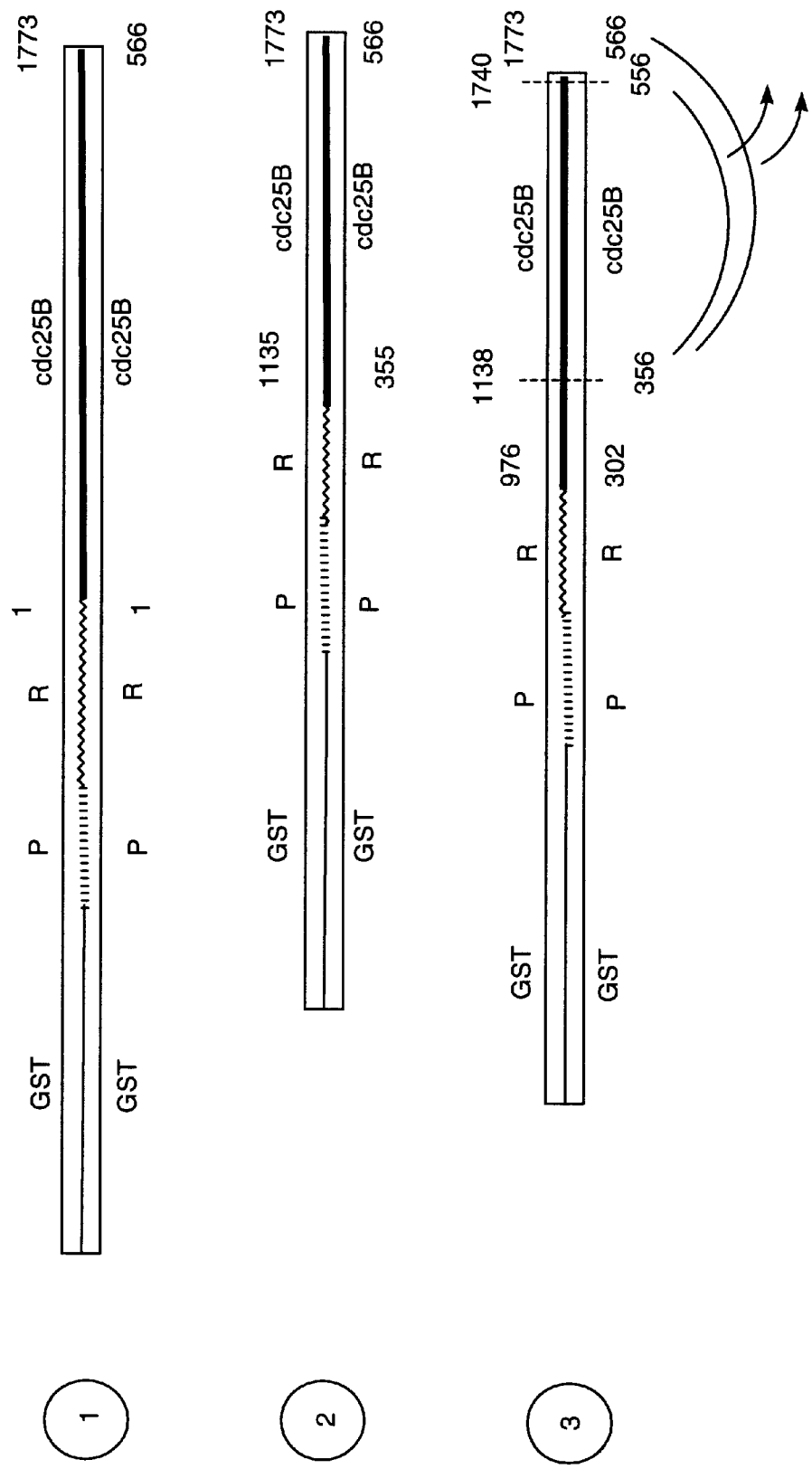
FIG. 8.

Visual images of the fusions are shown in FIG. 8.

CHART 2

This CHART shows the PCR cloning strategy and subsequent insertion of the 0.8 Kb DNA fragment into the plasmid pGEX-5X-3. Other suitable plasmids, restriction sites and biological reagents known to one skilled in the art, can be used. <u>Single underlined sequence</u> indicates PCR primers, the double arrow ↕ and <u><u>doubleunderline</u></u> indicates restriction enzymes sites, and the italicized segments show the sequence from the plasmid, in one described embodiment, the pGEX-5X-3 plasmid. The Sequence ID. Numbers, for the sequences below are provided in CHART 18. The sequences shown in this CHART show segments of longer sequences. This CHART is intended to show strategy, and details of insertion techniques, not full sequences. The dashes between sequences below indicate additional sequences not shown here, this Chart is intended to show only insertion points and cleavage sites. The sequences that are shown have been given separate Sequence Identification Numbers, SEQ. ID. NO.s, also provided in CHART 18, for the sake of completeness.

```
                              PCR Reaction

↕Bam HI

5' - GCG GATCCAGCGGCTCTTCCGCTCTC

5'-     CCAGCGGCTCTTCCGCTCTCCGTC ---- AGCCGGCTGCAGGACCAGTGA - 3'

3'-     GGTCGCCGAGAAGGCGAGAGGCAG ---- TCGGCCGACGTCCTGGTCACT - 5'

GCCGACGTCCTGGTCACTGAGCT CCG

Xho I↕  -5'
```

Sequence Identification Numbers, SEQ. ID. NO.s, for the fragments of the sequences shown, from top and left to right are as follows: SEQ. ID. NO. 30, 32, 33, 34 ard 35 (See also CHART 18).

Bam HI/Xho I Digestion Ligation into Bam HI/
Xho I Sites of pGEX-5X-3

```
                  ↕Bam HI                                      ↕Xho I

5'GAAGGTCGTGG GATC C AGCGGCTCTTCCGC ---- CAGGACCAGTGAC TCGA GCGGCCGCAT 3'

3'CTTCCAGCACC CTAG G TCGCCGAGAAGGCG ---- GTCCTGGTCACTG AGCT CGCCGGCGTA 5'

Bam HI↕                                      Xho I↕
```

Sequence Identification Numbers, SEQ. ID. NO.s, for the fragments of the sequences shown, from top and left to right are as follows: SEQ. ID. NO. 37, 38, 39, and 40 (See also CHART 18).

CHART 3

Full length human cDNA which codes for the cdc25B sequence. 2940 nucleotides in single stranded DNA are shown. Sequence disclosed by Beach and Galaktionov. This is Sequence I.D. no. 1. The coding region of the sequence is underlined, below (73–1773). The sequence below is numbered according to the Beach and Galaktionov system. This sequence was also disclosed by Nagata, who used a different numbering system. According to the Nagata numbering system, the coding sequences would be numbered 241–1941, See, Nagata A., Igarashi M., Jinno S. Suto K., and Okayama H. *New Biol.* vol. 3(10), pp. 959–68 (1991). GENBANK/S78187.

```
   1 GCCAGCTGTG CCGGCGTTTG TTGGCTGCCC TGCGCCCGGC CCTCCAGCCA
  51 GCCTTCTGCC GGCCCCGCCG CGATGGAGGT GCCCCAGCCG GAGCCCGCGC
 101 CAGGCTCGGC TCTCAGTCCA GCAGGCGTGT GCGGTGGCGC CCAGCGTCCG
 151 GGCCACCTCC CGGGCCTCCT GCTGGGATCT CATGGCCTCC TGGGGTCCCC
 201 GGTGCGGGCG GCCGCTTCCT CGCCGGTCAC CACCCTCACC CAGACCATGC
 251 ACGACCTCGC CGGGCTCGGC AGCCGCAGCC GCCTGACGCA CCTATCCCTG
 301 TCTCGACGGG CATCCGAATC CTCCCTGTCG TCTGAATCCT CCGAATCTTC
 351 TGATGCAGGT CTCTGCATGG ATTCCCCCAG CCCTATGGAC CCCCACATGG
 401 CGGAGCAGAC GTTTGAACAG GCCATCCAGG CAGCCAGCCG GATCATTCGA
 451 AACGAGCAGT TTGCCATCAG ACGCTTCCAG TCTATGCCGG TGAGGCTGCT
 501 GGGCCACAGC CCCGTGCTTC GGAACATCAC CAACTCCCAG GCGCCCGACG
 551 GCCGGAGGAA GAGCGAGGCG GGCAGTGGAG CTGCCAGCAG CTCTGGGGAA
 601 GACAAGGAGA ATGATGGATT TGTCTTCAAG ATGCCATGGA AGCCCACACA
 651 TCCCAGCTCC ACCCATGCTC TGGCAGAGTG GGCCAGCCGC AGGGAAGCCT
 701 TTGCCCAGAG ACCCAGCTCG GCCCCCGACC TGATGTGTCT CAGTCCTGAC
 751 CGGAAGATGG AAGTGGAGGA GCTCAGCCCC CTGGCCCTAG GTCGCTTCTC
 801 TCTGACCCCT GCAGAGGGGG ATACTGAGGA AGATGATGGA TTTGTGGACA
 851 TCCTAGAGAG TGACTTAAAG GATGATGATG CAGTTCCCCC AGGCATGGAG
 901 AGTCTCATTA GTGCCCCACT GGTCAAGACC TTGGAAAAGG AAGAGGAAAA
 951 GGACCTCGTC ATGTACAGCA AGTGCCAGCG GCTCTTCCGC TCTCCGTCCA
1001 TGCCCTGCAG CGTGATCCGG CCCATCCTCA AGAGGCTGGA GCGGCCCCAG
1051 GACAGGGACA CGCCCGTGCA GAATAAGCGG AGGCGGAGCG TGACCCCTCC
1101 AATCACTGTG TCACGATGAG ATCGAGAACC TCCTGGACAG TGACCACCGA
1201 GAGCTGATTG GAGATTACTC TAAGGCCTTC CTCCTACAGA CAGTAGACGG
1251 AAAGCACCAA GACCTCAAGT ACATCTCACC AGAAACGATG GTGGCCCTAT
1301 TGACGGGCAA GTTCAGCAAC ATCGTGGATA AGTTTGTGAT TGTAGACTGC
1351 AGATACCCCT ATGAATATGA AGGCGGGCAC ATCAAGACTG CGGTGAACTT
1401 GCCCCTGGAA CGCGACGCCG AGAGCTTCCT ACTGAAGAGC CCCATCGCGC
1451 CCTGTAGCCT GGACAAGAGA GTCATCCTCA TTTTCCACTG TGAATTCTCA
1501 TCTGAGCGTG GGCCCCGCAT GTGCCGTTTC ATCAGGGAAC GAGACCGTGC
1551 TGTCAACGAC TACCCCAGCC TCTACTACCC TGAGATGTAT ATCCTGAAAG
1601 GCGGCTACAA GGAGTTCTTC CCTCAGCACC CGAACTTCTG TGAACCCCAG
1651 GACTACCGGC CCATGAACCA CGAGGCCTTC AAGGATGAGC TAAAGACCTT
1701 CCGCCTCAAG ACTCGCAGCT GGGCTGGGGA GCGGAGCCGG CGGGAGCTCT
```

-continued

```
1751 GTAGCCGGCT GCAGGACCAG TGAGGGGCCT GCGCCAGTCC TGCTACCTCC
1801 CTTGCCTTTC GAGGCCTGAA GCCAGCTGCC CTATGGGCCT GCCGGGCTGA
1851 GGGCCTGCTG GAGGCCTCAG GTGCTGTCCA TGGGAAAGAT GGTGTGGTGT
1901 CCTGCCTGTC TGCCCCAGCC CAGATTCCCC TGTGTCATCC CATCATTTTC
1951 CATATCCTGG TGCCCCCCAC CCCTGGAAGA GCCCAGTCTG TTGAGTTAGT
2001 TAAGTTGGGT TAATACCAGC TTAAAGGCAG TATTTTGTGT CCTCCAGGAG
2051 CTTCTTGTTT CCTTGTTAGG GTTAACCCTT CATCTTCCTG TGTCCTGAAA
2101 CGCTCCTTTG TGTGTGTGTC AGCTGAGGCT GGGGAGAGCC GTGGTCCCTG
2151 AGGATGGGTC AGAGCTAAAC TCCTTCCTGG CCTGAGAGTC AGCTCTCTGC
2201 CCTGTGTACT TCCCGGGCCA GGGCTGCCCC TAATCTCTGT AGGAACCGTG
2251 GTATGTCTGC CATGTTGCCC CTTTCTCTTT TCCCCTTTCC TGTCCCACCA
2301 TACGAGCACC TCCAGCCTGA ACAGAAGCTC TTACTCTTTC CTATTTCAGT
2351 GTTACCTGTG TGCTTGGTCT GTTTGACTTT ACGCCCATCT CAGGACACTT
2401 CCGTAGACTG TTTAGGTTCC CCTGTCAAAT ATCAGTTACC CACTCGGTCC
2451 CAGTTTTGTT GCCCCAGAAA GGGATGTTAT TATCCTTGGG GGCTCCCAGG
2501 GCAAGGGTTA AGGCCTGAAT CATGAGCCTG CTGGAAGCCC AGCCCCTACT
2551 GCTGTGAACC CTGGGGCCTG ACTGCTCAGA ACTTGCTGCT GTCTTGTTGC
2601 GGATGGATGG AAGGTTGGAT GGATGGGTGG ATGGCCGTGG ATGGCCGTGG
2651 ATGCGCAGTG CCTTGCATAC CCAAACCAGG TGGGAGCGTT TTGTTGAGCA
2701 TGACACCTGC AGCAGGAATA TATGTGTGCC TATTTGTGTG GACAAAAATA
2751 TTTACACTTA GGGTTTGGAG CTATTCAAGA GGAAATGTCA CAGAAGCAGC
2801 TAAACCAAGG ACTGAGCACC CTCTGGATTC TGAATCTCAA GATGGGGGCA
2851 GGGCTGTGCT TGAAGGCCCT GCTGAGTCAT CTGTTAGGGC CTTGGTTCAA
2901 TAAAGCACTG AGCAAGTTGA GAAAAAAAA AAAAAAAAA
```

CHART 4

The amino acid sequence derived from the full length cdc25B DNA sequence shown in CHART 3. This is Sequence I.D. no 2.

```
  1 MEVPQPEPAP GSALSPAGVC GGAQRPGHLP GLLLGSHGLL GSPVRAAASS
 51 PVTTLTQTMH DLAGLGSRSR LTHLSLSRRA SESSLSSESS ESSDAGLCMD
101 SPSPMDPHMA EQTFEQAIQA ASRIIRNEQF AIRRFQSMPV RLLGHSPVLR
151 NITNSQAPDG RRKSEAGSGA ASSSGEDKEN DGFVFKMPMK PTHPSSTHAL
201 AEWASRREAF AQRPSSAPDL MCLSPDRKME VEELSPLALG RFSLTPEAGD
251 TEEDDGFVDI LESDLKDDDA VPPGMESLIS APLVKTLEKE EEKDLVMYSK
301 CQRLFRSPSM PCSVIRPILK RLERPQDRDT PVQNKRRRSV TPPEEQQEAE
351 EPKARVLRSK SLCHDEIENL LDSDHRELIG DYSKAFLLQT VDGKHQDLKY
401 ISPETMVALL TGKFSNIVDK FVIVDCRYPY EYEGGHIKTA VNLPLERDAE
```

```
-continued
451 SFLLKSPIAP CSLDKRVILI FHCEFSSERG PRMCRFIRER DRAVNDYPSL

501 YYPEMYILKG GYKEFFPQHP NFCEPQDYRP MNHEAFKDEL KTFRLKTRSW

551 AGERSRRELC SRLQDQ
```

CHART 5

The DNA sequence of the Cdc25B$^{976-1773}$ segment. The expected theoretical product of Factor Xa cleavage for the expressed GST fusion. This is Sequence I.D. no. 3.

```
 976                           CAGCG GCTCTTCCGC TCTCCGTCCA

1001 TGCCCTGCAG CGTGATCCGG CCCATCCTCA AGAGGCTGGA GCGGCCCCAG

1051 GACAGGGACA CGCCCGTGCA GAATAAGCGG AGGCGGAGCG TGACCCCTCC

1101 TGAGGAGCAG CAGGAGGCTG AGGAACCTAA AGCCCGCGTC CTCCGCTCAA

1151 AATCACTGTG TCACGATGAG ATCGAGAACC TCCTGGACAG TGACCACCGA

1201 GAGCTGATTG GAGATTACTC TAAGGCCTTC CTCCTACAGA CAGTAGACGG

1251 AAAGCACCAA GACCTCAAGT ACATCTCACC AGAAACGATG GTGGCCCTAT

1301 TGACGGGCAA GTTCAGCAAC ATCGTGGATA AGTTTGTGAT TGTAGACTGC

1351 AGATACCCCT ATGAATATGA AGGCGGGCAC ATCAAGACTG CGGTGAACTT

1401 GCCCCTGGAA CGCGACGCCG AGAGCTTCCT ACTGAAGAGC CCCATCGCGC

1451 CCTGTAGCCT GGACAAGAGA GTCATCCTCA TTTTCCACTG TGAATTCTCA

1501 TCTGAGCGTG GGCCCCGCAT GTGCCGTTTC ATCAGGGAAC GAGACCGTGC

1551 TGTCAACGAC TACCCCAGCC TCTACTACCC TGAGATGTAT ATCCTGAAAG

1601 GCGGCTACAA GGAGTTCTTC CCTCAGCACC CGAACTTCTG TGAACCCCAG

1651 GACTACCGGC CCATGAACCA CGAGGCCTTC AAGGATGAGC TAAAGACCTT

1701 CCGCCTCAAG ACTCGCAGCT GGGCTGGGGA GCGGAGCCGG CGGGAGCTCT

1751 GTAGCCGGCT GCAGGACCAG TGA
```

CHART 6

The peptide sequence of cdc25B$^{302-566}$ corresponding to the DNA sequence shown in CHART 5. This is Sequence I.D. no. 4

```
302  QRLFRSPSM PCSVIRPILK RLERPQDRDT PVQNKRRRSV TPPEEQQEAE

351 EPKARVLRSK SLCHDEIENL LDSDHRELIG DYSKAFLLQT VDGKHQDLKY

401 ISPETMVALL TGKFSNIVDK FVIVDCRYPY EYEGGHIKTA VNLPLERDAE

451 SFLLKSPIAP CSLDKRVILI FHCEFSSERG PRMCRFIRER DRAVNDYPSL

501 YYPEMYILKG GYKEFFPQHP NFCEPQDYRP MNHEAFKDEL KTFRLKTRSW

551 AGERSRRELC SRLQDQ
```

CHART 7

The DNA sequence of the GGG-ATC-Cdc25B$^{976-1773}$ segment. This is a notional sequence describing the expected theoretical product of Factor Xa cleavage for the expressed GST fusion, plus two codons. This is Sequence I.D. no. 5.

```
 970                        G GGATCCAGCG GCTCTTCCGC TCTCCGTCCA

1001 TGCCCTGCAG CGTGATCCGG CCCATCCTCA AGAGGCTGGA GCGGCCCCAG

1051 GACAGGGACA CGCCCGTGCA GAATAAGCGG AGGCGGAGCG TGACCCCTCC

1101 TGAGGAGCAG CAGGAGGCTG AGGAACCTAA AGCCCGCGTC CTCCGCTCAA

1151 AATCACTGTG TCACGATGAG ATCGAGAACC TCCTGGACAG TGACCACCGA

1201 GAGCTGATTG GAGATTACTC TAAGGCCTTC CTCCTACAGA CAGTAGACGG

1251 AAAGCACCAA GACCTCAAGT ACATCTCACC AGAAACGATG GTGGCCCTAT

1301 TGACGGGCAA GTTCAGCAAC ATCGTGGATA AGTTTGTGAT TGTAGACTGC

1351 AGATACCCCT ATGAATATGA AGGCGGGCAC ATCAAGACTG CGGTGAACTT

1401 GCCCCTGGAA CGCGACGCCG AGAGCTTCCT ACTGAAGAGC CCCATCGCGC

1451 CCTGTAGCCT GGACAAGAGA GTCATCCTCA TTTTCCACTG TGAATTCTCA

1501 TCTGAGCGTG GGCCCCGCAT GTGCCGTTTC ATCAGGGAAC GAGACCGTGC

1551 TGTCAACGAC TACCCCAGCC TCTACTACCC TGAGATGTAT ATCCTGAAAG

1601 GCGGCTACAA GGAGTTCTTC CCTCAGCACC CGAACTTCTG TGAACCCCAG

1651 GACTACCGGC CCATGAACCA CGAGGCCTTC AAGGATGAGC TAAAGACCTT

1701 CCGCCTCAAG ACTCGCAGCT GGGCTGGGGA GCGGAGCCGG CGGGAGCTCT

1751 GTAGCCGGCT GCAGGACCAG TGA
```

CHART 8

The peptide sequence of Gly-Ile-cdc25B$^{302-566}$ corresponding to the DNA sequence shown in CHART 7. This is a notional sequence describing the expected peptide that would be expressed from the nucleic acid sequence in CHART 7. This is Sequence I.D. no. 6.

```
300      G

301 IQRLFRSPSM PCSVIRPILK RLERPQDRDT PVQNKRRRSV TPPEEQQEAE

351 EPKARVLRSK SLCHDEIENL LDSDHRELIG DYSKAFLLQT VDGKHQDLKY

401 ISPETMVALL TGKFSNIVDK FVIVDCRYPY EYEGGHIKTA VNLPLERDAE

451 SFLLKSPIAP CSLDKRVILI FHCEFSSERG PRMCRFIRER DRAVNDYPSL

501 YYPEMYILKG GYKEFFPQHP NFCEPQDYRP MNHEAFKDEL KTFRLKTRSW

551 AGERSRRELC SRLQDQ
```

CHART 9

The DNA sequence of the ATC-GAA-GGT-CGT-GGG-ATC-Cdc25B$^{976-1773}$ segment. This is a notional sequence describing a fusion form. This is Sequence I.D. no. 7.

```
 958         ATC GAAGGTCGTG GGATCCAGCG GGTCTTCCGC TCTCCGTCCA

1001 TGCCCTGCAG CGTGATCCGG CCCATCCTCA AGAGGCTGGA GCGGCCCCAG

1051 GACAGGGACA CGCCCGTGCA GAATAAGCGG AGGCGGAGCG TGACCCCTCC

1101 TGAGGAGCAG CAGGAGGCTG AGGAACCTAA AGCCCGCGTC CTCCGCTCAA

1151 AATCACTGTG TCACGATGAG ATCGAGAACC TCCTGGACAG TGACCACCGA
```

```
-continued
1201 GAGCTGATTG GAGATTACTC TAAGGCCTTC CTCCTACAGA CAGTAGACGG

1251 AAAGCACCAA GACCTCAAGT ACATCTCACC AGAAACGATG GTGGCCCTAT

1301 TGACGGGCAA GTTCAGCAAC ATCGTGGATA AGTTTGTGAT TGTAGACTGC

1351 AGATACCCCT ATGAATATGA AGGCGGGCAC ATCAAGACTG CGGTGAACTT

1401 GCCCCTGGAA CGCGACGCCG AGAGCTTCCT ACTGAAGAGC CCCATCGCGC

1451 CCTGTAGCCT GGACAAGAGA GTCATCCTCA TTTTCCACTG TGAATTCTCA

1501 TCTGAGCGTG GGCCCCGCAT GTGCCGTTTC ATCAGGGAAC GAGACCGTGC

1551 TGTCAACGAC TACCCCAGCC TCTACTACCC TGAGATGTAT ATCCTGAAAG

1601 GCGGCTACAA GGAGTTCTTC CCTCAGCACC CGAACTTCTG TGAACCCCAG

1651 GACTACCGGC CCATGAACCA CGAGGCCTTC AAGGATGAGC TAAAGACCTT

1701 CCGCCTCAAG ACTCGCAGCT GGGCTGGGGA GCGGAGCCGG CGGGAGCTCT

1751 GTAGCCGGCT GCAGGACCAG TGA
```

CHART 10

The peptide sequence of [GST](GST not shown below)—Ile-Glu-Gly-Arg-Gly-Ile-Gln$^{302}$ . . . -Gln$^{566}$ corresponding to the DNA sequence shown in CHART 9. when combined with GST this construct would be a fusion protein. This is a notional sequence describing the expected peptide that would be expressed from the nucleic acid sequence in CHART 9. This is Sequence I.D. no. 8.

```
    IEGRG

IQRLFRSPSM PCSVIRPILK RLERPQDRDT PVQNKRRRSV TPPEEQQEAE

351 EPKARVLRSK SLCHDEIENL LDSDHRELIG DYSKAFLLQT VDGKHQDLKY

401 ISPETMVALL TGKFSNIVDK FVIVDCRYPY EYEGGHIKTA VNLPLERDAE

451 SFLLKSPIAP CSLDKRVILI FHCEFSSERG PRMCRFIRER DRAVNDYPSL

501 YYPEMYILKG GYKEFFPQHP NFCEPQDYRP MNHEAFKDEL KTFRLKTRSW

551 AGERSRRELC SRLQDQ
```

CHART 11

The peptide sequence of cdc25B$^{356-556}$ This is Sequence I.D. no. 9.

```
356      VLRSK SLCHDEIENL LDSDHRELIG DYSKAFLLQT VDGKHQDLKY

401 ISPETMVALL TGKFSNIVDK FVIVDCRYPY EYEGGHIKTA VNLPLERDAE

451 SFLLKSPIAP CSLDKRVILI FHCEFSSERG PRMCRFIRER DRAVNDYPSL

501 YYPEMYILKG GYKEFFPQHP NFCEPQDYRP MNHEAFKDEL KTFRLKTRSW

551 AGERSR
```

CHART 12

The peptide sequence of cdc25B$^{356-566}$. This is Sequence I.D. no. 10.

```
356  VLRSK SLCHDEIENL LDSDHRELIG DYSKAFLLQT VDGKHQDLKY
401 ISPETMVALL TGKFSNIVDK FVIVDCRYPY EYEGGHIKTA VNLPLERDAE
451 SFLLKSPIAP CSLDKRVILI FHCEFSSERG PRMCRFIRER DRAVNDYPSL
501 YYPEMYILKG GYKEFFPQHP NFCEPQDYRP MNHEAFKDEL KTFRLKTRSW
551 AGERSRRELC SRLQDQ
```

CHART 13

(Advance Form—Nucleotide—Design)

This CHART contains sequences disclosed under the section of this invention entitled, "Advanced Forms of the Macromolecule." There are eight different sequences disclosed in this section of the document, including both amino acid and nucleotide sequences. One construct described is the same construct described previously, in CHART 5 (nucleotide, Seq. ID. No. 3) and in CHART 6 (peptide, SEQ. ID. No. 4). Four of the constructs are from the Design section and four from the Results section. The sequences from the 3 Design constructs, nucleotide, from the Advanced Forms, are provided in this CHART, below.

First, the DNA sequence of the Cdc25B$^{976-1773}$ segment, from CHART 5 is provided, and then as modified according to the section, Advanced Forms of the Macromolecule. The CHART 5, sequence is provided, then the three forms, Mutein1, Mutein2, and Mutein3 are shown with the appropriate substitutions shown below the original sequence. All other sequences remain the same as in the original sequence, except where shown as changed below, i.e, dots (.) below indicate no changes. The Sequence ID No. for the original sequence is SEQ. ID. No. 3. The Mutein1 SEQ. ID. No. is No. 11. The Mutein2 SEQ. ID. No. is No. 12. The Mutein3 SEQ. ID. No. is No. 13.

```
    976     (from CHART 5)                      CAGCG GCTCTTCCGC TCTCCGTCCA
Mutein1                                         ..... .......... ..........
Mutein2                                         ..... .......... ..........
Mutein3                                         ..... .......... ..........

1001     TGCCCTGCAG CGTGATCCGG CCCATCCTCA AGAGGCTGGA GCGGCCCCAG
Mutein1     .......... .......... .......... .......... ..........
Mutein2     .......... .......... .......... .......... ..........
Mutein3     .......... .......... .......... .......... ..........

1051     GACAGGGACA CGCCCGTGCA GAATAAGCGG AGGCGGAGCG TGACCCCTCC
Mutein1     .......... .......... .......... .......... ..........
Mutein2     .......... .......... .......... .......... ..........
Mutein3     .......... .......... .......... .......... ..........

1101     TGAGGAGCAG CAGGAGGCTG AGGAACCTAA AGCCCGCGTC CTCCGCTCAA
Mutein1     .......... .......... .....AT.G. ...G...... ..........
Mutein2     .......... .......... .......... .......... ..........
Mutein3     .......... .......... .....AT.G. ...G...... ..........

1151     AATCACTGTG TCACGATGAG ATCGAGAACC TCCTGGACAG TGACCACCGA
Mutein1     .......... .......... .......... .......... ..........
Mutein2     .......... .......... .......... .......... ..........
Mutein3     .......... .......... .......... .......... ..........

1201     GAGCTGATTG GAGATTACTC TAAGGCCTTC CTCCTACAGA CAGTAGACGG
Mutein1     .......... .......... .......... .......... ..........
Mutein2     .......... .......... .......... .......... ..........
Mutein3     .......... .......... .......... .......... ..........

1251     AAAGCACCAA GACCTCAAGT ACATCTCACC AGAAACGATG GTGGCCCTAT
Mutein1     .......... .......... .......... .......... ..........
Mutein2     .......... .......... .......... .......... ..........
Mutein3     .......... .......... .......... .......... ..........

1301     TGACGGGCAA GTTCAGCAAC ATCGTGGATA AGTTTGTGAT TGTAGACTGC
Mutein1     .......... .......... .......... .......... ..........
Mutein2     .......... .......... .......... .......... ..........
Mutein3     .......... .......... .......... .......... ..........

1351     AGATACCCCT ATGAATATGA AGGCGGGCAC ATCAAGACTG CGGTGAACTT
Mutein1     .......... .......... .......... .......... ..........
Mutein2     .......... .......... .......... .......... ..........
Mutein3     .......... .......... .......... .......... ..........

1401     GCCCCTGGAA CGCGACGCCG AGAGCTTCCT ACTGAAGAGC CCCATCGCGC
Mutein1     .......... .......... .......... .......... ..........
```

```
                       -continued
Mutein2    ..........  ..........  ..........  ..........  ..........
Mutein3    ..........  ..........  ..........  ..........  ..........

1451       CCTGTAGCCT  GGACAAGAGA  GTCATCCTCA  TTTTCCACTG  TGAATTCTCA
Mutein1    ..........  ..........  ..........  ..........  ..........
Mutein2    ..........  ..........  ..........  ..........  ..........
Mutein3    ..........  ..........  ..........  ..........  ..........

1501       TCTGAGCGTG  GGCCCCGCAT  GTGCCGTTTC  ATCAGGGAAC  GAGACCGTGC
Mutein1    ..........  ..........  ..........  ..........  ..........
Mutein2    ..........  ..........  ..........  ..........  ..........
Mutein3    ..........  ..........  ..........  ..........  ..........

1551       TGTCAACGAC  TACCCCAGCC  TCTACTACCC  TGAGATGTAT  ATCCTGAAAG
Mutein1    ..........  ..........  ..........  ..........  ..........
Mutein2    ..........  ..........  ..........  ..........  ..........
Mutein3    ..........  ..........  ..........  ..........  ..........

1601       GCGGCTACAA  GGAGTTCTTC  CCTCAGCACC  CGAACTTCTG  TGAACCCCAG
Mutein1    ..........  ..........  ..........  ..........  ..........
Mutein2    ..........  ..........  ..........  ..........  ..........
Mutein3    ..........  ..........  ..........  ..........  ..........

1651       GACTACCGGC  CCATGAACCA  CGAGGCCTTC  AAGGATGAGC  TAAAGACCTT
Mutein1    ..........  ..........  ..........  ..........  ..........
Mutein2    ..........  ..........  ..........  ..........  ..........
Mutein3    ..........  ..........  ..........  ..........  ..........

1701       CCGCCTCAAG  ACTCGCAGCT  GGGCTGGGGA  GCGGAGCCGG  CGGGAGCTCT
Mutein1    ..........  ..........  ..........  ..........  ..........
Mutein2    ..........  ..........  ..........  .......AA.  AA........
Mutein3    ..........  ..........  ..........  .......AA.  AA........

1751       GTAGCCGGCT  GCAGGACCAG  TGA
Mutein1    ..........  ..........  ...
Mutein2    ..........  ..........  ...
Mutein3    ..........  ..........  ...
```

CHART 14

(Advance Form—Peptides—Design)

This CHART contains sequences disclosed under the section of this invention entitled, "Advanced Forms of the Macromolecule." There are several different constructs disclosed in this section of the document, both amino acid and nucleotides are disclosed. Three CHARTS are devoted to this section. This CHART is from the "DESIGN" section of Advanced Forms of the Macromolecule. It is followed by two CHARTS from the "RESULTS" portion of the same section (nucleotide-CHART 15 and peptide-CHART 16). This CHART only includes amino acid residues, it does not include restriction sites, protease cleavage sites or the GST fusion portion of the fusion molecules. The first, sequence described is described previously, in CHART 6. (peptide, SEQ. ID. No. 4). Four of the constructs are from the Design section and four from the Results section. The sequences from the 3 Design constructs, peptides, from the Advanced Forms, are provided in this CHART, below. The following CHART, CHART 15 provides the corresponding nucleotide sequences, beginning with the sequence first disclosed in CHART 5 (nucleotide, Seq. ID. No. 3).

In the sequence below, the peptide sequence of the Cdc25B$^{302-566}$ segment, from CHART 6 is provided, and then as modified according to the section, Advanced Forms of the Macromolecule. The CHART 6, sequence is provided, then the three forms: Mutein1, Mutein2, and Mutein3 are show with the appropriate substitutions shown below the original sequence. All other sequences remain the same as in the original sequence, except where shown as changed below, i.e. dots (.) below indicate no changes. The Sequence ID No. for the original sequence is SEQ. ID. No. 4. The Mutein1 SEQ. ID. No. is No. 14. The Mutein2 SEQ. ID. No. is No. 15. The Mutein3 SEQ. ID. No. is No. 16.

```
302       -QRLFRSPSM  PCSVIRPILK  RLERPQDRDT  PVQNKRRRSV  TPPEEQQEAE
Mutein1   -.........  ..........  ..........  ..........  ..........
Mutein2   -.........  ..........  ..........  ..........  ..........
Mutein3   -.........  ..........  ..........  ..........  ..........

351       EPKARVLRSK  SLCHDEIENL  LDSDHRELIG  DYSKAFLLQT  VDGKHQDLKY
Mutein1   .IEG......  ..........  ..........  ..........  ..........
Mutein2   ..........  ..........  ..........  ..........  ..........
Mutein3   .IEG......  ..........  ..........  ..........  ..........

401       ISPETMVALL  TGKFSNIVDK  FVIVDCRYPY  EYEGGHIKTA  VNLPLERDAE
Mutein1   ..........  ..........  ..........  ..........  ..........
Mutein2   ..........  ..........  ..........  ..........  ..........
Mutein3   ..........  ..........  ..........  ..........  ..........

451       SFLLKSPIAP  CSLDKRVILI  FHCEFSSERG  PRMCRFIRER  DRAVNDYPSL
```

```
         -continued
Mutein1  .........  ..........  ..........  ..........  ..........
Mutein2  .........  ..........  ..........  ..........  ..........
Mutein3  .........  ..........  ..........  ..........  ..........

501      YYPEMYILKG GYKEFFPQHP  NFCEPQDYRP  MNHEAFKDEL  KTFRLKTRSW
Mutein1  .........  ..........  ..........  ..........  ..........
Mutein2  .........  ..........  ..........  ..........  ..........
Mutein3  .........  ..........  ..........  ..........  ..........

551      AGERSRRELC SRLQDQ
Mutein1  .........  ......
Mutein2  .....KK... ......
Mutein3  .....KK... ......
```

CHART 15

(Advance Form—Nucleotide—Results)

This CHART presents the 4 nucleotide sequences from the RESULT section of Advanced Forms of the Macromolecule. This CHART only includes nucleic acid residues, it does not include restriction sites, protease cleavage sites or the GST fusion portion of the fusion molecules.

The previous CHART 14 described the DESIGN section and CHARTS 15 and 16 describe residues from constructs from the RESULTS section of this portion of the invention.

First the DNA sequence of the $Cdc25B^{1138-1740}$ and $Cdc25B^{1138-1773}$ segments are provided as modified according to the section, Advanced Forms of the Macromolecule. The three forms: Mutein1, Mutein2, and Mutein3, are shown with the appropriate substitutions shown below the full sequence. All other sequences remain the same as in the full sequence, except where shown as changed below, i.e. dots (.) below indicate no changes. The Sequence ID No. for the wild type sequence of $Cdc25B^{976-1773}$ segment, is SEQ. ID. No. 17. The Mutein1 SEQ. ID. No. is No. 18. The Mutein2 SEQ. ID. No. is No. 19. The Mutein3 SEQ. ID. No. is No. 20.

```
1138                                                   GTC CTCCGCTCAA
Mutein1                                                ... ..........
Mutein2                                                ... ..........
Mutein3                                                ... ..........

1151     AATCACTGTG TCACGATGAG ATCGAGAACC TCCTGGACAG TGACCACCGA
Mutein1  .........  ..........  ..........  ..........  ..........
Mutein2  .........  ..........  ..........  ..........  ..........
Mutein3  .........  ..........  ..........  ..........  ..........

1201     GAGCTGATTG GAGATTACTC TAAGGCCTTC CTCCTACAGA CAGTAGACGG
Mutein1  .........  ..........  ..........  ..........  ..........
Mutein2  .........  ..........  ..........  ..........  ..........
Mutein3  .........  ..........  ..........  ..........  ..........

1251     AAAGCACCAA GACCTCAAGT ACATCTCACC AGAAACGATG GTGGCCCTAT
Mutein1  .........  ..........  ..........  ..........  ..........
Mutein2  .........  ..........  ..........  ..........  ..........
Mutein3  .........  ..........  ..........  ..........  ..........

1301     TGACGGGCAA GTTCAGCAAC ATCGTGGATA AGTTTGTGAT TGTAGACTGC
Mutein1  .........  ..........  ..........  ..........  ..........
Mutein2  .........  ..........  ..........  ..........  ..........
Mutein3  .........  ..........  ..........  ..........  ..........

1351     AGATACCCCT ATGAATATGA AGGCGGGCAC ATCAAGACTG CGGTGAACTT
Mutein1  .........  ..........  ..........  ..........  ..........
Mutein2  .........  ..........  ..........  ..........  ..........
Mutein3  .........  ..........  ..........  ..........  ..........

1401     GCCCCTGGAA CGCGACGCCG AGAGCTTCCT ACTGAAGAGC CCCATCGCGC
Mutein1  .........  ..........  ..........  ..........  ..........
Mutein2  .........  ..........  ..........  ..........  ..........
Mutein3  .........  ..........  ..........  ..........  ..........

1451     CCTGTAGCCT GGACAAGAGA GTCATCCTCA TTTTCCACTG TGAATTCTCA
Mutein1  .........  ..........  ..........  ..........  ..........
Mutein2  .........  ..........  ..........  ..........  ..........
Mutein3  .........  ..........  ..........  ..........  ..........

1501     TCTGAGCGTG GGCCCCGCAT GTGCCGTTTC ATCAGGGAAC GAGACCGTGC
Mutein1  .........  ..........  ..........  ..........  ..........
Mutein2  .........  ..........  ..........  ..........  ..........
Mutein3  .........  ..........  ..........  ..........  ..........

1551     TGTCAACGAC TACCCCAGCC TCTACTACCC TGAGATGTAT ATCCTGAAAG
Mutein1  .........  ..........  ..........  ..........  ..........
```

```
                       -continued
Mutein2   ..........  ..........  ...........  ...........  ..........
Mutein3   ..........  ..........  ...........  ...........  ..........

1601      GCGGCTACAA  GGAGTTCTTC  CCTCAGCACC   CGAACTTCTG   TGAACCCCAG
Mutein1   ..........  ..........  ...........  ...........  ..........
Mutein2   ..........  ..........  ...........  ...........  ..........
Mutein3   ..........  ..........  ...........  ...........  ..........

1651      GACTACCGGC  CCATGAACCA  CGAGGCCTTC   AAGGATGAGC   TAAAGACCTT
Mutein1   ..........  ..........  ...........  ...........  ..........
Mutein2   ..........  ..........  ...........  ...........  ..........
Mutein3   ..........  ..........  ...........  ...........  ..........

1701      CCGCCTCAAG  ACTCGCAGCT  GGGCTGGGGA   GCGGAGCCGG   (stops)
Mutein1   ..........  ..........  ...........  ...........  (stops)
Mutein2   ..........  ..........  ...........  .......AA.   AAGGAGCTCT
Mutein3   ..........  ..........  ...........  .......AA.   AA........

1751
Mutein2   GTAGCCGGCT  GCAGGACCAG  TGA
Mutein3   ..........  ..........  ...
```

CHART 16

(Advance Form—Peptide—Results)

This CHART presents the 4 peptide sequences from the RESULTS section of the invention, Advanced Forms of the Macromolecule. This CHART only includes amino acid residues, it does not include restriction sites, protease cleavage sites or the GST fusion portion of the fusion molecules. This CHART provides the amino acid residues that correspond to the nucleic acid residues provided in CHART 15.

First the peptide sequence of the Cdc25B$^{356-566}$ segment sequence is provided, and then as modified according to the section, Advanced Forms of the Macromolecule. The wild type sequence is provided, then three forms: Mutein1, Mutein2, and Mutein3, are provided with the appropriate substitutions shown below the original sequence. All other sequences remain the same as in the original sequence, except where shown as changed below, i.e. dots (.) below indicate no changes. The Sequence ID No. for the original sequence is SEQ. ID. No. 9. The Mutein1 SEQ. ID. No. is No. 21. The Mutein2 SEQ. ID. No. is No. 22. The Mutein3 SEQ. ID. No. is No. 23.

CHART 17

This CHART contains 2 sequences disclosed in the part of the document relating to cdc25B constructs having similarity to human VHR phosphatase, titled VHR-LIKE CONSTRUCT7S. Full length human cdc25B was previously provided in CHART 3, it also appears in VHR-Like-CHART A. The underlined portion of VHR-Like-CHART A shows the VHR like construct which is provided here in CHART 17, PART A. This construct is made into a GST fusion construct, the GST the GST and GIQ are shown in parenthesis. The body of the construct begins with residue 364 and ends with residue 529, as shown in VHR-Like-CHART A. The Part A sequence, without (GST)-(Xa)-(GIQ) is Sequence ID No. 24.

Also shown in this CHART 17, Part B. is the amino acid sequence of human VHR phosphatase, as disclosed in, Ishibashi T., Bottaro D. P., Michieli P., Kelley C. A., Aaronson S. A., "A novel dual specificity phosphatase induced by serum stimulation and heat shock," *J. Biol. Chem.*, vol. 269(47), pp. 29897–902 (1994). The Part B sequence is SEQ. IE, NO. 25

```
356       VLRSK  SLCHDEIENL  LDSDHRELIG  DYSKAFLLQT  VDGKHQDLKY
Mutein1   .....  ..........  ..........  ..........  ..........
Mutein2   .....  ..........  ..........  ..........  ..........
Mutein3   .....  ..........  ..........  ..........  ..........

401       ISPETMVALL  TGKFSNIVDK  FVIVDCRYPY  EYEGGHIKTA  VNLPLERDAE
Mutein1   ..........  ..........  ..........  ..........  ..........
Mutein2   ..........  ..........  ..........  ..........  ..........
Mutein3   ..........  ..........  ..........  ..........  ..........

451       SFLLKSPIAP  CSLDKRVILI  FHCEFSSERG  PRMCRFIRER  DRAVNDYPSL
Mutein1   ..........  ..........  ..........  ..........  ..........
Mutein2   ..........  ..........  ..........  ..........  ..........
Mutein3   ..........  ..........  ..........  ..........  ..........

501       YYPEMYILKG  GYKEFFPQHP  NFCEPQDYRP  MNHEAFKDEL  KTFRLKTRSW
Mutein1   ..........  ..........  ..........  ..........  ..........
Mutein2   ..........  ..........  ..........  ..........  ..........
Mutein3   ..........  ..........  ..........  ..........  ..........

551       AGERSR (stops at 556)
Mutein1   ...... (stops at 556)
Mutein2   .....KKELC  SRLQDQ
Mutein3   .....KKELC  SRLQDQ
```

CHART 17, PART A

```
364 (GST)-(Xa)-(GIQ)-HDEIENL LDSDHRELIG DYSKAFLLQT VDGKHQDLKY
401      ISPETMVALL TGKFSNIVDK FVIVDCRYPY EYEGGHIKTA VNLPLERDAE
451      SFLLKSPIAP CSLDKRVILI FHCEFSSERG PRMCRFIRER DRAVNDYPSL
501      YYPEMYILKG GYKEFFPQHP NFCEPQDYR
```

CHART 17 PART B

```
  1      MSGSFELSVQ DLNDLLSDGS GCYSLPSQPC NEVTPRIYVG NASVAQDIPK
 51      LQKLGITHVL NAAEGRSFMH VNTNANFYKD SGITYLGIKA NDTQEFNLSA
101      YFERAADFID QALAQKNGRV LVHCREGYSR SPTLVIAYLM MRQKMDVKSA
151      LSIVRQNREI GPNDGFLAQL CQLNDRLAKE GKLKP
```

CHART 18

This CHART contains other miscellaneous sequences disclosed with this invention.

From FIG. 1A: The DNA sequences shown before the 0.8 Kb cdc25B insert are: ATC-GAA-GGT-CGT-GGG-ATC-C (Sequence I.D. no. 26) corresponding to the following amino acids: Ile-Glu-Gly-Arg-Gly-Ile-. (Sequence I.D. no. 27.)

From FIG. 1A: The sequences shown after the 0.8 Kb cdc25B insert are:
C-TCG-AGC-GGC-CGC-ATC-GTG-ACT-GAC-TGA- (Sequence I.D. no. 28.) corresponding to the following amino acids: Ser-Ser-Gly-Arg-Ile-Val-Thr-Asp. (Sequence I.D. no. 29.)

Disclosed as a primers ordered from Genosys® are:
Geno-I is -GCG GAT CCA GCG GCT CTT CCG CTC TC (5'→3') (Sequence I.D. no. 30.) and Geno-II is - GCC TCG AGT CAC TGG TCC TGC AGC CG (5'→3') (Sequence I.D. no. 31.)

The following sequences were disclosed from CHART 2: The top part of CHART 2 started with PCR Reaction and showed:
- <u>GCG GATCCAGCGGCTCTTCCGCTCTC</u> (5'→3') (Sequence I.D. no. 30, repeated from just above.)
- CCAGCGGCTCTTCCGCTCTCCGTC— (5'→3') (Sequence I.D. no. 32.)
—AGCCGGCTGCAGGACCAGTGA- (5'→3') (Sequence I.D. no. 33.)
- GGTCGCCGAGAAGGCGAGAGGCAG— (3'→5') (This sequence is entered in (5'→3') direction as Sequence I.D. no. 34.)
—TCGGCCGACGTCCTGGTCACT- (3'→5') (This sequence is entered in (5'→3') direction as Sequence I.D. no. 35.)
<u>GCCGACGTCCTGGTCACTGAGCT</u> CCG- (3'→5') (This sequence is entered in (5'→3') direction as Sequence I.D. no. 36.)

The bottom part of CHART 2 had Bam HI/Xho I Digestion and Ligation into Bam HI/Xho I sites of pGEX-5X-3 and showed:
- GAAGGTCGTG<u>G GATCC</u> AGCGGCTCTTCCGC— (5'→3') (Sequence I.D. no. 37.)
—CAGGACCAGTGA<u>C TCGA G</u>CGGCCGCAT- (5'→3') (Sequence I.D. no. 38.)
- CTTCCAGCAC<u>C CTAGG</u> TCGCCGAGAAGGCG— (3'→5') (This sequence is entered in (5'→3') direction as Sequence I.D. no. 39.)
—GTCCTGGTCACT<u>G AGCT</u> CGCCGGCGTA- (3'→5') (This sequence is entered in (5'→3') direction as Sequence I.D. no. 40.)

There were several minor sequences disclosed in the section of the invention titled, Advanced Forms of the Macromolecule. The following oligonucleotide primers are mentioned:

- GCG GAG GAC GCG GCC TTC AAT TTC CTC AGC CTC - (5'→3') (Sequence ID No. 41.)
- GGG GAG CGG AGC AAG AAG GAG CTC TGT AGC - (5'→3') (Sequence ID No. 42.)
- GAG GCT GAG GAA ATT GAA GGC CGC GTC CTC CGC - (5'→3') (Sequence ID No. 43
- GCG GAG GAC GCG GCC TTC AAT TTC CTC AGC CTC - (5'→3') (Sequence ID No. 41, repeated from just above.)

There are several minor sequences disclosed in the VHR-LIKE CONSTRUCT portion of this document, relating to VHR like domains, the following two DNA primers, listed in a 5'→3' orientation were prepared/obtainded from Genosys®:
-GCG GAT CCA GCA CGA TGA GAT CGA GAA-. (Geno-III) (Sequence ID No. 44.)
and -GCC TCG AGT CAC CGG TAG TCC TGG GGT- (Geno-IV) (Sequence ID No. 45.)

Analytical Methods

Electrophoresis—One-dimensional analytical SDS polyacrylamide gel electrophoresis was conducted using 10% gels in a mini Protean II system (Bio-Rad Laboratories) according to the method of Laemmli. See, Laemmli, *Nature* (1970) 227: 680–685, "Cleavage of structural proteins during the assembly of the head of bacteriophage T4". Samples were diluted with 1 volume of denaturation buffer (2% SDS, 25% glycerol, 0.25 M Tris HCl, pH 6,8, and 1% beta-mercaptoethanol), and heated for at least 2 minutes in a boiling water bath. Electrophoresis was conducted at constant power (5 watts/gel) for 1 hour at room temperature and terminated when the dye front (bromphenol blue) reached the bottom of the gel. The completed gels were fixed in 50% ethanol and 10% acetic acid, and stained with Coomassie Brilliant Blue G-250. Alternatively, proteins in the gels were electroblotted onto PVDF.

Western blotting—Transferred blots were blocked with 2% non-fat dried milk in PBS for 5 min. After washing in tris buffered saline [TBS (10 mM Tris HCl, 150 mM NaCl, pH 7.5)] for 5 min, blots were incubated with primary antibody, (rabbit anti-cdc25B polyclonal antibody) for 1 hr on an orbital shaker. The blots were washed in 0.05% Tween 20 in TBS for 5 min followed by a 5 min wash with TBS. The processed blots were incubated in TBS with 1% BSA and 1:2000 dilution of anti-rabbit FC alkaline phosphatase conjugate (Promega) for 1 hr. After washing as described above, color was developed using BCIP/NBT as substrates for alkaline phosphatase. This reaction vias stopped by rinsing in deionized water, blots were air dried, and stored.

Sequence analysis—Amino terminal sequencing of purified cdc25B proteins was performed on an ABI 476A protein sequencer. Database searches were conducted using the Genetics Computer Group software package (GCG). The amino acid sequences of several homologous proteins were examined by the program FASTA.

Enzyme assay and Kinetic Analyses—Assays of PNPP hydrolase activity associated with cdc25B are conducted using the reagents described by Horiguchi et al. (*Biochemical Pharmacology*, Vol. 48 pp. 2139–2141, (1994)). These reagents include (as final concentrations in 125 ul): 25 mM Hepes, pH 8.0, 10 mM DTT, 0.1 mg/ml bovine serum albumin, and variable concentrations of pNPP. For assays where a single concentration )f substrate is used at saturation, we customarily use a final concentration of 20 mM pNPP. Assay solution is prepared in a final volume of 100 ul, including the addition of freshly prepared dithiothreitol. At the initiation of the assay, 25 ul of enzyme is added with mixing, and a continuous recording of absorbances at 405 nm is completed over a short time period. For the determination of $K_m$ and $V_{max}$, multiple pNPP concentrations are used at a constant enzyme concentration. Rates at each concentration of substrate are determined and the $K_m$ and $V_{max}$ calculated from fine fitting to a Michaelis Menten equation. The extinction coefficient (1 mil=17.8 absorbance units at 405 nm) for the p-nitrophenyl product has been previously published. See, N. K. Tonks, C. D. Diltz, and E. H. Fischer (1988) *J. Biol. Chem.* 263: 6731–6737. The velocity of the reaction is defined as follows: One unit of activity is defined as nmoles of pNPP hydrolyzed per minute per milligram of enzyme protein at 25° C.

Combining the methods, procedures and analytic tools above with expression and purification procedures generally known to one skilled in the art, the following sequences are created:

(Form I) Fusion protein is,
  GST-Ile-Glu-Gly-Arg-Gly-Ile-Gln$^{302}$ . . . -Gln$^{566}$.
(Form II) Final product of cdc25B after factor Xa treatment is,
  Val$^{356}$ . . . -Arg$^{556}$.

Additional, Special and Optimal Conditions and Considerations

Attempts to utilize factor Xa cleavage using solution phase digestion (i.e., displacing GST-Xa-Gly-Ile-cdc25B from a glutathione Sepharose column with reduced glutathione prior to digestion) were shown to be unsuitable. Protein prepared in this way was contaminated with the glutathione S-transferase (GST) protein component, and subsequent purification procedures are unable to purify the cdc25B away from the GST polypeptide and any fragmentation products of GST-containing polypeptides.

Most, if not all of the GST-Xa-Gly-Ile-cdc25B (302–566) fusion protein is soluble in the extraction/lysis system. The method generally used to screen for all produced cdc25B proteins was Western blotting using a commercially available anti-murine cdc25B polyclonal antibody, which recognizes C-terminal residues 547–566 of human cdc25B.

Both DnaK and GroEL, bacterial chaperoning having polypeptide sizes of about 70 and about 60 kD respectively, are associated with the cdc25B protein and/or to the peptide tether between the GST and cdc25B polypeptides. This observation is made during the factor Xa cleavage step since these proteins are found together with the truncated cdc25B protein in the eluate. A recent observation by Silva et al., using a similar art, showed conclusively that DNA-K did not bind to the GST component of a GST-protein fusion construct. N. L. C. L. Silva, R. S. Haworth, D. Singh, and L. Fliegel, "The carboxyl-terminal region of the Na/H exchanger interacts with mammalian heat shock protein", *Biochemistry* 34: 10412–10420 (1995). Both chaperonins, DnaK and GroEL, are resolved from the truncated cdc25B protein by the Q fast flow ion exchange step. Both DnaK and GroEL may be required for both solubility and correct folding of the truncated cdc25B in the *E. coli* expression system.

Additional references and descriptions of DnaK and GroEL are provided below and incorporated by :reference:

R. Hlodan, P. Tempst, and F. U. Hartl, "Binding of defined regions of a polypeptide to GroEL and its implications for chaperonin-mediated protein folding", *Nature Structural Biology*, vol. 2, pp. 587–595 (1995).

A. M. Fourie, J. F. Sambrook, and M -J H. Gething, "Common and divergent peptide binding specificities of hsp70 molecular chaperones", *J. Biol. Chem.*, vol. 269, pp. 30470–30478 (1994).

J. Wild, E. Altman, T. Yura, and C. A. Gross, "DnaK and DnaJ heat shock proteins participate in protein export in *Escherichia coli*", *Genes and Development*, vol. 6, pp. 1165–1172 (1992) and E. A. Craig, "Chaperones: helpers along the pathways to protein folding", *Science*, vol. 260, pp. 1902–1903 (1993).

L. S. Itzhaki, D. E. Otzen, and A. R. Fersht, "Nature and consequences of GroEL-protein interactions", *Biochemistry*, vol. 34, pp. 14581–14587 (1995).

GST remains bound to the glutathione column matrix during factor Xa cleavage as determined by Western blotting of eluates using a commercially available rabbit anti-GST polyclonal antibody.

Additional cleavage sites downstream from the engineered factor Xa site were observed. A predominant secondary site was observed at residue 355 (Arg), which appears to be the minimal domain defined by factor Xa cleavage. Digestion of the GST-cdc25B construct yields a minimal catalytic domain defined by the sequence of valine 356 through arginine 556. Due to a large number of arginine residues in the region between residues 302 and 356, accessory factor Xa cleavage sites are recognized during production. Another secondary factor Xa site is found between Arg$^{556}$ and Arg$^{557}$, near the C-terminus of cdc25B. Others have reported on the ability of factor Xa to cleave at arginines other than in the IEGR motif. See, R. Lottenberg, J. A. Hall, E. Pautler, A. Zupan, U. Christensen, and C. M. Jackson, "The action of factor Xa on peptide p-nitroanilide subtrates: substrate selectivity and examination of hydrolysis with different reaction conditions", *Biochem. Biophys. Acta* 874: 326–336 (1986).

Factor Xa protein and activity is easily removed after the digestion step by the Mono Q ion exchange chromatography step. The activity is separated with baseline resolution from the cdc25B protein. However; for work requiring high cdc25B concentrations after this step, we routinely add APMSF and/or pefabloc (serine protease inhibitors) to the cdc25B preparation after the Mono Q step. The complete removal of detectable protease activity is validated using an assay for factor Xa. The substrate for this reaction is N-p-tosyl-Gly-Pro-Arg-p-nitroanilide. See, by R. Lottenberg et al., Biochem. Biophys. Acta 874: 326–336 (1986).

The method by which a bound GST fusion protein containing the desired protein partner is cleaved by factor Xa while still bound to the glutathione resin is also detailed in the Pharmacia Biotech® protocol booklet for pGEX vector expression ("GST Gene Fusion System, 2nd Edition, Revision 2, Pharmacia Biotech®, p. 17–18, 1996).

Activity and Usefulness of the Macro Molecules

The following macromolecules, or constructs of cdc25B, were observed.

Form I is a fusion protein whose sequence is:
GST-Ile-Glu-Gly-Arg-Gly-Ile-Gln$^{302}$ . . . -Gln$^{566}$. See, CHART 10, SEQ. ID NO. 8

Form II is the final product of cdc25B after factor Xa cleavage,
Val$^{356}$- . . . -Arg$^{556}$. See, CHART 11, SEQ. ID. NO. 9

Reversible inhibitors of single-site monomeric enzymes generally exert their effects over an approximately 100-fold concentration range. Thus, if a given inhibitor concentration results in a 10% inhibition of an enzymatic reaction, then increasing the inhibitor concentration by two orders of magnitude will result in a 90% inhibition of the reaction. This is true for competitive, noncompetitive, and uncompetitive inhibitors. See, Cheng, Y. -C. and Prusoff, W. H. (1973) Relationship between the inhibitor constant ($K_i$) and the concentration of inhibitor which causes 50 per cent inhibition ($I_{50}$) of an enzymatic reaction. *Biochemical Pharmacology* Vol. 22, pp. 3099–3108.

Performing the necessary kinetic experiments and data analysis which distinguish between these three classes of enzyme inhibitors is usually straightforward. When an inhibitor exerts its effects over a concentration range smaller than 100-fold the effect is said to be cooperative. Cooperativity occurs in multimeric enzymes and in monomeric enzymes containing multiple binding sites. Many compounds which reversibly inhibit GST-cdc25B fusion proteins do so in a cooperative manner. Because of the added ambiguity in terms of possible kinetic mechanisms and added mathematical complexity which results from cooperativity, it is often impossible to characterize the kinetic mechanism by which such inhibitors exert their effects. This is particularly true if the enzyme under investigation is a synthetic fusion protein and the enzyme portion is normally monomeric and contains only a single known binding site, as is the case with the catalytic domain of cdc25B. With near full length cdc25B (GST-cdc25B (31–566), observed cooperativity is probably the result of dimer or higher oligomer formation caused by the GST domain, which is known to form homodimers. The cooperativity seen with inhibitors of GST-cdc25B are absent in inhibitors of minimal domain cdc25B (cdc25B (356–556)). In other words, inhibitors which act in a cooperative manner toward near full length GST-cdc25B often act as competitive inhibitors toward the minimal domains or catalytic macromolecules of cdc25B and they exhibit few cooperative effects.

Figure 2:
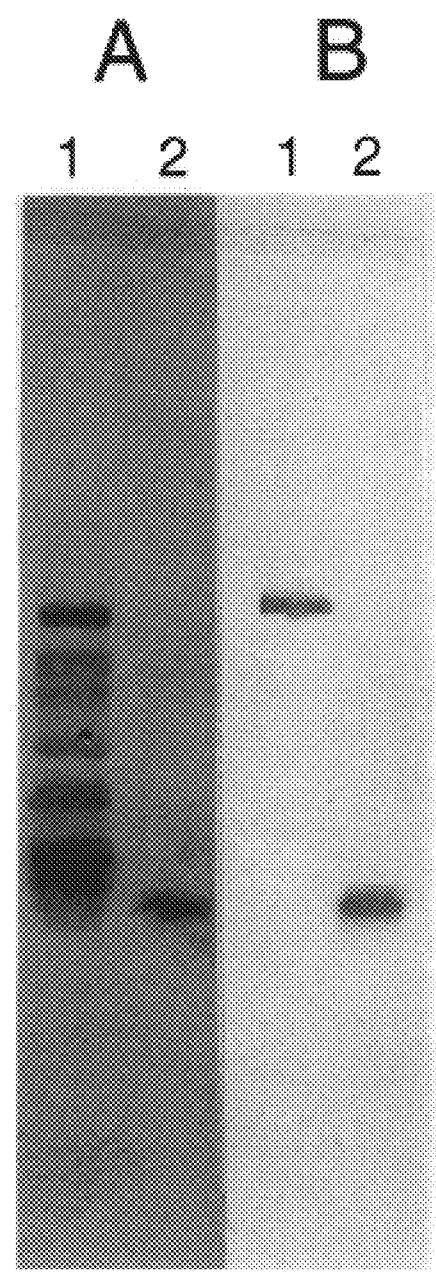
FIG. 2 shows a western blot in two sections. The section on the left (A), represents a Coomassie Blue stained PVDF-P blot and the section on the right (B) represents a rabbit anti-cdc25B probing of the same blot. Columns one (1) show GST-cdc25B(31–566) and columns two (2) show the special domain cdc25B (356–556).
Figure 3:
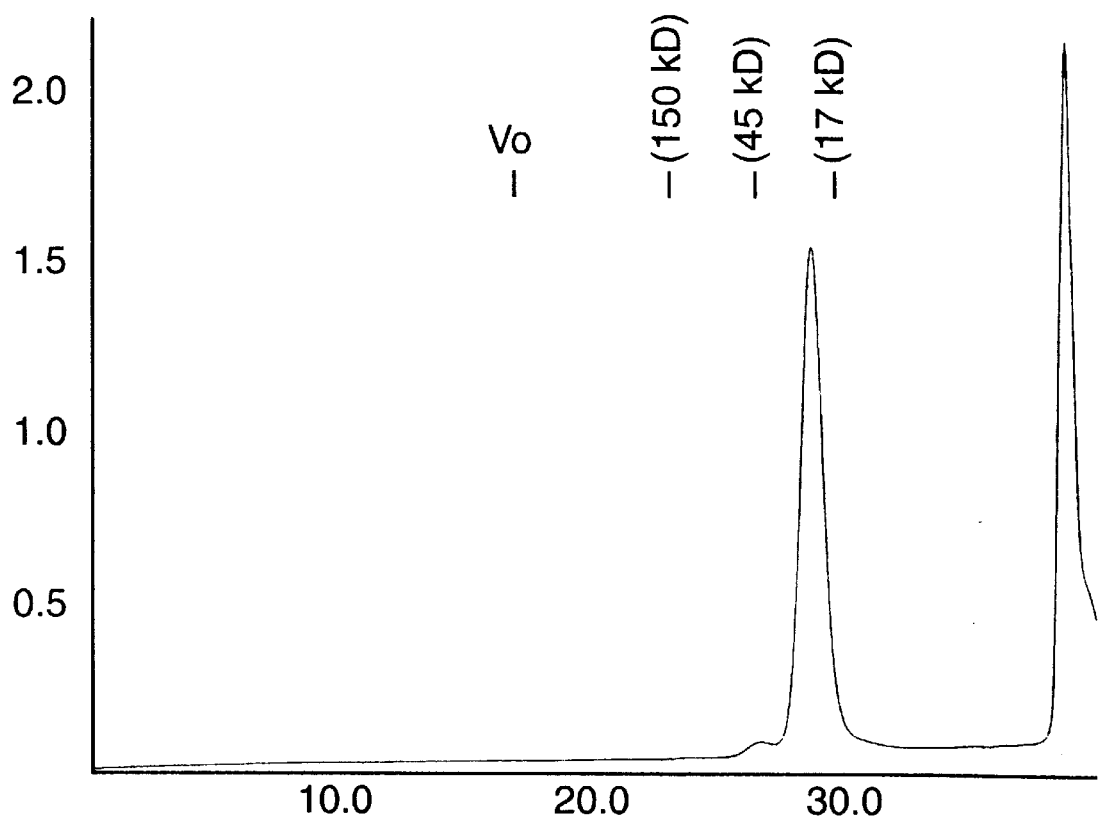
FIG. 3.

In addition to complicating the kinetic behavior of cdc25B inhibitors, the GST domain also complicates th(e purification process. GST-cdc25B (31–566) can be partially purified through the use of a GST-affinity column. The resultant product is usually less than 50% pure by the criteria of SDS PAGE. See FIG. 2. FIG. 2 shows a western blot in two sections. The section on the left (A), represents a Coomassie Blue stained PVDF-P blot and the section on the right (B) represents a rabbit anti-cdc25B probing of the same blot. Columns one (1) show GST-cdc25B(31–566) and columns two (2) show the special domain cdc25B (356–556). Subsequent chromatography steps utilizing anion or cation exchange, hydroxyapatite, p-chloromecuribenzoate, or gel filtration do not result in any further enhancement of purity. These results indicate that in addition to its probable dimeric behavior there is also a marked tendency for GST-cdc25B fusion proteins to non-specifically aggregate. The minimal domain cdc25B (356–556) protein or cdc25B catalytic macromolecules, on the other hand, are monomeric and have not been observed to non-specifically aggregate. Unlike GST-cdc25B, minimal domain cdc25B (356–556) protein or cdc25B catalytic macromolecules can be purified to homogeneity without the use of strong chaotropic agents. See FIG. 3 for a gel filtration size exclusion chromatograph of the purified monomeric special minimal domain cdc25B(356–556). FIG. 3 is a size exclusion chromatograph that shows the special domain acts as a monomer. The Y axis is absorbance at 220 nm. The X axis is retention time in minutes. Relative size markers are included.

The following $K_m$ rates,, using PNPP as substrate, were determined in a comparison of truncated cdc25B (356–556) protein with near full length GST-cdc25B (31–566).

| Enzyme Sample | approximate Km |
|---|---|
| cdc25B (356–556) | 2.0 mM |
| Mutein3 | 2.0 mM |
| GST-cdc25B (31–566) | 12.0 mM |

Mutein1, and mutein2 also have activity much higher than GST-cdc25B (31–566) and mutein3 has improved stability over GST-cdc25B (31–566). Mutein1, mutein2 and mutein3 are described in the next section.

$V_{max}$ was not measured due to impurity of GST-cdc25B fusion proteins.

The cdc25B (356–5506) enzyme exhibited higher activity per unit weight of protein than any other reported cdc25 phosphatase. For example, Dunphey and Kumagai, *Cell,* (1991) 67, pp. 189–196, report a $K_m$ and $V_{max}$ of 50 mM and 56 nmoles/min/mg for p35cdc25 at 37° C. using PNPP as substrate. This latter protein is the engineered recombinant C-terminal domain of the Drosophila cdc25 protein. Similarly, Horiguchi et al., *Biochem Pharmacol,* (1994) vol. 48, pp. 2139–2141, report a $K_m$ of 16.6 mM for GST-cdc25B (residues 355–566) using PNPP as substrate at 37° C. The purity was not reported, the calculated $V_{max}$ was not listed, nor can it be estimated without knowledge of the purity of the protein. Using the procedures described herein a $V_{max}$ for cdc25B(356–556) is equivalent to 500 +/−100 nmoles/min/mg.

When comparing our enzyme (tested at 25° C.) against other reported cdc25B proteins which were tested at 37° C., we found it necessary to increase our specific activities by 2–3 fold. This resulted from a measured 2–3 fold difference in rates we see at 37° C. versus 25° C. These data show that our truncated cdc25B protein representing amino acid residues 356–556 is more active than any reported cdc25 protein.

Another observation of this invention involves a comparison of the GST-cdc25B (302–566) parent protein versus the cdc25B (356–556) final product protein: The $K_m$ for PNPP as substrate using our truncated cdc25B (356–556) protein is 2–3-fold lower than for the parent GST-Xa site-Gly-Ile-cdc25B (302–566) protein.

Advanced Forms of the Macromolecule

Introduction

Improved forms of cdc25B (356–556) have also been designed. In the region spanning residues 302 to 355, there are many arginines which are attacked by factor Xa during the cleavage step. A new factor Xa site immediately preceding valine 356 was created to facilitate factor Xa processing directly to the fusion protein initiating at val356. Similarly, a second construct was designed with the substitution of two lysines for two arginines at residues 556–557. It was hoped that this substitution would prevent the factor Xa processing of this site which occurs during the normal processing of the GST fusion protein. The outcome of this latter digestion, if allowed to occur, is to generate cdc25B (356–556), which contains a 10 amino acid truncation at the C-terminus. The Arg-Arg to Lys-Lys replacement at 556–557 would allow for th, generation of a cdc25B molecule with an intact C-terminus. The improvements would be best exemplified by using both changes in the same construct yielding a more homogenous product with improved stability after Xa processing for uses; such as crystallization studies.

Experimental

A group of constructs was designed based on the mutagenesis of cdc25B sequence initiating with Gln302 and terminating with Gln566. The rationale for these constructs was to engineer in an improvement in stability and ease of isolation of the expressed protein. For this group, three principle constructs of cdc25B were created which when expressed in *E. coli* would be expected to give the sequence changes shown below, both design and actual results are shown.

ADVANCED FORM SEQUENCE COMPARISON
(Underlining shows changes from the native form.)

```
DESIGN

Nucleotide (Starts with residue 976.)

976 ...   1123 THROUGH 1146        ...    1732 THROUGH 1749      ... 1773

Wild Type

... GAA CCT AAA GCC CGC GTC CTC CGC ... CGG AGC CGG CGG GAG CTC ... 1773

Mutein1:

... GAA ATT GAA GGC CGC GTC CTC CGC ... CGG AGC CGG CGG GAG CTC ... 1773

Mutein2:

... GAA CCT AAA GCC CGC GTC CTC CGC ... CGG AGC AAG AAG GAG CTC ... 1773

Mutein3:

... GAA ATT GAA GGC CGC GTC CTC CGC ... CGG AGC AAG AAG GAG CTC ... 1773

Protein (Starts with residue 302.)

...351 352 353 354 355 356 357 358 ... 554 555 556 557 558 559 ... 566

Native0:

...GLU PRO LYS ALA ARG VAL LEU ARG ... ARG SER ARG ARG GLU LEU ... 566

Mutein1:

...GLU ILE GLU GLY ARG VAL LEU ARG ... ARG SER ARG ARG GLU LEU ... 566

Mutein2:

...GLU PRO LYS ALA ARG VAL LEU ARG ... ARG SER LYS LYS GLU LEU ... 566

Mutein3:

...GLU ILE GLU GLY ARG VAL LEU ARG ... ARG SER LYS LYS GLU LEU ... 566

RESULTS (Protein is listed first for comparison with above)

Protein      Starts at 356 357 358 ... 554 555 556 557 558 559 ... 566

Wild Type:              VAL LEU ARG ... ARG SER ARG  (Stops at arg556)

Mutein1:                VAL LEU ARG ... ARG SER ARG  (Stops at arg556)

Mutein2:                VAL LEU ARG ... ARG SER LYS LYS GLU LEU ... GLN

Mutein3:                VAL LEU ARG ... ARG SER LYS LYS GLU LEU ... GLN

Nucleotide     1138 THROUGH 1146   ...    1732 THROUGH 1749      ... 1773

Native0:                GTC CTC CGC ... CGG AGC CGG CGG GAG CTC ... 1773

Mutein1:                GTC CTC CGC ... CGG AGC CGG CGG GAG CTC ... 1773

Mutein2:                GTC CTC CGC ... CGG AGC AAG AAG GAG CTC ... 1773

Mutein3:                GTC CTC CGC ... CGG AGC AAG AAG GAG CTC ... 1773
```

The sequences above are described in full in CHARTS 13–16. It should be understood that the GST fusion proteins of these contructs are the form most useful as soluble and in some cases crystallizable constructs.

Mutein1 was constructed to introduce a new factor Xa site immediately preceding Val356, to reduce N-terminal microheterogeneity in the region from residue 302 through 355. Using pGEX-5X-3/cdc25B(302–566) as a template in the MORPH® mutagenesis system from 5 Prime 3 Prime, we used a single mutagenic oligonucleotide primer (5' GCG GAG GAC GCG GCC TTC AAT TTC CTC AGC CTC 3' SEQ. ID. NO. 41) to introduce the mutation. After DpnI digestion to eliminate non-mutated plasmid, the potential muteins were transformed into the repair-deficient *E. coli* BMH 71-18mutS. The mutation introduced a new Tsp509I restriction site which permitted us to screen for the desired mutants using restriction mapping. Circular plasmid DNA from a selected clone was then transformed into Promega JM109 cells after which DNA sequence analysis confirmed the desired nucleotide changes.

Mutein2 was constructed to substitute two residues in the C-terminus of the protein to decrease the incidence of factor Xa cleavage of these residues during protein workup. Thus, we desired to substitute two Lys groups for the two Arg groups at 556 and 557. Using the same template and protocol as that used with Mutein1, we introduced these mutations into the cdc25B gene using a single mutagenic oligonucleotide primer (5' GGG GAG CGG AGC AAG AAG GAG CTC TGT AGC 3' SEQ. ID. NO. 42). In this case, successful mutagenesis was identified by the elimination of a MwoI restriction site. After transformation in JM109 cells, DNA sequence was confirmed to be identical to that predicted.

To create Mutein3, a separate method was utilized. The cDNA of mutein 2, which already contained the RR→KK codon changes, was reconstructed using the Stratagene® quickchange system with primers (sense and antisense oligonucleotide primers containing the desired mutation; 5' GAG GCT GAG GAA ATT GAA GGC CGC GTC CTC CGC 3' SEQ. ID. NO. 43 or 5' GCG GAG GAC GCG GCC TTC AAT TTC CTC AGC CTC i3' SEQ. ID. NO. 41. After denaturation of the plasmid and annealing of the oligo primers containing the appropriate mutations, the product was treated with Pfu DNA polymerase to extend and incorporate the mutagenic primers, resulting in nicked circular strands. This product was then used to transform *E. coli* XL1-Blue supercompetent cells, which repair the nicks in the mutated plasmid. DNA fr)m the appropriate colonies was identified by restriction analysis with Tsp509I and then used to transform JM109. After preliminary restriction analysis with Tsp509I, isolated DNA was analyzed to confirm predicted nucleotide sequence.

The process of expressing the proteins encoded by these constructs was similar to that described for the wildtype protein. Each insert was ligated into the plasmid pGEX-5X-3 as described for the wild type system. *E. coli* strain JM109 was transformed with each plasmid and expression of the resulting GST fusion proteins of cdc25B minimal domains was conducted as described for the wild type enzyme system. The purification of these cdc25B proteins was conducted in a manner similar to that described for the wild type enzyme. Six liters of frozen *E. coli* cell paste were thawed and washed in deionized water, and then the washed pellet was resuspended in TEN buffer containing lysozyme, and the solution was incubated on ice for 10minutes. Supernatant was obtained by centrifugation at 20K RPM using an SS-34 rotor. The fusion protein was purified away from *E. coli* proteins by affinity chromatography on glutathione Sepharose affinity columns. After collection of the non-bound pool and additional washes, the resin (containing bound GST-cdc25B) was incubated with equilibration buffer containing factor Xa. After a period of time, the released protein is collected and concentrated by Amicon ultrafiltration. Next, the products were resolved from the contaminants and the factor Xa protease by anionic exchange chromatography (Q fast flow) using a linear gradient of NaCl. Fractions were assayed for phosphatase activity (hydrolysis of p-nitrophenylphosphate, PNPP), as well as by Western blotting using our own anti-cdc25B antibody. The purified proteins were analyzed by N-terminal sequencing and by mass spectrometry. The resulting proteins derived from the new constructs were shown to have the sequence shown above.

The following Specific Embodiments, Examples, Procedures and Techniques are provided to further support and illustrate, but not to limit, the invention.

Original Substrate—The CDNA encoding the entire sequence of cdc25B was obtained from Nagata, (see, Nagata A., Igarashi M., Jinno S., Suto K., and Okayama H. "An additional homolog of the fission yeast cdc25+ gene occurs in humans and is highly expressed in some cancer cells." *New Biol.* vol. 3(10), pp. 959–68 (1991). GENBANK/ S78187), then the full length (residues 1–2940) cdc25B DNA in a pCD2 vector was linearized with. Hind III to make the cDNA suitable as a template for the polymerase chain reaction (PCR). The cDNA was purified by gel electrophoresis. The identified linearized cDNA was subsequently purified using a Geneclean kit® commercially available from Bio 101®.

PCR Cloning—A defined region of cdc25B was desired, requiring the isolation of a section of the cdc25B CDNA which codes for residues 302–566 in the protein sequence. The nucleotide sequence representing this truncated cdc25B protein is residues 976–1773. To amplify only this sequence, the following DNA primers were prepared (ordered from Genosys®):

Geno-I - GCG GAT CCA GCG GCT CTT CCG CTC TC - (5'→3') SEQ. ID. NO. 30

Geno-II - GCC TCG AGT CAC TGG TCC TGC AGC CG (5'→3') SEQ. ID. NO. 31

The following reagents/system are used in the PCR reaction to generate the desired invention: 10 pmol Geno-I, 10 pmol Geno-II, 6 ng cdc25B template in pCD2, 200 µM dNTPs, 1× PCR Buffer (Perkin-Elmer® GeneAmp®), 1.5 mM $MgCl_2$, 50 mM KCl, 10 mM Tris-HCl, pH 3.3, 0.001% (w/v) gelatin, Sterile water to total volume 50 µl, 2.5 units Amplitaq DNA Polymerase.

Figure 4:
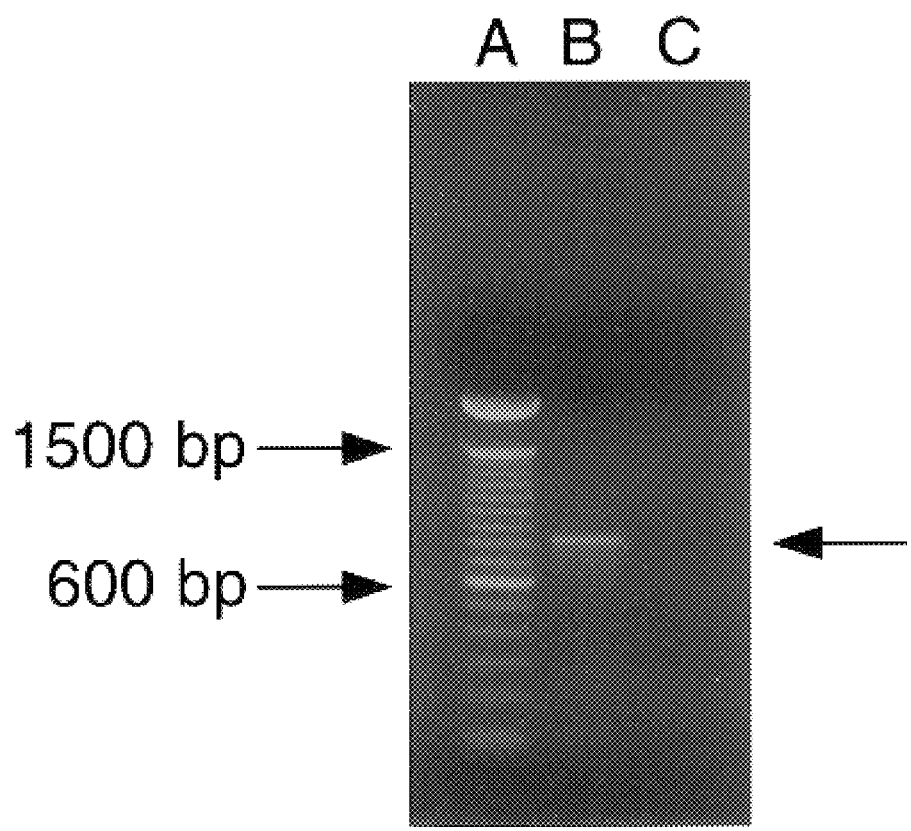
FIG. 4.

PCR cycling conditions are as follows: 8 minutes at 95°, followed by 25 cycles of the following, in order, (1 minute at 95°, 90 seconds at 50°, 2 minutes at 72°), after 25 cycles followed by 5 minutes at 72° followed by a change to 4° C. and hold. The PCR reaction yields a 0.8 Kilobase product, see FIG. 4, which is ligated immediately (without purification) into the TA Cloning vector pCRII (Invitrogen TA Cloning Kit) according to the manufacturer's directions. FIG. 4 is an agarose gel electrophoresis showing the product of the PCR reaction (0.8 Kb). In FIG. 4, column A shows the 100 base pair ladder, column B shows the cdc25B (976–1773) PCR product and column C shows the PCR control. The unlabeled arrow on the right side of the figure points to the PCR product. The product of the ligation is transformed into INVαF cells. After overnight incubation of the cells at 37 C, the resulting DNA of selected colonies is isolated using a Bio101® DNA isolation kit, digested with Bam HI and Xho I., and purified by agarose gel electrophoresis.

Ligation of 0.8 Kb Bam HI/Xho I TA cloning product into PGEX-5X-3-

PGEX-5X-3 (Pharmacia Biotech®) is prepared for ligation by sequential digestion with the restriction enzyme Xho I at 37° C. in 50 mM Tris-HCL (pH 8.0), 10 mM $MgCl_2$ and 50 mM NaCl, followed by digestion with Bam HI at 37° C. in 50 mM Tris-HCl (pH 8.0), 10 mM $MgCl_2$ and 100 mM NaCl. The resultant double-digested plasmid is subjected to electrophoresis on a 0.8% agarose gel in 1× TAE (Tris-acetate-EDTA buffer). After electrophoresis, the gel is soaked in 1× TAE with 0.5 µg/ml ethidium bromide (EtBr) so that the DNA could be visualized under long-wave UV. The 0.8 kb product is excised from the gel and is purified using Geneclean III® from Bio 101® as recommended by the manufacturer. The following ligation conditions are utilized:

A. PGEX-5X-3 alone/representing a no insert control

≈250 ng PGEX-5X-13, Bam HI/Xho I digested

1 Unit T4 DNA ligase (Gibco BRL®,1× ligase buffer (Gibco BRL®)

50 mM Tris-HCl (pH 7.6), 10 mM $MgCl_2$, 1 mM ATP, 1 mM DTT

5% (w/v) polyethylene glycol—8000, 1 mM dATP (Gibco BRL®) Sterile $H_2O$ to give total volume 10 µl, B. PGEX-5X-3/cdc25B (302–566) insert ≈250 ng PGEX-5X-3", Bam HI/Xho I digested ≈100 ng 0.8 Kb cdc25B minimal domain from TA cloning, Bam HI/Xho I digested and gel purified 1 Unit T4 DNA ligase (Gibco BRL®), 1× ligase buffer (Gibco BRL®)

1 mM dATP (Gibco BRL®), Sterile $H_2O$ to give total volume 10 µl

Both reactions are ligated overnight at 15° C.

Transformation of *E. coli* Strain JM109

The transformation reaction is conducted as follows:

1. 5 µl ligation reaction is added to 100 µl Promega® JM109 competent *E. coli*; this suspension is incubated on ice for 1 hour.
2. Incubate at 42° C. for 90 seconds.
3. Cool on ice 1 minute.
4. Add 250 µl LB medium. Incubate with shaking for 1 hour.
5. Plate 10, 100 and 200 µl on LB+Agar+100 µg/ml ampicillin® plates.

The agar plates spread with the transformation mixture are incubated overnight at 37° C. Colonies are abundant on PGEX-5X-3/cdc25B insert plates and sparse on control plates. For our example, sixteen colonies were picked (1–2 controls; 3–16 cdc25B insert) and grown overnight in 5 ml cultures of LB+100 µg/ml ampicillin®.

Miniprep Analysis

Figure 5:
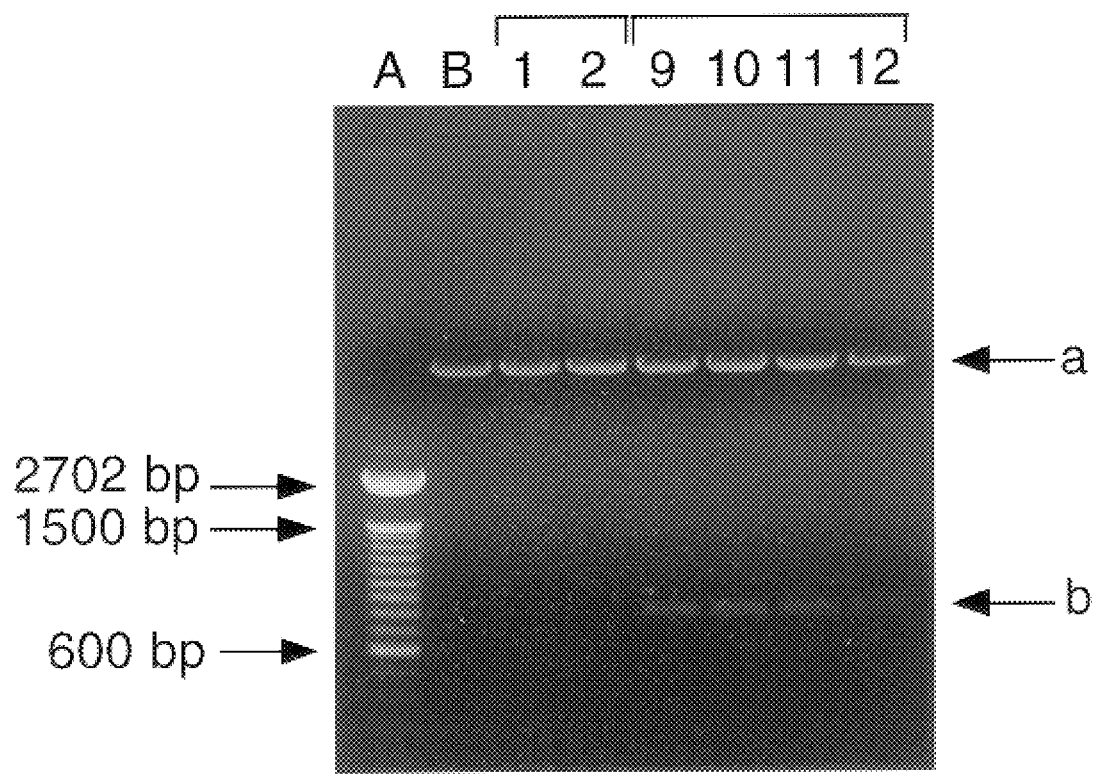
FIG. 5.

DNA is purified from 1–12 cultures using 1.5 ml of culture in a Bio 101® RPM® kit. The DNA is eluted in 50 µl sterile $H_2O$, and digested with Bam HI and Xho I simultaneously in React 2 buffer at 37° C. for 1 hour. Samples are run on a 0.8% agarose gel in 1× TAE buffer containing 0.5 µg/ml EtBr. In our analysis, samples 9–12 all yielded an insert of the correct size (≈0.8 Kb). See FIG. 5, an agarose gel electrophoresis of plasmid mini preps obtained from transformed JM109 *E coli*. Lanes 9–11 contain the desired insert, lane A shows the 100 bp ladder, lane B shows the pGEX-5X-3 (linearized), lanes 1 and 2 show pGEX-5X-3 with no inserts, i.e. controls, the arrow on the right side of the figure labeled "a" shows the linearized plasmid and the other arrow labeled "b" shows the insert. Expression of the human recombinant cdc25B protein (GST-Xa site-Gly-Ile-cdc25B (302–566) in *E. coli*).

*Escherichia coli* strain JM109, containing the expression vector pGEX-5x-3 (a vector which also contains the coding region for the factor Xa site) with the cdc25B insert (976–1773), was grown on Luria broth and/or M9 medium containing 0.5% yeast extract (M9YE) as seed and production media. *E. coli* stored at −80° C. in 20% glycerol was used as the primary inoculum for the seed stage fermentation which was carried out at 37° C. in 100 ml volumes contained in 500 ml wide mouth fermentation flasks shaken at 200 rpm for 12 hr. The seed media (LB or M9YE) contained ampicillin® at 100 mg/L. The mature seed fermentations were used to inoculate production fermentations at a 2% rate; in all cases the same medium containing ampicillin® at 100 mg/L was used for the seed and production fermentations. The production fermentations were carried out identically to the seed fermentations for ca. 2.5 hr when the turbidity at 660 nm reached 1.0 unit (+/−0.2). At this time, IPTG was added to a final concentration of 0.4 mM. The induced fermentations were carried out for another 3.5 hr when the turbidity reached about 3 units. The completed fermentation was harvested by centrifugation.

Purification of *E. coli* Expressed Catalytic cdc25B macromolecules

The strategy of affinity purification of GST-Xa site-GI-cdc25B (302–566) and subsequent processing and purification of truncated cdc25B: The recombinant fusion protein, produced in *E. coli*, is designed to have a glutathione S-transferase (GST) tag linked to the cdc25B protein encompassing amino acid residues 302–566 of the full length protein. A. factor Xa cleavage site (IEGR) is situated immediately after the GST polypeptide, and prior to the beginning of the cdc25B sequence. Two additional amino acid residues are positioned immediately after the factor Xa cleavage site as a result of the restriction site nucleotide coding sequence. The factor Xa cleavage site allows for cleavage of the GST tag from the truncated cdc25B protein using factor Xa protease.

Specific description of the procedure:

i) Methodology: Two liters of *E. coli* cell paste prepared by the expression system defined above is lysed in the presence of lysozyme (1 mg/ml) and fresh dithiothreitol (DTT) (20 mM) in TEN buffer (50 mM Tris HCl, 0.5 mM EDTA, 300 mM NaCl, 0.2% NP-40, pH 8.0). This procedure is analogous to an earlier method described by Millar et al. (1991) for a yeast GST-cdc25C truncated protein. The lysate is centrifuged to pellet cell debris and insoluble protein, and the supernatant is collected. This solution is mixed with 20 ml of glutathione-Sepharose (Pharmacia Biotech®) which has been pre-equilibrated with factor Xa digestion buffer (50 mM Tris HCl, 100 mM NaCl, 1 mM CaCl2, pH 8.0). The fusion protein is purified away from *E. coli* proteins by affinity chromatography on the glutathione Sepharose affinity column. After collection of the non-bound pool, the resin, which contains bound GST-GI-cdc25B (302–566) is incubated with equilibration buffer containing factor Xa (50 mM Tris HCl, 100 mM NaCl, 1 mM $CaCl_2$, pH 8.0) in a manner analogous to that described by Abeliovich and Schlomai (Anal. Biochem. 228: 351–354 (1995) ("Reversible oxidative aggregation obstructs specific proteolytic cleavage of glutathione S-transferase fusion proteins") for the factor Xa cleavage of glutathione Sepharose bound GST-UMSBP (universal minicircle sequence binding protein).

To gauge the amount of time required for the digestion process, at various timed intervals the suspension is centrifuged and an aliquot of the supernatant is removed. This aliquot is -assayed using the PNPP method described above. Increasing amounts of cdc25B phosphatase activity versus PNPP are observed until a plateau in activity is found. Similarly, aliquots may also be subjected to SDS polyacrylamide gel electrcophoresis to determine levels and purity of the cdc25B product.

The method by which a bound GST fusion protein containing the desired protein partner is cleaved by factor Xa while still bound to the glutathione resin is also detailed in the Pharmacia Biotech® protocol booklet for pGEX vector expression ("GST Gene Fusion System, 2nd Edition, Revision 2, Pharmacia Biotech®, p. 17–18, 1996). The eluate from this step is pooled and concentrated by ultrafiltration (YM10 filter, Amicon), and exchanged into a buffer system used for equilibration of a Q fast flow anion exchange column (25 mM Tris HCl, 10 mM DTT, pH 8.0). The equilibrated pool concentrate is loaded onto a Q fast flow column (10 ml bed volume, 1.6 cm diameter) and the non-bound fraction is removed. The truncated cdc25B (356–556) protein product is resolved from contaminants using a linear gradient of NaCl (100–190 mM) over a 36 minute period. Appropriate fractions are collected and concentrated by ultrafiltration (Amicon) to a minimum of 2 mg/ml. Finally, glycerol is added to provide a 50% solution, with storage at −20 C. APMSF and/or pefabloc serine protease inhibitors, are also added prior to storage if residual factor Xa activity is measured. The amount of inhibitor required to completely inactivate all protease is determined using an assay for the protease.

ii) Demonstration of homogeneity was accomplished by SDS polyacrylamide gel electrophoresis, C4 reverse phase HPLC, N-terminal sequencing, mass spectroscopy, and Western blotting. Validation of the sequence was completed by N-terminal sequencing, mass spectroscopy, C4 reverse phase HPLC, and Western blotting using a commercially available antibody versus the C-terminus of cdc25B. Both the fusion protein and the minimal domain of cdc25B (356–556) were shown to be enzymatically active as a phosphatase against p-nitrophenylphosphate (PNPP).

VHR-LIKE CONSTRUCTS

The cloning, expression, and purification of an active and soluble truncated form of cdc25B based on the alignment and modelling of cdc25 with a family of dual specificity phosphatases.

Introduction. CDC25 phosphatases are responsible for the dephosphorylation and activation of cyclin-dependent protein kinases. The latter events result in cell cycle progression. Blockade of cell cycle progression could be pursued as a strategy for design of novel anti-cancer drug templates. This portion of this invention is based upon the design of cdc25 proteins that are aligned with a family of dual specificity phosphatases. Here we model a cdc25 protein sequence against a known and published 3D structure of a similar phosphatase called VHR (vaccinia H1-related phosphatase). The latter phosphatase was recently crystallized (J. Yuvaniyama, J. M. Denu, J. E. Dixon, and M. A. Saper. Crystal Structure of the Dual Specificity Protein Phosphatase VHR. *Science* 272: 1328–1331). VHR shows limited sequence identity to cdc25 proteins, and has been used frequently as the model for studies devoted to understanding the mechanism of dual specificity phosphatases such as cdc25. It is also useful as a structural model for cdc25 proteins, since it has a relatively low molecular weight mass of about 20,500. See, J. M. Denu, G. Zhou, L. Wu, R. Zhao, J. Yuvaniyama, M. A. Saper, and J. E. Dixon. The purification and characterization of a human dual-specific protein tyrosine phosphatase. *J. Biol. Chem.* 1995 Feb. 24; 270(8): 3796–803.

Experimental Approach. Software tools were used to obtain a tentative sequence alignment of cdc25B with other protein tyrosine phosphatases. The alignment of a structure between the PTPases gave the best correlation with a segment consisting of a region in the PTPases that is similar to the catalytic domain of cdc25B. While the sequence similarity is very low, we did see a reasonable sequence correlation factor between the VHR sequence and the cdc25B minimal domain. Based on this sequence alignment, the cdc25B minimal domain was threaded through the known VHR crystallographic structure to obtain a reasonable model for cdc25B minimal domain. Using this model, we could further truncate the minimal domain by removing potential random coil regions of the structure that are needed to connect domains (i.e., begin with residue His364 and end with residue Arg529. In following this model, we propose that if a domain over this region is expressed and purified it would be a significantly smaller domain and would be much more amenable for NMR studies, and would also remove what is proposed to be floppy regions that may adversely effect the crystallization studies.

Materials and Methods.

Materials. Glutathione Sepharose 4B and Q fast flow ion exchange matrix were obtained from Pharmacia Biotech, Factor Xa was purchased from Boehringer Mannheim. The colorimeiric substrate, p-Nitrophenyl phosphate (PNPP) was obtained from Sigma Diagnostics.

Original Substrate The cDNA encoding the entire sequence of human cdc25B in pCD2 was prepared for use as a template for the polymerase chain reaction (PCR) by first linearizing with Hind III. Subsequently, the cDNA was isolated by gel electrophoresis. This is followed by purification using a Geneclean® kit (Bio 101®).

PCR Cloning. A defined region of cdc25B was desired, requiring the isolation of a section of the cdc25B CDNA (residues 1162 to 1659) which codes for amino acid residues 364 to 529. To amplify only this sequence, the following DNA primers, listed in a 5'→3' orientation were prepared/obtained from Genosys®: Geno-III (GCG GAT CCA GCA CGA TGA GAT CGA GAA) SEQ. ID. NO. 44, and Geno-IV (GCC TCG AGT CAC CGG TAG TCC TGG GGT) SEQ. ID. NO. 45, (the italicized letters indicate the positions of engineered restriction sites). A reaction (final volume of 100 ul) containing 20 pmol Geno-II, 20 pmol Geno-IV, 12 ng cdc25B template, 200 $\mu$M dNTPs, 1× PCR Buffer [(Perkin-Elmer GeneAmp®), 1.5 mM MgCl$_2$, 50 mM KCl, 10 mM Tris-HCl pH 8.3, 0.001% (w/v) gelatin], and sterile water was used in the PCR reaction to generate the desired insert. 2.5 units Amplitaq Gold® DNA Polymerase was used for this PCR reaction, and cycling conditions were as follows: 8 minutes at 95°, [1 minute at 95°, 90 seconds at 50°, 2 minutes at 72°, for a total of 25 cycles]; finally, cycling is completed with incubation for 5 minutes at 72°, followed by a 4° C. hold temperature. The PCR reaction product was immediately (without prior purification) ligated into the TA Cloning vector pCRII (Invitrogen TA® Cloning lit) according to the manufacturer's directions. The product of the ligation was transformed into INVαF' cells. Isolated colonies were selected on a basis of ampicillin resistance, and after overnight incubation of selected colonies at 37° C., the resulting DNA was isolated using a Bio101® DNA isolation kit, digested with Bam HI and Xho I, size selected by agarose gel electrophoresis, and purified using GeneClean Spin Kit (Bio 101)®.

Ligation of Ban HI/Xho I TA cloning product into PGEX-5X-3. PGEX-5X-3 (Pharmacia Biotech®) was prepared for ligation by digestion with the restriction enzymes BamHI and EcoRI at 37° C. in 50 mM Tris-HCL (pH 8.0), 10 mM $MgCl_2$ and 50 mM NaCl (React 2 buffer, Gibco BRL). The resultant linearized plasmid was subjected to electrophoresis on a 0.8% agarose gel in 1× TAE (Tris-acetate-EDTA buffer). After electrophoresis, the gel was soaked in 1× TAE with 0.5 μg/ml ethidium bromide (EtBr) so that the DNA could be visualized under long-wave WV. The product was excised from the gel and was purified using Geneclean III from Bio 101 as recommended by the manufacturer. The following ligation conditions were utilized:

A. PGEX-5X-3 alone/representing a no insert control. A mixture of ≈100 ng PGEX-5X-3, which was linearized with Bam HI/EcoRI, together with 1 Unit of T4 DNA ligase (Gibco BRL®) 1× ligase buffer [50 mM Tris-HCl (pH 7.6), 10 mM $MgCl_2$, 1 mM ATP, 1 mM DTT, 5% (w/v) polyethylene glycol 8000, (Gibco BRL®)], 1 mM dATP (Gibco BRL®, and sterile $H_2O$ was prepared to give a total volume of 10 μl.

B. PGEX-5X-3/cdc25B insert. A mixture of ≈100 ng PGEX-5X-3, which was Bam HI/EcoRI digested, =100 ng cdc25B minimal domain from the TA cloning experiment (Bane HI/Xho I digested), 1 Unit of T4 DNA ligase (Gibco BRL®, 1× ligase buffer (Gibco BRL), 1 mM dATP (Gibco BRL), and sterile $H_2O$ was prepared to give a total volume of 10 μl. Both ligation reactions were allowed to proceed overnight at 15° C.

Transformation of E. coli Strain JM109. 5 μl of the ligation reaction was added to 100 μl of JM109 (Promega®) competent cells (E. coli). This suspension was incubated on ice for 1 hour, incubated at 42° C. for 90 seconds, and cooled on ice for 1 minute. 250 μl of SOC medium was added, followed by incubation at 37° C. with shaking for 1 hour. The mixture was used for application of 10, 50 and 200 μl aliquots onto (1%) agar plates containing LB medium and ampicillin (100 μg/ml). After streaking the agar plates with the transformation mixture, the plates were incubated overnight at 37° C. Colonies were picked and grown overnight in 5 ml cultures of LB+100 μg/ml Ampicillin.

Miniprep Analysis. DNA was purified from cultures using the Bio 101 RPM kit, and then digested with Bam HI and Xho I simultaneously in React 2 buffer at 37° C. for 1 hour. Samples were run on a 0.8% agarose gel containing 1× TAE buffer and 0.5 μg/ml EtBr to identify correct clones.

DNA sequencing showed the residue sequences were as predicted.

Expression of the human recombinant truncated cdc25B protein (GST-cdc25B (364–529)) in E. coli. Seed fermentation: E. coli was inoculated into 100 ml vols. of M9 medium containing thiamin, at 5pg per ml, contained in 500 ml large mouth fermentation flasks. The medium contained 100 mg of ampicillin/L.

The inoculated flasks were incubated for 20 hr at 37 C while shaking at 200 rpm. M9 was prepared as described below. Production fermentation: Production flasks (as above) containing M9 with filter sterilized thiamin (as above) were inoculated with the mature seed fermentation at a 3% rate. This fermentation was continued for 3.25 hr at 37 C while shaking at 200 rpm until the turbidity at 660 nm reached about 0.6. At this time, filter sterilized IPTG was added to a final concentration of 0.2 mM, and the temperature was shifted to 30 C.

The production fermentation continued at 200 rpm for an additional 3.5 hr until the turbidity reached about 3.0 when harvest was done by centrifugation. Eighty flasks were fermented to achieve an 8 L production batch.

M9 medium contains dibasic sodium phosphate, 6 g; monobasic potassium phosphate, 3 g; NaCl, 0.5 g, and ammonium chloride 1 g, per L of deionized water. One hundred ml vols. of M9 contained in 500 ml wide mouth fermentation flasks were sterilized by autoclaving for 30 min. The presterilization pH was adjusted to 7.3 with KOH. One L of sterile basal M9 was completed through the aseptic addition of filtered sterilized $1MgSO_4$, 2 ml; 20% glucose, ml, 1M $CaCl_2$, 0.1 ml and thiamine, 5 μg.

Affinity purification of GST-cdc25B (VHR-like domain) by a Glutathione Sepharose chromatography (column and factor Xa processing to the final product. Six liters of frozen E. coli cell paste were thawed and washed in deionized water, and the washed pellet was resuspended in 0.5 mM EDTA, 20 mM DTT, 0.3M NaCl, 0.2% NP-40 and 50 mM Tris.Hcl pH 8.0. Egg lysozyme (Sigma) was added at 1 mg/ml, and the solution was incubated on ice for 10 minutes. Supernatant was obtained by centrifugation at 14 k RPM using an SS-34 rotor for 35 minutes at 5° C. The fusion protein is purified away from E. coli proteins by affinity chromatography on the glutathione Sepharose affinity column. After collection of the non-bound pool, the resin, which contains bound GST-GIQ-cdc25B (364–529) was incubated with equilibration buffer containing factor Xa (50 mM Tris HCl, 100 mM NaCl, 1 mM CaCl2, pH 8.0) in a manner analogous to that described above. Specifically, the collected lysate was batch mixed with 15 ml of packed glutathione resin. The slurry was poured into a column and washed extensively with the lysis buffer described above (w/o lysozyme). Finally the protein charged column matrix was washed with factor Xa digestion buffer 50 mM Tris HCl, 100 mM NaCl, and 1 mM $CaCl_2$ pH 8.), followed by the addition of 125 ug of Factor Xa with mixing in 20–30 ml of digestion buffer. After 12–14 hrs incubation at 8° C. the Xa released material is collected and concentrated by Amicon ultrafiltration (YM-10 filter). The concentrate is diluted 3× with deionized water to lower the salt concentration for the ion exchange chromatography step.

Q Fast Flow column (ion exchange) chromatography. Upon the desired completion of Xa digestion of cdc25B, the products are resolved from the contaminants by anionic exchange chromatography. Proteins were resolved from one another by a linear gradient of 100–190 mM NaCl over a period of 36 min.

Electrophoresis and Western Blotting. SDS gel electrophoresis were performed according to Laiemmli, supra. Western blots were completed using a semi-dry electroblotter onto PVDF membranes (Millipore) with a constant current set at 125 mA/gel (7×9 cnm). Blots were visualized by either staining with Coomassie blue R250 (.2% WNV) in 50% Ethanol, 5% Acetic acid followed by a destaining step using 50% ethanol solution, or alternatively, were processed for immunostaining.

For the latter, blots were first blocked in 2% nonfat dried milk in lx phosphate buffered saline for 5 min washed in tris (,20 mM) buffered saline (TBS) and exposed to anti-cdc25B primary antibody (1:500 dilution in 1% BSA in TBS supplemented with $NaN_3$ as a preservative) and incubated for 1 hr. The blots are washed in 0.5% Tween-20 in TBS for 10 min followed by 5 min in TBS and then exposed to secondary antibody (anti-rabbit($F_C$) Alkaline Phosphatase conjugate, Promega®) at 1:1000 dilution. The location of cdc25B on blots was identified using an alkaline phosphatase NBT/BCIP substrate system (BioRad®). Following development, blots were then air dried prior to storage.

Enzyme assay and Kinetic Analyses. Assays of PNPP hydrolase activity associated with cdc25B are conducted using the reagents described earlier. These reagents include (as final concentrations in 125 ul): 25 mM Hepes, pH 8.0, 10 mM DTT, 0.1 mg/ml bovine serum albumin, and variable concentrations of pNPP. For assays where a single concentration of substrate is used at saturation, we customarily use a final concentration of 20 mM pNPP. Assay solution is prepared in a final volume of 100 ul, including the addition of freshly prepared dithiothreitol At the initiation of the assay, 25 ul of enzyme is added with mixing, and a continuous recording of absorbances at 405 min is completed over a short time period. For the determination of $K_m$ and $V_{max}$ (specific activity), multiple pNPP concentrations are used at a constant enzyme concentration. Rates at each concentration of substrate are determined and the $K_m$ and $V_{max}$ calculated from line fitting to a Michaelis Menten equation. The velocity of the reaction is defined as follows: One unit of activity is defined as nmoles of pNPP hydrolyzed per minute per milligram of enzyme protein at 25° C.

Sequence analysis and mass spectroscopy. Amino terminal sequencing of purified cdc25B proteins was performed on an ABI 476A protein sequencer. Database searches were conducted using the Genetics Computer Group software package (GCG). The amino acid sequences of several homologous proteins were examined by the program FASTA.

... A mass ion representing the major product of the cdc25B protein preparation has been identified at about 19,772 daltons. This mass corresponds directly to the sequence of GIQ-cdc25B (364–529).

Characterization of the purified truncated recombinant human cdc25B by enzymatic activity. Both the fusion protein and the minimal domain of cdc25B (364–529) were shown to be enzymatically active as a phosphatase against p-nitrophenylphosphate (PNPP). $K_m$ and $V_{max}$ determinations of the GST-free catalytic domain of cdc25B were made using the assay conditions defined previously as well as by a 96 well plate assay method. Enzymatically, the catalytic domain represented by residues 364–529 is active as an enzyme with PNPP as substrate, giving an average $K_m$ of about 28 mM and an average $V_{max}$ of about 250 nmoles/min/mg.

VHR-Like-CHART A

The amino acid sequence of human cdc25B showing the VHR like region, underlined, from residue 364 to 529. SEQ. ID. NO. 24.

```
  1 MEVPQPEPAP GSALSPAGVC GGAQRPGHLP GLLLGSHGLL GSPVRAAASS
 51 PVTTLTQTMH DLAGLGSRSR LTHLSLSRRA SESSLSSESS ESSDAGLCMD
101 SPSPMDPHMA EQTFEQAIQA ASRIIRNEQF AIRRFQSMPV RLLGHSPVLR
151 NITNSQAPDG RRKSEAGSGA ASSSGEDKEN DGFVFKMPWK PTHPSSTHAL
201 AEWASRREAF AQRPSSAPDL MCLSPDRKME VEELSPLALG RFSLTPAEGD
251 TEEDDGFVDI LESDLKDDDA VPPGMESLIS APLVKTLEKE EEKDLVMYSK
301 CQRLFRSPSM PCSVIRPILK RLERPQDRDT PVQNKRRRSV TPPEEQQEAE
351 EPKARVLRSK SLCHDEIENL LDSDHRELIG DYSKAFLLOT VDGKHODLKY
401 ISPETMVALL TGKFSNIVDK FVIVDCRYPY EYEGGHIKTA VNLPLERDAE
451 SFLLKSPIAP CSLDKRVILI FHCEFSSERG PRMCRFIRER DRAVNDYPSL
501 YYPEMYILKG GYKEFFPOHP NFCEPODYRP MNHEAFKDEL KTFRLKTRSW
551 AGERSRRELC SRLQDQ
```

Physical characteristics of the purified truncated recombinant human cdc25B

The purified cdc25B protein was immunodetected by an antibody as demonstrated by unpublished western blots. The purified protein exhibits a single peak when analyzed by C4 reverse phase JIPLC. The amino terminus of the purified cdc25B protein was determined to be Gly-Ile-Gln-His364.

VHR-Like-CHART B

The amino acid sequence of human VHR phosphatase. Reference: A novel dual specificity phosphatase induced by serum stimulation and heat shock, Ishibashi T., Bottaro D. P., Michieli P., Kelley C. A., Aaronson S. A., *J. Biol. Chem.*, vol 269(47), pp. 29897–902 (19)94). SEQ. ID. NO. 25.

```
  1 MSGSFELSVQ DLNDLLSDGS GCYSLPSQPC NEVTPRIYVG NASVAQDIPK
 51 LQKLGITHVL NAAEGRSFMH VNTNANFYKD SGITYLGIKA NDTQEFNLSA
101 YFERAADFID QALAQKNGRV LVHCREGYSR SPTLVIAYLM MRQKMDVKSA
151 LSIVRQNREI GPNDGFLAQL CQLNDRLAKE GKLKP
```

We claim:

1. A fusion protein comprising a protein having a GST region operably linked to SEQ. ID. NO. 16.

2. A peptide comprising the amino acid residues of SEQ. ID. NO. 23, produced as a product from the fusion protein that is comprised of GST operably linked to the peptide sequence Ile-Glu-Gly-Arg-Gly-Ile operably linked to SEQ. ID. NO. 16.

3. A fusion protein comprising a protein having a GST region operably linked to SEQ ID NO: 23.

* * * * *